United States Patent
Arvanitis et al.

[11] Patent Number: 6,159,980
[45] Date of Patent: *Dec. 12, 2000

[54] PYRAZINONES AND TRIAZINONES AND THEIR DERIVATIVES THEREOF

[75] Inventors: Argyrios Georgios Arvanitis, Kennett Square, Pa.; Richard E. Olson, Wilmington; Charles R. Arnold, III, New Castle, both of Del.; William E. Frietze, Kennett Square, Pa.

[73] Assignee: Dupont Pharmaceuticals Company, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/929,935

[22] Filed: Sep. 15, 1997

Related U.S. Application Data
[60] Provisional application No. 60/026,373, Sep. 16, 1996.

[51] Int. Cl.[7] .................... C07D 241/18; A61K 31/495
[52] U.S. Cl. .................... 514/255; 514/252; 514/253; 514/241; 514/245; 514/242; 514/235.8; 514/232.2; 514/227.8; 544/408; 544/180; 544/182; 544/295; 544/212; 544/219; 544/82; 544/120; 544/58.6
[58] Field of Search .................... 544/408, 180, 544/182, 295, 82, 120, 58.6; 514/255, 252, 253, 241, 245, 242, 235.8, 232.2, 227.8

[56] References Cited

U.S. PATENT DOCUMENTS
| | | | |
|---|---|---|---|
| 5,418,233 | 5/1995 | Linz et al. | 514/247 |
| 5,518,994 | 5/1996 | Kawamura et al. | 504/242 |

FOREIGN PATENT DOCUMENTS
| | | |
|---|---|---|
| 4139993 | 1/1994 | Australia . |
| 0242957 | 10/1987 | European Pat. Off. . |
| 0576350 | 12/1993 | European Pat. Off. . |
| 92/13451 | 8/1992 | WIPO . |
| 94/13661 | 6/1994 | WIPO . |
| 94/13676 | 6/1994 | WIPO . |
| 94/13677 | 6/1994 | WIPO . |
| 95/10506 | 4/1995 | WIPO . |
| 95/33727 | 12/1995 | WIPO . |
| 95/33750 | 12/1995 | WIPO . |
| 95/34563 | 12/1995 | WIPO . |
| 97/40024 | 10/1997 | WIPO . |

OTHER PUBLICATIONS
Appleton et al, Chemical Abstracts, vol. 93 entry 114569 (1980).
H. Neunhoeffer, 1,2,4–Triazines and the Benzo Derivatives, Comprehensive Heterocyclic Chemistry, Katritsky & Rees, ed, vol. 3, pp. 385–456, 1984.
Nakamura et al., Agric. Biol. Chem., 47 (7), 1561–1567, 1983.

*Primary Examiner*—John M. Ford
*Attorney, Agent, or Firm*—Scott K. Larsen

[57] ABSTRACT

Corticotropin releasing factor (CRF) antagonists of Formula (I)

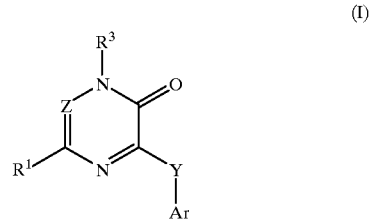

and their use in treating psychiatric disorders and neurological diseases including major depression, anxiety-related disorders, post-traumatic stress disorders, supranuclear palsy and eating disorders.

28 Claims, No Drawings

PYRAZINONES AND TRIAZINONES AND THEIR DERIVATIVES THEREOF

This application claims the benefit of U.S. Provisional Application No. 60/026,373, filed Sep. 16, 1996.

FIELD OF THE INVENTION

This invention relates to novel compounds and pharmaceutical compositions, and to methods of using same in the treatment of psychiatric disorders and neurological diseases including major depression, anxiety-related disorders, post-traumatic stress disorders, supranuclear palsy and eating disorders.

BACKGROUND OF THE INVENTION

Corticotropin releasing factor (herein referred to as CRF), a 41 amino acid peptide, is the primary physiological regulator of proopiomelanocortin(POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and eating disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9–41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

DuPont Merck PCT application WO95/10506 describes corticotropin releasing factor antagonist compounds and their use to treat psychiatric disorders and neurological diseases.

European patent application 0 576 350 A1 by Elf Sanofi describes corticotropin releasing factor antagonist compounds useful in the treatment of CNS and stress disorders.

Pfizer patent applications WO 94/13676, WO 94/13677, WO 94/13661, WO 95/33750, WO 95/34563, WO 95/33727 describe corticotropin releasing factor antagonist compounds useful in the treatment of CNS and stress disorders.

All of the aforementioned references are hereby incorporated by reference.

The compounds and the methods of the present invention provide for the production of compounds capable of inhibiting the action of CRF at its receptor protein in the brain. These compounds would be useful in the treatment of a variety of neurodegenerative, neuropsychiatric and stress-related disorders such as affective disorders, anxiety, depression, post-traumatic stress disorders, supranuclear palsy, seizure disorders, stroke, irritable bowel syndrome, immune suppression, Alzheimer's disease, gastrointestinal disease, anorexia nervosa or other eating disorders, drug or alcohol withdrawal symptoms, drug addiction, inflammatory disorders and fertility problems. It is further asserted that this invention may provide compounds and pharmaceutical compositions suitable for use in such a method.

SUMMARY OF THE INVENTION

This invention is a class of novel compounds which are CRF receptor antagonists and which can be represented by Formula (I):

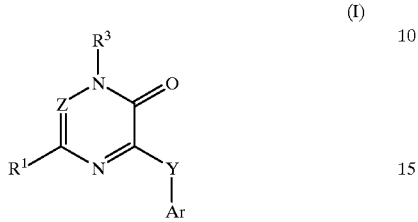

(I)

or a pharmaceutically acceptable salt form thereof, wherein Z is $CR^2$ or N;

when Z is $CR^2$:

Y is $NR^4$, O or $S(O)_n$;

Ar is phenyl, naphthyl, pyridyl, pyrimidinyl, pyridazinyl, pyrazinyl, 1,3,5-triazinyl, 1,2,4-triazinyl, furanyl, quinolinyl, isoquinolinyl, thienyl, imidazolyl, thiazolyl, indolyl, indolinyl, pyrrolyl, oxazolyl, benzofuranyl, benzothienyl, 2,3-dihydrobenzofuranyl, 2,3-dihydrobenzothienyl, benzothiazolyl, indazolyl, isoxazolyl or pyrazolyl, each substituted with 0 to 4 $R^5$ groups; wherein Ar is attached to Y through an unsaturated carbon;

$R^1$ is H, halo, $C_1$–$C_{10}$ alkyl, $C_2$–$C_{10}$ alkenyl, $C_2$–$C_{10}$ alkynyl, $C_3$–$C_8$ cycloalkyl, $C_1$–$C_4$ haloalkyl, aryl, heterocyclyl, —CN, —$OR^7$, —SH, —$S(O)_nR^{13}$, —$COR^7$, —$CONR^6R^7$, —$CO_2R^7$, —$OC(O)R^{13}$, —$NR^8COR^7$, —$N(COR^7)_2$, —$NR^8CONR^6R^7$, —$NR^8CO_2R^7$, or —$NR^6R^7$, wherein $C_1$–$C_{10}$ alkyl, $C_2$–$C_{10}$ alkenyl, $C_2$–$C_{10}$ alkynyl or $C_3$–$C_8$ cycloalkyl is each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^7$, —SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^7$, —$NR^6R^7$, —$CONR^6R^7$, aryl and heterocyclyl;

$R^2$ is H, $C_1$–$C_4$ alkyl, $C_2$–$C_4$ alkenyl, $C_2$–$C_4$ alkynyl, $C_3$–$C_6$ cycloalkyl, halo, —CN, $C_1$–$C_4$ haloalkyl, —$NR^9R^{10}$, —$NR^9COR^{10}$, —$NR^9CO_2R^{10}$, —$OR^{11}$, —SH or —$S(O)_nR^{12}$;

$R^3$ is $C_1$–$C_{10}$ alkyl, $C_2$–$C_{10}$ alkenyl, $C_2$–$C_{10}$ alkynyl, $C_3$–$C_8$ cycloalkyl, $C_1$–$C_4$ haloalkyl, aryl, heterocyclyl, —CN, —$OR^7$, —$S(O)_2R^{13}$, —$COR^7$, —$CO_2R^7$, —$NR^8COR^7$, —$N(COR^7)_2$, —$NR^8CONR^6R^7$, —$CONR^6R^7$, —$NR^8CO_2R^7$, or —$NR^6R^7$, wherein $C_1$–$C_{10}$ alkyl, $C_2$–$C_{10}$ alkenyl, $C_2$–$C_{10}$ alkynyl or $C_3$–$C_8$ cycloalkyl is each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^7$, —$S(O)_nR^{13}$, —$COR^7$, —$CO_2R^7$, —$NR^8COR^7$, —$N(COR^7)_2$, —$NR^8CONR^6R^7$, —$NR^8CO_2R^7$, —$NR^6R^7$, —$CONR^6R^7$, aryl and heterocyclyl, with the proviso that when $R^3$ is aryl, Ar is not imidazolyl;

$R^4$ is H, $C_1$–$C_6$ alkyl, $C_2$–$C_6$ alkenyl or $C_2$–$C_6$ alkynyl, wherein $C_2$–$C_6$ alkenyl or $C_2$–$C_6$ alkynyl is optionally substituted with $C_1$–$C_4$ alkyl or $C_3$–$C_6$ cycloalkyl and wherein $C_1$–$C_6$ alkyl is optionally substituted with $C_1$–$C_4$ alkyl, $C_3$–$C_6$ cycloalkyl, $C_1$–$C_4$ haloalkyl, —$OR^7$, —$S(O)_nR^{12}$, —$CO_2R^7$, —$NR^6R^7$ or —$NR^9COR^{10}$;

$R^5$ is independently selected at each occurrence from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, aryl, heterocyclyl, —$NO_2$, halo, —CN, $C_1$–$C_4$ haloalkyl, —$NR^6R^7$, —$NR^8COR^7$, —$NR^8CO_2R^7$, —$OR^7$, —$COR^7$, —$CO_2R^7$, —$CONR^6R^7$, —$CON(OR^9)R^7$, —SH, and —$S(O)_nR^{13}$, wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are substituted with 0 to 3 substituents independently selected at each occurrence from $C_1$–$C_4$ alkyl, —$NO_2$, halo, —CN, —$OR^7$, —$COR^7$, —$CO_2R^7$, —$CONR^6R^7$, —$NR^6R^7$, —$NR^8COR^7$, —$NR^8CO_2R^7$ and —$S(O)_nR^{13}$;

$R^6$ and $R^7$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heterocyclyl, heterocyclyl($C_1$–$C_4$ alkyl)-, morpholinoethyl, morpholinopropyl and morpholinobutyl; or —$NR^6R^7$ taken together as a whole is piperidine, pyrrolidine, piperazine, N-methyl-piperazine, morpholine or thiomorpholine;

wherein $C_1$–$C_4$ alkyl, may be substituted with 0 to 2 substituents independently selected at each occurrence from —OH or $C_1$–$C_4$ alkoxy groups;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl, $C_1$–$C_4$ haloalkyl or —$NR^6R^7$;

$R^{13}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^6R^7$, aryl, aryl($C_1$–$C_4$ alkyl)-, heterocyclyl or heterocyclyl ($C_1$–$C_4$ alkyl)-;

$R^{14}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^{15}R^{16}$;

$R^{15}$ and $R^{16}$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl and $C_4$–$C_{12}$ cycloalkylalkyl; or —$NR^{15}R^{16}$ taken together as a whole is piperidine, pyrrolidine, piperazine, N-methylpiperazine, morpholine or thiomorpholine;

aryl is phenyl, biphenyl or naphthyl, each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^{15}$, —SH, —$S(O)_nR^{14}$, —$COR^{15}$, —$CO_2R^{15}$, —$OC(O)R^{14}$, —$NO_2$, —$NR^8COR^{15}$, —$N(COR^{15})_2$, —$NR^8CONR^{15}R^{16}$, —$NR^8CO_2R^{15}$, —$NR^{15}R^{16}$ and —$CONR^{15}R^{16}$;

heterocyclyl is 5- to 10-membered heterocyclic ring which may be saturated, partially unsaturated or aromatic, and which consists of carbon atoms and from 1 to 4 heteroatoms independently selected from the group consisting of N, O and S, wherein the heterocyclic ring is substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^{15}$, —SH, —$S(O)_nR^{14}$, —$COR^{15}$, —$CO_2R^{15}$, —OC(O)R$^{14}$, —NR$^8$COR$^{15}$, —N(COR$^{15}$)$_2$, —NR$^8$CONR$^{15}$R$^{16}$, —NR$^8$CO$_2$R$^{15}$, —NR$^{15}$R$^{16}$, and —CONR$^{15}$R$^{16}$; and n is independently at each occurrence 0, 1 or 2; and wherein, when Z is N:

Y is NR$^4$, O or S(O)$_n$;

Ar, R$^1$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, aryl, heterocyclyl, heterocyclyl and n are as defined above, but R$^3$ is C$_1$–C$_{10}$ alkyl, C$_2$–C$_{10}$ alkenyl, C$_2$–C$_{10}$ alkynyl, C$_3$–C$_8$ cycloalkyl, C$_1$–C$_4$ haloalkyl, aryl, heterocyclyl, —CN, —S(O)$_2$R$^{13}$, —CO$_2$R$^7$, —COR$^7$ or —CONR$^6$R$^7$, wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^7$, —S(O)$_n$R$^{13}$, —COR$^7$, —CO$_2$R$^7$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl, with the proviso that when R$^3$ is aryl, Ar is not imidazolyl.

[3] Preferred compounds of this invention are compounds of Formula (I) and pharmaceutically acceptable salts and pro-drug forms thereof, wherein:

Z is CR$^2$;

Y is NR$^4$ or O;

Ar is phenyl or pyridyl, each substituted with 0 to 4 R$^5$ groups;

R$^1$ is H, halo, C$_1$–C$_4$ alkyl, cyclopropyl, C$_1$–C$_4$ haloalkyl, —CN, —NR$^6$R$^7$, —CONR$^6$R$^7$, —OR$^7$, —COR$^7$, —CO$_2$R$^7$ or —S(O)$_n$R$^{13}$, wherein C$_1$–C$_4$ alkyl is substituted with 0 to 3 substituents independently selected at each occurrence from C$_1$–C$_4$ alkyl, C$_3$–C$_6$ cycloalkyl, halo, —CN, —OR$^7$, —S(O)$_n$R$^{13}$, —COR$^7$, —CO$_2$R$^7$, —NR$^8$COR$^7$, —NR$^8$CO$_2$R$^7$, —NR$^6$R$^7$ and aryl;

R$^2$ is H, C$_1$–C$_4$ alkyl, halo, C$_1$–C$_4$ haloalkyl;

R$^3$ is C$_1$–C$_{10}$ alkyl, C$_2$–C$_{10}$ alkenyl, C$_2$–C$_{10}$ alkynyl, C$_3$–C$_8$ cycloalkyl, C$_1$–C$_4$ haloalkyl, aryl, heterocyclyl, —CN, —OR$^7$, —S(O)$_2$R$^{13}$, —COR$^7$, —CO$_2$R$^7$, —NR$^8$COR$^7$, —N(COR$^7$)$_2$, —NR$^8$CONR$^6$R$^7$, —CONR$^6$R$^7$, —NR$^8$CO$_2$R$^7$, or —NR$^6$R$^7$, wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, C$_1$–C$_4$ haloalkyl, halo, —CN, —OR$^7$, —S(O)$_n$R$^{13}$, —CO$_2$R$^7$, —NR$^8$COR$^7$, —NR$^8$CONR$^6$R$^7$, —NR$^8$CO$_2$R$^7$, —NR$^6$R$^7$, aryl and heterocyclyl;

R$^4$ is H, C$_1$–C$_6$ alkyl or C$_2$–C$_6$ alkenyl, wherein C$_1$–C$_6$ alkyl is optionally substituted with C$_1$–C$_4$ alkyl, C$_1$–C$_4$ haloalkyl, —OR$^7$, —S(O)$_n$R$^{12}$, —CO$_2$R$^7$, —NR$^6$R$^7$ or —NR$^9$COR$^{10}$;

R$^5$ is independently selected at each occurrence from C$_1$–C$_6$ alkyl, C$_2$–C$_6$ alkenyl, C$_2$–C$_6$ alkynyl, C$_3$–C$_6$ cycloalkyl, C$_4$–C$_8$ cycloalkylalkyl, aryl, heterocyclyl, C$_1$–C$_4$ haloalkyl, halo, —CN, —NO$_2$, —NR$^6$R$^7$, —COR$^7$, —OR$^7$, —CONR$^6$R$^7$, —CON(OR$^9$)R$^7$, CO$_2$R$^7$ and —S(O)$_n$R$^{13}$, wherein C$_1$–C$_6$ alkyl, C$_2$–C$_6$ alkenyl, C$_2$–C$_6$ alkynyl, C$_3$–C$_6$ cycloalkyl and C$_4$–C$_8$ cycloalkylalkyl are substituted with 0 to 3 substituents independently selected at each occurrence from C$_1$–C$_4$ alkyl, —NO$_2$, halo, —CN, —NR$^6$R$^7$, COR$^7$, —OR$^7$, —CONR$^6$R$^7$, CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heterocyclyl, heterocyclyl(C$_1$–C$_4$ alkyl)-, morpholinoethyl, morpholinopropyl and morpholinobutyl; or —NR$^6$R$^7$ taken together as a whole is piperidine, pyrrolidine, piperazine, N-methylpiperazine, morpholine or thiomorpholine;

wherein C$_1$–C$_4$ alkyl, may be substituted with 0 to 2 substituents independently selected at each occurrence from —OH or C$_1$–C$_4$ alkoxy groups;

R$^8$ is independently at each occurrence H or C$_1$–C$_4$ alkyl;

R$^9$ and R$^{10}$ are independently at each occurrence selected from H, C$_1$–C$_4$ alkyl and C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl, C$_1$–C$_4$ haloalkyl or —NR$^6$R$^7$;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^6$R$^7$, aryl, aryl(C$_1$–C$_4$ alkyl)-, heterocyclyl or heterocyclyl (C$_1$–C$_4$ alkyl)-;

R$^{14}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^{15}$R$^{16}$;

R$^{15}$ and R$^{16}$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl and C$_4$–C$_{12}$ cycloalkylalkyl; or —NR$^{15}$R$^{16}$ taken together as a whole is piperidine, pyrrolidine, piperazine, N-methylpiperazine, morpholine or thiomorpholine;

aryl is phenyl substituted with 0 to 3 substituents independently selected at each occurrence from C$_1$–C$_4$ alkyl, halo, —CN, —OR$^{15}$, —S(O)$_n$R$^{14}$, —COR$^{15}$, —CO$_2$R$^{15}$, —NO$_2$, —NR$^8$COR$^{15}$, —NR$^8$CONR$^{15}$R$^{16}$, —NR$^8$CO$_2$R$^{15}$ and —NR$^{15}$R$^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from C$_1$–C$_4$ alkyl, halo, —CN, —OR$^{15}$, —S(O)$_n$R$^{14}$, —CO$_2$R$^{15}$, —NO$_2$, —NR$^8$COR$^{15}$, —NR$^8$CONR$^{15}$R$^{16}$, —NR$^8$CO$_2$R$^{15}$, and —NR$^{15}$R$^{16}$; and n is independently at each occurrence 0, 1 or 2.

[4] More preferred compounds of this invention are compounds of Formula (I) and pharmaceutically acceptable salts and pro-drug forms thereof, wherein:

Z is CR$^2$;

Y is NR$^4$;

Ar is phenyl or pyridyl, each substituted with 0 to 4 R$^5$ groups;

R$^1$ is H, halo, C$_1$–C$_4$ alkyl, cyclopropyl, C$_1$–C$_3$ haloalkyl, —CN, —NR$^6$R$^7$, —CONR$^6$R$^7$, —COR$^7$, —CO$_2$R$^7$, —OR$^7$ or —S(O)$_n$R$^{13}$ wherein C$_1$–C$_4$ alkyl is substituted with 0 to 3 substituents independently selected at each occurrence from C$_3$–C$_4$ cycloalkyl, halo, —CN, —OR$^7$, —S(O)$_n$R$^{13}$, —COR$^7$, —CO$_2$R$^7$, —NR$^6$R$^7$;

R$^2$ is H;

R$^3$ is C$_1$–C$_6$ alkyl, C$_2$–C$_6$ alkenyl, C$_2$–C$_6$ alkynyl, C$_3$–C$_6$ cycloalkyl, C$_1$–C$_4$ haloalkyl or aryl, wherein C$_1$–C$_6$ alkyl, C$_2$–C$_6$ alkenyl, C$_2$–C$_6$ alkynyl or C$_3$–C$_6$ cycloalkyl is each substituted with 0 to 3 substituents independently selected at each occurrence from $C_1$–$C_6$ alkyl, $C_3$–$C_6$ cycloalkyl, $C_1$–$C_4$ haloalkyl, halo, —CN, —$OR^7$, —$S(O)_nR^{13}$, —$CO_2R^7$, —$NR^8COR^7$, —$NR^8CONR^6R^7$, —$NR^8CO_2R^7$, —$NR^6R^7$ and aryl;

$R^4$ is H, allyl, or $C_1$–$C_4$ alkyl, wherein $C_1$–$C_4$ alkyl is optionally substituted with $C_1$–$C_4$ alkyl, —$OR^7$, —$S(O)_2R^{12}$, —$CO_2R^7$, —$NR^6R^7$ or —$NR^9COR^{10}$;

$R^5$ is independently selected at each occurrence from $C_1$–$C_6$ alkyl, aryl, heterocyclyl, $C_1$–$C_4$ haloalkyl, halo, —CN, —$NO_2$, —$NR^6R^7$, —$COR^7$, —$OR^7$, —$CONR^6R^7$, —$CON(OR^9)R^7$, —$CO_2R^7$ and —$S(O)_nR^{13}$, wherein $C_1$–$C_6$ alkyl is substituted with 0 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$ and —$S(O)_nR^{13}$;

$R^6$ and $R^7$ are independently selected at each occurrence from H, $C_1$–$C_4$ alkyl, $C_1$–$C_4$ haloalkyl and $C_2$–$C_8$ alkoxyalkyl;
wherein $C_1$–$C_4$ alkyl, may be substituted with 0 to 2 substituents independently selected at each occurrence from —OH or $C_1$–$C_4$ alkoxy groups;

$R^8$, $R^9$ and $R^{10}$ are independently at each occurrence H or $C_1$–$C_4$ alkyl;

$R^{12}$ and $R^{13}$ are independently at each occurrence $C_1$–$C_4$ alkyl or —$NR^6R^7$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$ and —$NR^{15}R^{16}$; and n is independently at each occurrence 0, 1 or 2.

[5] Even more preferred compounds of this invention are compounds of Formula (I) and pharmaceutically acceptable salts and pro-drug forms thereof, wherein:

Z is $CR^2$;

Y is $NR^4$;

Ar is phenyl or pyridyl, each substituted with 2 to 4 $R^5$ groups;

$R^1$ is H, Cl, Br, methyl, ethyl, cyclopropyl, or —CN, $R^2$ is H;

$R^3$ is $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl or aryl, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_4$ alkyl, $C_3$–$C_6$ cycloalkyl, —$CF_3$, halo, —CN, —$OR^7$, and aryl;

$R^4$ is H, methyl, ethyl, i-propyl, n-propyl, n-butyl, i-butyl, s-butyl, n-butyl, or allyl;

$R^5$ is independently selected at each occurrence from methyl, ethyl, i-propyl, n-propyl, aryl, —$CF_3$, halo, —CN, —$N(CH_3)_2$, —$C(=O)CH_3$, —$OCH_3$, —$OCH_2CH_3$, —$OCF_3$, and —$S(O)_2CH_3$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$ and —$NR^{15}R^{16}$; and n is independently at each occurrence 0, 1 or 2.

[6] Specifically preferred compounds of this invention are compounds of Formula (I), pharmaceutically acceptable salts and pro-drug forms thereof, which are:

3-[(2,4-Dibromophenyl)amino]-5-chloro-1-(1-ethylpropyl)-2(1H)-pyrazinone;

3-[[2-Bromo-4-(1-methylethyl)phenyl]amino]-5-Chloro-1-(1-ethylpropyl)-2(1H)-pyrazinone;

3-[(2,4-Dibromophenyl)ethylamino]-5-Chloro-1-(1-ethylpropyl)-2(1H)-pyrazinone;

3-[[2-Bromo-4-(1-methylethyl)phenyl]ethylamino]-5-chloro-1-(1-ethylpropyl)-2(1H)-pyrazinone;

3-[(2,4,6-Trimethylphenyl)amino]-5-Chloro-1-(1-ethylpropyl)-2(1H)-pyrazinone;

3-[(2,4,6-Trimethylphenyl)ethylamino]-5-Chloro-1-(1-ethylpropyl)-2(1H)-pyrazinone;

(+/−)-3-[(2,4,6-Trimethylphenyl)amino]-5-Chloro-1-[1-(methoxymethyl)propyl]-2(1H)-pyrazinone;

3-[(2-Bromo-4,6-dimethoxyphenyl)amino]-5-Chloro-1-(1-ethylpropyl)-2(1H)-pyrazinone;

3-[(2-Cyano-4,6-dimethylphenyl)amino]-5-Chloro-1-[1-(methoxymethyl)propyl]-2(1H)-pyrazinone;

(+/−)-3-[(2-Bromo-4,6-dimethoxyphenyl)amino]-5-Chloro-1-[1-(methoxymethyl)propyl]-2(1H)-pyrazinone;

(+/−)-3-[(2-Chloro-4,6-dimethoxyphenyl)amino]-5-Chloro-1-[1-(methoxymethyl)propyl]-2 (1H)-pyrazinone;

(+/−)-3-[(4,6-Dimethyl-2-iodophenyl)amino]-5-Chloro-1-[1-(methoxymethyl)propyl]-2(1H)-pyrazinone;

3-[(2-Cyano-4,6-dimethylphenyl)amino]-5-Chloro-1-[1-(methoxymethyl)propyl]-2(1H)-pyrazinone;

(+/−)-3-[(2-Bromo-4,6-dimethylphenyl)amino]-5-Chloro-1-[1-(methoxymethyl)propyl]-2 (1H)-pyrazinone;

(+/−)-3-[(4-Bromo-2,6-dimethylphenyl)amino]-5-Chloro-1-[1-(methoxymethyl)propyl]-2(1H)-pyrazinone;

(+/−)-3-[(4-Acetyl-2,6-dimethylphenyl)amino]-5-Chloro-1-[1-(methoxymethyl)propyl]-2(1H)-pyrazinone;

(+/−)-3-[(2-Acetyl-4,6-dimethylphenyl)amino]-5-Chloro-1-[1-(methoxymethyl)propyl]-2(1H)-pyrazinone;

(+/−)-3-[(4,6-Dimethyl-2-thiomethylphenyl)amino]-5-chloro-1-[1-(methoxymethyl)propyl]-2 (1H)-pyrazinone;

(+/−)-3-[(4,6-Dimethyl-2-methylsulfonylphenyl)amino]-5-chloro-1-[1-(methoxymethyl)propyl]-2(1H)-pyrazinone;

(+/−)-3-[(4-Chloro-2-iodo-6-methylphenyl)amino]-5-chloro-1-[1-(methoxymethyl)propyl]-2(1H)-pyrazinone;

3-[(2,4,6-Trimethylphenyl)amino]-5-Chloro-1-[1-(methoxymethyl)-2-methoxyethyl]-2(1H)-pyrazinone;

3-[(2,4,6-Trimethylphenyl)amino]-5-Chloro-1-phenyl-2 (1H)-pyrazinone;

(+/−)-3-[(2,4-Dibromophenyl)amino]-5-methyl-1-[1-(methoxymethyl)propyl]-2(1H)-pyrazinone;

(+/−)-3-[[2-Bromo-4-(1-methylethyl)phenyl]amino]-5-methyl-1-[1-(methoxymethyl)propyl]-2 (1H)-pyrazinone;

(+/−)-3-[(2,4,6-Trimethylphenyl)amino]-5-methyl-1-[1-(methoxymethyl)propyl]-2(1H)-pyrazinone;

3-[(2,4,6-Trimethylphenyl)amino]-5-methyl-1-[1-(methoxymethyl)-2-methoxyethyl]-2(1H)-pyrazinone;

3-[(2,4-Dichloro-6-methylphenyl)amino]-5-methyl-1-[1-(methoxymethyl)-2-methoxyethyl]-2(1H)-pyrazinone;

3-[(2,4-Dichloro-6-methylphenyl)amino]-5-Chloro-1-[1-(methoxymethyl)-2-methoxyethyl]-2(1H)-pyrazinone;

3-[(2,4-Dibromo-6-methylphenyl)amino]-5-chloro-1-[1-(methoxymethyl)-2-methoxyethyl]-2(1H)-pyrazinone;

(+/−)-3-[(2,4,6-Trimethylphenyl)amino]-5-methyl-1-[1-(methoxymethyl)-3-methoxypropyl]-2(1H)-pyrazinone;

(+/−)-3-[(2,4,6-Trimethylphenyl)amino]-5-Chloro-1-[1-(methoxymethyl)-3-methoxypropyl]-2(1H)-pyrazinone;

3-[(2,4,6-Trimethylphenyl)amino]-5-Chloro-1-[1-(2-methoxyethyl)-3-methoxypropyl]-2(1H)-pyrazinone;

(+/−)-3-[(2,4-Dimethyl-6-methoxyphenyl)amino]-5-Chloro-1-[1-(methoxymethyl)propyl]-2(1H)-pyrazinone;

(+/−)-3-[(2,4-Dimethyl-6-methoxyphenyl)amino]-5-Chloro-1-[1-(methoxymethyl)-3-methoxypropyl]-2(1H)-pyrazinone;

(+/−)-3-[(2,4-Dimethyl-6-methoxyphenyl)amino]-5-methyl-1-[1-(methoxymethyl)-3-methoxypropyl]-2(1H)-pyrazinone;

(+/−)-3-[(4-Bromo-2,6-dimethylphenyl)amino]-5-methyl-1-[1-(methoxymethyl)-3-methoxypropyl]-2(1H)-pyrazinone;

(+/−)-3-[(2-Chloro-4,6-dimethylphenyl)amino]-5-methyl-1-[1-(methoxymethyl)-3-methoxypropyl]-2 (1H)-pyrazinone;

(+/−)-3-[[2,4-Dimethyl-6-(methoxymethyl)phenyl]amino]-5-methyl-1-[1-(methoxymethyl)-3-methoxypropyl]-2(1H)-pyrazinone;

3-[(2,4-Dimethyl-6-methoxyphenyl)amino]-5-methyl-1-[1-(methoxymethyl)-2-methoxyethyl]-2(1H)-pyrazinone;

3-[(4-Bromo-2,6-dimethylphenyl)amino]-5-methyl-1-[1-(methoxymethyl)-2-methoxyethyl]-2(1H)-pyrazinone;

3-[(2-Chloro-4,6-dimethylphenyl)amino]-5-methyl-1-[1-(methoxymethyl)-2-methoxyethyl]-2(1H)-pyrazinone;

3-[[2,4-Dimethyl-6-(methoxymethyl)phenyl]amino]-5-methyl-1-[1-(methoxymethyl)-2-methoxyethyl]-2(1H)-pyrazinone;

(+/−)-3-[(2,4-Dimethyl-6-methoxyphenyl)amino]-5-Chloro-1-[1-(methoxymethyl)-3-methoxypropyl]-2(1H)-pyrazinone;

(+/−)-3-[(4-Bromo-2,6-dimethylphenyl)amino]-5-Chloro-1-[1-(methoxymethyl)-3-methoxypropyl]-2(1H)-pyrazinone;

(+/−)-3-[(2-Chloro-4,6-dimethylphenyl)amino]-5-Chloro-1-[1-(methoxymethyl)-3-methoxypropyl]-2(1H)-pyrazinone;

(+/−)-3-[[2,4-Dimethyl-6-(methoxymethyl)phenyl]amino]-5-Chloro-1-[1-(methoxymethyl)-3-methoxypropyl]-2 (1H)-pyrazinone;

3-[(2,4-Dimethyl-6-methoxyphenyl)amino]-5-Chloro-1-[1-(methoxymethyl)-2-methoxyethyl]-2(1H)-pyrazinone;

3-[(4-Bromo-2,6-dimethylphenyl)amino]-5-Chloro-1-[1-(methoxymethyl)-2-methoxyethyl]-2(1H)-pyrazinone;

3-[(2-Chloro-4,6-dimethylphenyl)amino]-5-Chloro-1-[1-(methoxymethyl)-2-methoxyethyl]-2(1H)-pyrazinone;

3-[[2,4-Dimethyl-6-(methoxymethyl)phenyl]amino]-5-chloro-1-[1-(methoxymethyl)-2-methoxyethyl]-2(1H)-pyrazinone;

(+/−)3-[(2,4-Dimethyl-6-methoxyphenyl)amino]-5-Chloro-1-(2-methoxy-1-methylethyl)-2(1H)-pyrazinone;

(+/−)3-[(4-Bromo-2,6-dimethylphenyl)amino]-5-Chloro-1-(2-methoxy-1-methylethyl)-2(1H)-pyrazinone;

(+/−)3-[(4-Bromo-2,6-dimethylphenyl)amino]-5-Chloro-1-[1-(ethoxymethyl)propyl]-2(1H)-pyrazinone;

(+/−)3-[(4-Bromo-2,6-dimethylphenyl)amino]-5-Chloro-1-(2-ethoxy-1-methylethyl)-2(1H)-pyrazinone; and (+/−)3-[(4-Bromo-2,6-difluorophenyl)amino]-5-Chloro-1-[1-(methoxymethyl)propyl]-2(1H)-pyrazinone;

(+/−)-3-[(2-Bromo-4,6-dimethylphenyl)amino]-5-methyl-1-[1-(methoxymethyl)-3-methoxypropyl]-2(1H)-pyrazinone;

(+/−)-3-[(2,4-Dimethyl-6-thiomethylphenyl)amino]-5-methyl-1-[1-(methoxymethyl)-3-methoxypropyl]-2(1H)-pyrazinone;

(+/−)-3-[(2,4-Dimethyl-6-methylsulfonylphenyl)amino]-5-methyl-1-[1-(methoxymethyl)-3-methoxypropyl]-2(1H)-pyrazinone;

(+/−)-3-[(2,6-Dimethyl-4-(N,N-dimethylamino)phenyl)-amino]-5-methyl-1-[1-(methoxymethyl)-3-methoxypropyl]-2(1H)-pyrazinone;

(+/−)-3-[(2,4-Dichloro-6-methylphenyl)amino]-5-methyl-1-[1-(methoxymethyl)-3-methoxypropyl]-2(1H)-pyrazinone;

(+/−)-3-[(4-Chloro-2,6-dimethylphenyl)amino]-5-methyl-1-[1-(methoxymethyl)-3-methoxypropyl]-2(1H)-pyrazinone;

(+/−)-3-[(2,6-Dimethyl-4-thiomethylphenyl)amino]-5-methyl-1-[1-(methoxymethyl)-3-methoxypropyl]-2(1H)-pyrazinone;

(+/−)-3-[(2,6-Dimethyl-4-methoxyphenyl)amino]-5-methyl-1-[1-(methoxymethyl)-3-methoxypropyl]-2(1H)-pyrazinone;

(+/−)-3-[(2,6-Dimethyl-4-methylsulfonylphenyl)amino]-5-methyl-1-[1-(methoxymethyl)-3-methoxypropyl]-2(1H)-pyrazinone;

(+/−)-3-[(4-Acetyl-2,6-dimethylphenyl)amino]-5-methyl-1-[1-(methoxymethyl)-3-methoxypropyl]-2(1H)-pyrazinone;

3-[(4-Bromo-2,6-dimethylphenyl)amino]-5-methyl-1-[1-(methoxymethyl)-2-methoxyethyl]-2(1H)-pyrazinone;

3-[(4-Acetyl-2,6-dimethylphenyl)amino]-5-methyl-1-[1-(methoxymethyl)-2-methoxyethyl]-2(1H)-pyrazinone;

3-[(2,6-Dimethyl-4-thiomethylphenyl)amino]-5-methyl-1-[1-(methoxymethyl)-2-methoxyethyl]-2(1H)-pyrazinone;

3-[(2,6-Dimethyl-4-methylsulfonylphenyl)amino]-5-methyl-1-[1-(methoxymethyl)-2-methoxyethyl]-2(1H)-pyrazinone;

3-[(2,6-Dimethyl-4-(N,N-dimethylamino)phenyl)amino]-5-methyl-1-[1-(methoxymethyl)-2-methoxyethyl]-2(1H)-pyrazinone;

3-[(4,6-Dimethyl-2-(N,N-dimethylamino)phenyl)amino]-5-methyl-1-[1-(methoxymethyl)-2-methoxyethyl]-2(1H)-pyrazinone;

(+/−)3-[(2,6-Dimethyl-4-thiomethylphenyl)amino]-5-chloro-1-[1-(methoxymethyl)propyl]-2(1H)-pyrazinone;

(+/−)3-[(2,6-Dimethyl-4-methylsulfonylphenyl)amino]-5-chloro-1-[1-(methoxymethyl)propyl]-2(1H)-pyrazinone;

(+/−)3-[(2-Chloro-4,6-dimethylphenyl)amino]-5-Chloro-1-[1-(methoxymethyl)propyl]-2(1H)-pyrazinone;

(+/−)3-[(4-Bromo-6-methoxy-2-methylphenyl)amino]-5-chloro-1-[1-(methoxymethyl)propyl]-2(1H)-pyrazinone;

3-[(2,6-Dimethyl-4-thiomethylphenyl)amino]-5-Chloro-1-[1-(methoxymethyl)-2-methoxyethyl]-2(1H)-pyrazinone;

3-[(2,6-Dimethyl-4-methylsulfonylphenyl)amino]-5-chloro-1-[1-(methoxymethyl)-2-methoxyethyl]-2(1H)-pyrazinone;

3-[(4-Bromo-6-methoxy-2-methylphenyl)amino]-5-Chloro-1-[1-(methoxymethyl)-2-methoxyethyl]-2(1H)-pyrazinone; and 3-[(2,4,6-Trimethylphenyl)amino]-5-methyl-1-(1-ethylpropyl)-2(1H)-pyrazinone.

[7] A second embodiment of preferred compounds of this invention are compounds of Formula (I) and pharmaceutically acceptable salts and pro-drug forms thereof, wherein:

Z is $CR^2$;

Y is $NR^4$ or O;

Ar is phenyl or pyridyl, each substituted with 0 to 4 $R^5$ groups;

$R^1$ is H, halo, $C_1$–$C_{10}$ alkyl, $C_2$–$C_{10}$ alkenyl, $C_2$–$C_{10}$ alkynyl, $C_3$–$C_8$ cycloalkyl, $C_1$–$C_4$ haloalkyl, aryl, heterocyclyl, —CN, —OR$^7$, —SH, —S(O)$_n$R$^{13}$, —COR$^7$, —CONR$^6$R$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, or —NR$^6$R$^7$, wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^7$, —SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl;

R$^2$ is H, C$_1$–C$_4$ alkyl, halo, C$_1$–C$_4$ haloalkyl;

R$^3$ is C$_1$–C$_4$ alkyl, C$_3$–C$_6$ cycloalkyl, C$_1$–C$_4$ haloalkyl and —NR$^6$R$^7$, wherein C$_1$–C$_4$ alkyl is substituted with 0 to 3 substituents independently selected at each occurrence from C$_1$–C$_4$ alkyl, C$_3$–C$_6$ cycloalkyl, C$_1$–C$_4$ haloalkyl, halo, —CN, —OR$^7$, —S(O)$_n$R$^{13}$, —COR$^7$, —CO$_2$R$^7$, —NR$^8$COR$^7$, —N(COR$^7$)$_2$, —NR$^8$CONR$^6$R$^7$, —NR$^8$CO$_2$R$^7$, —NR$^6$R$^7$ and —CONR$^6$R$^7$;

R$^4$ is H, C$_1$–C$_6$ alkyl or C$_2$–C$_6$ alkenyl, wherein C$_1$–C$_6$ alkyl is optionally substituted with C$_1$–C$_4$ alkyl, C$_1$–C$_4$ haloalkyl, —OR$^7$, —S(O)$_n$R$^{12}$, —CO$_2$R$^7$, —NR$^6$R$^7$ or —NR$^9$COR$^{10}$;

R$^5$ is independently selected at each occurrence from C$_1$–C$_{10}$ alkyl, C$_2$–C$_{10}$ alkenyl, C$_2$–C$_{10}$ alkynyl, C$_3$–C$_6$ cycloalkyl, C$_4$–C$_{12}$ cycloalkylalkyl, aryl, heterocyclyl, —NO$_2$, halo, —CN, C$_1$–C$_4$ haloalkyl, —NR$^6$R$^7$, —NR$^8$COR$^7$, —NR$^8$CO$_2$R$^7$, —OR$^7$, —COR$^7$, —CO$_2$R$^7$, —CONR$^6$R$^7$, —CON(OR$^9$)R$^7$ and —S(O)$_n$R$^{13}$, wherein C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are substituted with 0 to 3 substituents independently selected at each occurrence from C$_1$–C$_4$ alkyl, —NO$_2$, halo, —CN, —OR$^7$, —COR$^7$, —CO$_2$R$^7$, —CONR$^6$R$^7$, —NR$^6$R$^7$, —NR$^8$COR$^7$, —NR$^8$CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heterocyclyl, heterocyclyl (C$_1$–C$_4$ alkyl)-, morpholinoethyl, morpholinopropyl and morpholinobutyl; or —NR$^6$R$^7$ taken together as a whole is piperidine, pyrrolidine, piperazine, N-methyl-piperazine, morpholine or thiomorpholine;

wherein C$_1$–C$_4$ alkyl, may be substituted with 0 to 2 substituents independently selected at each occurrence from —OH or C$_1$–C$_4$ alkoxy groups;

R$^8$ is independently at each occurrence H or C$_1$–C$_4$ alkyl;

R$^9$ and R$^{10}$ are independently at each occurrence selected from H, C$_1$–C$_4$ alkyl and C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl, C$_1$–C$_4$ haloalkyl or —NR$^6$R$^7$;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^6$R$^7$, aryl, aryl(C$_1$–C$_4$ alkyl)-, heterocyclyl or heterocyclyl (C$_1$–C$_4$ alkyl)-;

R$^{14}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^{15}$R$^{16}$;

R$^{15}$ and R$^{16}$ are independently at each occurrence from H, C$_1$–C$_4$ alkyl, C$_1$–C$_4$ haloalkyl, C$_2$–C$_8$ alkoxyalkyl, C$_3$–C$_6$ cycloalkyl and C$_4$–C$_{12}$ cycloalkylalkyl; or —NR$^{15}$R$^{16}$ taken together as a whole is piperidine, pyrrolidine, piperazine, N-methyl-piperazine, morpholine or thiomorpholine;

aryl is phenyl or naphthyl, each substituted with 0 to 3 substituents independently selected at each occurrence from C$_1$–C$_4$ alkyl, halo, —CN, —OR$^{15}$, —S(O)$_n$R$^{14}$, —COR$^{15}$, —CO$_2$R$^{15}$, —NO$_2$, —NR$^8$COR$^{15}$, —NR$^8$CONR$^{15}$R$^{16}$, —NR$^8$CO$_2$R$^{15}$ and —NR$^{15}$R$^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from C$_1$–C$_4$ alkyl, halo, —CN, —OR$^{15}$, —S(O)$_n$R$^{14}$, —CO$_2$R$^{15}$, —NO$_2$, —NR$^8$COR$^{15}$, —NR$^8$CONR$^{15}$R$^{16}$, —NR$^8$CO$_2$R$^{15}$, and —NR$^{15}$R$^{16}$; and n is independently at each occurrence 0, 1 or 2.

[8] More preferred compounds of the second embodiment of this invention are compounds of Formula (I) and pharmaceutically acceptable salts and pro-drug forms thereof, wherein:

Z is CR$^2$;

Y is NR$^4$;

Ar is phenyl or pyridyl, each substituted with 0 to 4 R$^5$ groups;

R$^1$ is H, halo, C$_1$–C$_6$ alkyl, C$_2$–C$_6$ alkenyl, C$_2$–C$_6$ alkynyl, C$_3$–C$_6$ cycloalkyl, C$_1$–C$_4$ haloalkyl, aryl, heterocyclyl, —CN, —OR$^7$, —S(O)$_n$R$^{13}$, —COR$^7$, —CONR$^6$R$^7$, —CO$_2$R$^7$ or —NR$^6$R$^7$, wherein C$_1$–C$_6$ alkyl, C$_2$–C$_6$ alkenyl, C$_2$–C$_6$ alkynyl or C$_3$–C$_6$ cycloalkyl is each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^7$, —SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl;

R$^2$ is H;

R$^3$ is C$_1$–C$_4$ alkyl, C$_3$–C$_6$ cycloalkyl, C$_1$–C$_4$ haloalkyl and —NR$^6$R$^7$$_1$, wherein C$_1$–C$_4$ alkyl is substituted with 0 to 3 substituents independently selected at each occurrence from C$_3$–C$_6$ cycloalkyl, C$_1$–C$_4$ haloalkyl, halo, —CN, —OR$^7$, —S(O)$_n$R$^{13}$, —COR$^7$, —CO$_2$R$^7$, —NR$^8$COR$^7$, —N(COR$^7$)$_2$, —NR$^8$CONR$^6$R$^7$, —NR$^8$CO$_2$R$^7$, —NR$^6$R$^7$ and —CONR$^6$R$^7$;

R$^4$ is H, allyl, or C$_1$–C$_4$ alkyl, wherein C$_1$–C$_4$ alkyl is optionally substituted with C$_1$–C$_4$ alkyl, —OR$^7$, —S(O)$_2$R$^{12}$, —CO$_2$R$^7$, —NR$^6$R$^7$ or —NR$^9$COR$^{10}$;

R$^5$ is independently selected at each occurrence from C$_1$–C$_6$ alkyl, aryl, heterocyclyl, C$_1$–C$_4$ haloalkyl, halo, —CN, —NO$_2$, —NR$^6$R$^7$, —COR$^7$, —OR$^7$, —CONR$^6$R$^7$, —CON(OR$^9$)R$^7$, —CO$_2$R$^7$ and —S(O)$_n$R$^{13}$, wherein C$_1$–C$_6$ alkyl is substituted with 0 to 3 substituents independently selected at each occurrence from C$_1$–C$_4$ alkyl, —NO$_2$, halo, —CN, —NR$^6$R$^7$, COR$^7$, —OR$^7$, —CONR$^6$R$^7$, CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl and C$_2$–C$_8$ alkoxyalkyl;

wherein C$_1$–C$_4$ alkyl, may be substituted with 0 to 2 substituents independently selected at each occurrence from —OH or C$_1$–C$_4$ alkoxy groups;

R$^8$, R$^9$ and R$^{10}$ are independently at each occurrence H or C$_1$–C$_4$ alkyl;

$R^{12}$ and $R^{13}$ are independently at each occurrence $C_1$–$C_4$ alkyl or —$NR^6R^7$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$ and —$NR^{15}R^{16}$; and n is independently at each occurrence 0, 1 or 2.

[10] A third embodiment of preferred compounds of this invention are compounds of Formula (I) and pharmaceutically acceptable salts and pro-drug forms thereof, wherein:

Z is N;

Y is $NR^4$ or O;

Ar is phenyl or pyridyl, each substituted with 0 to 4 $R^5$ groups;

$R^1$ is H, halo, $C_1$–$C_4$ alkyl, $C_3$–$C_6$ cycloalkyl, aryl, —CN, $C_1$–$C_4$ haloalkyl, —$NR^6R^7$, —$CONR^6R^7$, —$OR^7$, —$COR^7$, —$CO_2R^7$ or —$S(O)_nR^{13}$, wherein $C_1$–$C_4$ alkyl is substituted with 0 to 3 substituents independently selected at each occurrence from $C_1$–$C_3$ alkyl, $C_3$–$C_6$ cycloalkyl, halo, —CN, —$OR^7$, —$S(O)_nR^{13}$, —$COR^7$, —$CO_2R^7$, —$NR^8COR^7$, —$NR^8CO_2R^7$, —$NR^6R^7$ and aryl;

$R^3$ is $C_1$–$C_{10}$ alkyl, $C_2$–$C_{10}$ alkenyl, $C_2$–$C_{10}$ alkynyl, $C_3$–$C_8$ cycloalkyl, $C_1$–$C_4$ haloalkyl, aryl, heterocyclyl, —CN, —$S(O)_2R^{13}$, —$COR^7$, —$CO_2R^7$ or —$CONR^6R^7$, wherein $C_1$–$C_{10}$ alkyl, $C_2$–$C_{10}$ alkenyl, $C_2$–$C_{10}$ alkynyl or $C_3$–$C_8$ cycloalkyl is each substituted with 0 to 3 substituents independently selected at each occurrence from $C_1$–$C_6$ alkyl, $C_3$–$C_6$ cycloalkyl, $C_1$–$C_4$ haloalkyl, halo, —CN, —$OR^7$, —$S(O)_nR^{13}$, —$CO_2R^7$, —$NR^8COR^7$, —$NR^8CONR^6R^7$, —$NR^8CO_2R^7$, —$NR^6R^7$, aryl and heterocyclyl;

$R^4$ is H, $C_1$–$C_6$ alkyl or $C_2$–$C_6$ alkenyl, wherein $C_1$–$C_6$ alkyl is optionally substituted with $C_1$–$C_4$ alkyl, $C_3$–$C_6$ cycloalkyl, $C_1$–$C_4$ haloalkyl, —$OR^7$, —$S(O)_nR^{12}$, —$CO_2R^7$, —$NR^6R^7$ or —$NR^9COR^{10}$;

$R^5$ is independently selected at each occurrence from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, aryl, heterocyclyl, $C_1$–$C_4$ haloalkyl, halo, —CN, —$NO_2$, —$NR^6R^7$, —$COR^7$, —$OR^7$, —$CONR^6R^7$, —$CON(OR^9)R^7$, $CO_2R^7$ and —$S(O)_nR^{13}$, wherein $C_1$–$C_6$ alkyl, $C_2$–$C_6$ alkenyl, $C_2$–$C_6$ alkynyl, $C_3$–$C_6$ cycloalkyl and $C_4$–$C_8$ cycloalkylalkyl are substituted with 0 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$ and —$S(O)_nR^{13}$;

$R^6$ and $R^7$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heterocyclyl, heterocyclyl($C_1$–$C_4$ alkyl)-, morpholinoethyl, morpholinopropyl and morpholinobutyl; or —$NR^6R^7$ taken together as a whole is piperidine, pyrrolidine, piperazine, N-methylpiperazine, morpholine or thiomorpholine;

wherein $C_1$–$C_4$ alkyl, may be substituted with 0 to 2 substituents independently selected at each occurrence from —OH or $C_1$–$C_4$ alkoxy groups;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl, $C_1$–$C_4$ haloalkyl or —$NR^6R^7$;

$R^{13}$ is $C_1$–$C_4$ alkyl, $C_1$14 $C_4$ haloalkyl, $C_2$–$C_8$ alkoxyalkyl, $C_3$–$C_6$ cycloalkyl, $C_4$–$C_{12}$ cycloalkylalkyl, —$NR^6R^7$, aryl, aryl($C_1$–$C_4$ alkyl)-, heterocyclyl or heterocyclyl($C_1$–$C_4$ alkyl)-;

$R^{14}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^{15}R^{16}$;

$R^{15}$ and $R^{16}$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl and $C_4$–$C_{12}$ cycloalkylalkyl; or —$NR^{15}R^{16}$ taken together as a whole is piperidine, pyrrolidine, piperazine, N-methylpiperazine, morpholine or thiomorpholine;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$, —$NR^8COR^{15}$, —$NR^8CONR^{15}R^{16}$, —$NR^8CO_2R^{15}$ and —$NR^{15}R^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from $C_1$–$C_4$ alkyl, halo, —CN, —$OR^{15}$, —$S(O)_nR^{14}$, —$CO_2R^{15}$, —$NO_2$, —$NR^8COR^{15}$, —$NR^8CONR^{15}R^{16}$, —$NR^8CO_2R^{15}$ and —$NR^{15}R^{16}$; and n is independently at each occurrence 0, 1 or 2.

[11] More preferred compounds of the third embodiment of this invention are compounds of Formula (I) and pharmaceutically acceptable salts and pro-drug forms thereof, wherein:

Z is N;

Y is $NR^4$;

Ar is phenyl or pyridyl, each substituted with 0 to 4 $R^5$ groups;

$R^1$ is H, halo, $C_1$–$C_4$ alkyl, $C_1$–$C_3$ haloalkyl, cyclopropyl, —CN, —$NR^6R^7$, —$CONR^6R^7$, —$COR^7$, —$CO_2R^7$, —$OR^7$ or —$S(O)_nR^{13}$, wherein $C_1$–$C_4$ alkyl is substituted with 0 to 3 substituents independently selected at each occurrence from $C_3$–$C_4$ cycloalkyl, halo, —CN, —$OR^7$, —$S(O)_nR^{13}$, —$COR^7$, —$CO_2R^7$, —$NR^6R^7$;

$R^3$ is $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl or aryl, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_6$ alkyl, $C_3$–$C_6$ cycloalkyl, $C_1$–$C_4$ haloalkyl, halo, —CN, —$OR^7$, —$S(O)_nR^{13}$, —$CO_2R^7$, —$NR^8COR^7$, —$NR^8CONR^6R^7$, —$NR^8CO_2R^7$, —$NR^6R^7$ and aryl;

$R^4$ is H, allyl, or $C_1$–$C_4$ alkyl, wherein $C_1$–$C_4$ alkyl is optionally substituted with $C_1$–$C_4$ alkyl, —$OR^7$, —$S(O)_2R^{12}$, $CO_2R^7$, —$NR^6R^7$ or —$NR^9COR^{10}$;

$R^5$ is independently selected at each occurrence from $C_1$–$C_6$ alkyl, aryl, heterocyclyl, $C_1$–$C_4$ haloalkyl, halo, —CN, —$NO_2$, —$NR^6R^7$, —$COR^7$, —$OR^7$, —$CONR^6R^7$, —$CON(OR^9)R^7$, —$CO_2R^7$ and —S(O)

$_n$R$^{13}$, wherein C$_1$–C$_6$ alkyl is substituted with 0 to 3 substituents independently selected at each occurrence from C$_1$–C$_4$ alkyl, —NO$_2$, halo, —CN, —NR$^6$R$^7$, COR$^7$, —OR$^7$, —CONR$^6$R$^7$, CO$_2$R$^7$ and —S(O)$_n$R$^{13}$;

R$^6$ and R7 are independently selected at each occurrence from H, C$_1$–C$_4$ alkyl, C$_1$–C$_4$ haloalkyl and C$_2$–C$_8$ alkoxyalkyl;
  wherein C$_1$–C$_4$ alkyl, may be substituted with 0 to 2 substituents independently selected at each occurrence from —OH or C$_1$–C$_4$ alkoxy groups;

R$^8$, R$^9$ and R$^{10}$ are independently at each occurrence H or C$_1$–C$_4$ alkyl;

R$^{12}$ and R$^{13}$ are independently at each occurrence C$_1$–C$_4$ alkyl or —NR$^6$R$^7$;

R$^{14}$ is C$_1$–C$_4$ alkyl or —NR$^{15}$R$^{16}$;

R$^{15}$ and R$^{16}$ are independently at each occurrence H, C$_1$–C$_4$ alkyl or C$_2$–C$_8$ alkoxyalkyl;

aryl is phenyl substituted with 0 to 3 substituents independently selected at each occurrence from C$_1$–C$_4$ alkyl, halo, —CN, —OR$^{15}$, —S(O)$_n$R$^{14}$, —COR$^{15}$, —CO$_2$R$^{15}$, —NO$_2$ and —NR$^{15}$R$^{16}$; and n is independently at each occurrence 0, 1 or 2.

[12] Even more preferred compounds of this invention are compounds of Formula (I) and pharmaceutically acceptable salts and pro-drug forms thereof, wherein:

Z is N;

Y is NR$^4$;

Ar is phenyl or pyridyl, each substituted with 2 to 4 R$^5$ groups;

R$^1$ is H, methyl, ethyl, cyclopropyl, —CF$_3$, or —N(CH$_3$)$_2$;

R$^3$ is C$_1$–C$_6$ alkyl, C$_2$–C$_6$ alkenyl, C$_2$–C$_6$ alkynyl, C$_3$–C$_6$ cycloalkyl, C$_1$–C$_4$ haloalkyl or aryl, wherein C$_1$–C$_6$ alkyl, C$_2$–C$_6$ alkenyl, C$_2$–C$_6$ alkynyl or C$_3$–C$_6$ cycloalkyl is each substituted with 0 to 3 substituents independently selected at each occurrence from C$_1$–C$_4$ alkyl, C$_3$–C$_6$ cycloalkyl, —CF$_3$, halo, —CN, —OR$^7$, and aryl;

R$^4$ is H, methyl, ethyl, i-propyl, n-propyl, n-butyl, i-butyl, s-butyl, n-butyl, or allyl;

R$^5$ is independently selected at each occurrence from methyl, ethyl, i-propyl, n-propyl, aryl, —CF$_3$, halo, —CN, —N(CH$_3$)$_2$, —C(=O)CH$_3$, —OCH$_3$, —OCH$_2$CH$_3$, —OCF$_3$, and —S(O)$_2$CH$_3$;

R$^{14}$ is C$_1$–C$_4$ alkyl or —NR$^{15}$R$^{16}$;

R$^{15}$ and R$^{16}$ are independently at each occurrence H, C$_1$–C$_4$ alkyl or C$_2$–C$_8$ alkoxyalkyl;

aryl is phenyl substituted with 0 to 3 substituents independently selected at each occurrence from C$_1$–C$_4$ alkyl, halo, —CN, —OR$^{15}$, —S(O)$_n$R$^{14}$, —COR$^{15}$, —CO$_2$R$^{15}$, —NO$_2$ and —NR$^{15}$R$^{16}$; and n is independently at each occurrence 0, 1 or 2.

[13] A fourth embodiment of preferred compounds of this invention are compounds of Formula (I) and pharmaceutically acceptable salts and pro-drug forms thereof, wherein:

Z is N;

Y is NR$^4$ or O;

Ar is phenyl or pyridyl, each substituted with 0 to 4 R$^5$ groups;

R$^1$ is H, halo, C$_1$–C$_{10}$ alkyl, C$_2$–C$_{10}$ alkenyl, C$_2$–C$_{10}$ alkynyl, C$_3$–C$_8$ cycloalkyl, C$_1$–C$_4$ haloalkyl, aryl, heterocyclyl, —CN, —OR$^7$, —SH, —S(O)$_n$R$^{13}$, —COR$^7$, —CONR$^6$R$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, or —NR$^6$R$^7$, wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^7$, —SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl;

R$^3$ is C$_1$–C$_4$ alkyl, —CN, C$_3$–C$_6$ cycloalkyl, C$_1$–C$_4$ haloalkyl, —OR$^7$, —COR$^7$, —CO$_2$R$^7$ or —CONR$^6$R$^7$, wherein C$_1$–C$_4$ alkyl is substituted with 0 to 3 substituents independently selected at each occurrence from C$_1$–C$_4$ alkyl, C$_3$–C$_6$ cycloalkyl, C$_1$–C$_4$ haloalkyl, halo, —CN, —OR$^7$, —S(O)$_n$R$^{13}$, —COR$^7$, —CO$_2$R$^7$, —NR$^8$COR$^7$, —N(COR$^7$)$_2$, —NR$^8$CONR$^6$R$^7$, —NR$^8$CO$_2$R$^7$, —NR$^6$R$^7$ and —CONR$^6$R$^7$;

R$^4$ is H, C$_1$–C$_6$ alkyl or C$_2$–C$_6$ alkenyl, wherein C$_1$–C$_6$ alkyl is optionally substituted with C$_1$–C$_4$ alkyl, C$_3$–C$_6$ cycloalkyl, C$_1$–C$_4$ haloalkyl, —OR$^7$, —S(O)$_n$R$^{12}$, —CO$_2$R$^7$, —NR$^6$R$^7$ or —NR$^9$COR$^{10}$;

R$^5$ is independently selected at each occurrence from C$_1$–C$_{10}$ alkyl, C$_2$–C$_{10}$ alkenyl, C$_2$–C$_{10}$ alkynyl, C$_3$–C$_6$ cycloalkyl, C$_4$–C$_{12}$ cycloalkylalkyl, aryl, heterocyclyl, —NO$_2$, halo, —CN, C$_1$–C$_4$ haloalkyl, —NR$^6$R$^7$, —NR$^8$COR$^7$, —NR$^8$CO$_2$R$^7$, —OR$^7$, —COR$^7$, —CO$_2$R$^7$, —CONR$^6$R$^7$, —CON(OR$^9$)R$^7$ and —S(O)$_n$R$^{13}$, wherein C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are substituted with 0 to 3 substituents independently selected at each occurrence from C$_1$–C$_4$ alkyl, —NO$_2$, halo, —CN, —OR$^7$, —COR$^7$, —CO$_2$R$^7$, —CONR$^6$R$^7$, —NR$^6$R$^7$, —NR$^8$COR$^7$, —NR$^8$CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heterocyclyl, heterocyclyl(C$_1$–C$_4$ alkyl)-, morpholinoethyl, morpholinopropyl and morpholinobutyl; or NR$^6$R$^7$ taken together as a whole is piperidine, pyrrolidine, piperazine, N-methylpiperazine, morpholine or thiomorpholine;
  wherein C$_1$–C$_4$ alkyl, may be substituted with 0 to 2 substituents independently selected at each occurrence from —OH or C$_1$–C$_4$ alkoxy groups;

R$^8$ is independently at each occurrence H or C$_1$–C$_4$ alkyl;

R$^9$ and R$^{10}$ are independently at each occurrence selected from H, C$_1$–C$_4$ alkyl and C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl, C$_1$–C$_4$ haloalkyl or —NR$^6$R$^7$;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^6$R$^7$, aryl, aryl(C$_1$–C$_4$ alkyl)-, heterocyclyl or heterocyclyl (C$_1$–C$_4$ alkyl)-;

R$^{14}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^{15}$R$^{16}$;

R$^{15}$ and R$^{16}$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl and C$_4$–C$_{12}$ cycloalkylalkyl; or —NR$^{15}$R$^{16}$ taken together as a whole is piperidine, pyrrolidine, piperazine, N-methyl-piperazine, morpholine or thiomorpholine;

aryl is phenyl or naphthyl, each substituted with 0 to 3 substituents independently selected at each occurrence from $C_1$–$C_4$ alkyl, halo, —CN, —OR$^{15}$, —S(O)$_n$R$^{14}$, —COR$^{15}$, —CO$_2$R$^{15}$, —NO$_2$, —NR$^8$COR$^{15}$, —NR$^8$CONR$^{15}$R$^{16}$, —NR$^8$CO$_2$R$^{15}$ and —NR$^{15}$R$^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from $C_1$–$C_4$ alkyl, halo, —CN, —OR$^{15}$, —S(O)$_n$R$^{14}$, —CO$_2$R$^{15}$, —NO$_2$, —NR$^8$COR$^{15}$, —NR$^8$CONR$^{15}$R$^{16}$, —NR$^8$CO$_2$R$^{15}$, and —NR$^{15}$R$^{16}$; and n is independently at each occurrence 0, 1 or 2.

[14] More preferred compounds of the fourth embodiment of this invention are compounds of Formula (I) and pharmaceutically acceptable salts and pro-drug forms thereof, wherein:

Z is N;

Y is NR$^4$;

Ar is phenyl or pyridyl, each substituted with 0 to 4 R$^5$ groups;

R$^1$ is H, halo, $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl, aryl, heterocyclyl, —CN, —OR$^7$, —S(O)$_n$R$^{13}$, —COR$^7$, —CONR$^6$R$^7$, —CO$_2$R$^7$ or —NR$^6$R$^7$, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —OR$^7$, —SH, —S(O)$_n$R$^{13}$, —COR$^7$, —CO$_2$R$^7$, —OC(O)R$^{13}$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl;

R$^3$ is $C_1$–$C_4$ alkyl, —CN, $C_3$–$C_6$ cycloalkyl, $C_1$–$C_4$ haloalkyl, —OR$^7$, —COR$^7$ or —CO$_2$R$^7$, wherein $C_1$–$C_4$ alkyl is substituted with 0 to 3 substituents independently selected at each occurrence from $C_3$–$C_6$ cycloalkyl, $C_1$–$C_4$ haloalkyl, halo, —CN, —OR$^7$, —S(O)$_n$R$^{13}$, —COR$^7$, —CO$_2$R$^7$, —NR$^8$COR$^7$, —NR$^6$R$^7$ and —CONR$^6$R$^7$;

R$^4$ is H, allyl, or $C_1$–$C_4$ alkyl, wherein $C_1$–$C_4$ alkyl is optionally substituted with $C_1$–$C_4$ alkyl, —OR$^7$, —S(O)$_2$R$^{12}$, —CO$_2$R$^7$, —NR$^6$R$^7$ or —NR$^9$COR$^{10}$;

R$^5$ is independently selected at each occurrence from $C_1$–$C_6$ alkyl, aryl, heterocyclyl, $C_1$–$C_4$ haloalkyl, halo, —CN, —NO$_2$, —NR$^6$R$^7$, —COR$^7$, —OR$^7$, —CONR$^6$R$^7$, —CON(OR$^9$)R$^7$, —CO$_2$R$^7$ and —S(O)$_n$R$^{13}$, wherein $C_1$–$C_6$ alkyl is substituted with 0 to 3 substituents independently selected at each occurrence from $C_1$–$C_4$ alkyl, —NO$_2$, halo, —CN, —NR$^6$R$^7$, COR$^7$, —OR$^7$, —CONR$^6$R$^7$, CO$_2$R$^7$ and —S(O)$_n$R$^{13}$;

R$^6$ and R$^7$ are independently selected at each occurrence from H, $C_1$–$C_4$ alkyl, $C_1$–$C_4$ haloalkyl and $C_2$–$C_8$ alkoxyalkyl;

wherein $C_1$–$C_4$ alkyl, may be substituted with 0 to 2 substituents independently selected at each occurrence from —OH or $C_1$–$C_4$ alkoxy groups;

R$^8$, R$^9$ and R$^{10}$ are independently at each occurrence H or $C_1$–$C_4$ alkyl;

R$^{12}$ and R$^{13}$ are independently at each occurrence $C_1$–$C_4$ alkyl or —NR$^6$R$^7$;

R$^{14}$ is $C_1$–$C_4$ alkyl or —NR$^{15}$R$^{16}$;

R$^{15}$ and R$^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —OR$^{15}$, —S(O)$_n$R$^{14}$, —COR$^{15}$, —CO$_2$R$^{15}$, —NO$_2$ and —NR$^{15}$R$^{16}$; and n is independently at each occurrence 0, 1 or 2.

A fifth embodiment of this invention is the method of treating affective disorders, anxiety, depression, post-traumatic stress disorders, supranuclear palsy, seizure disorders, stroke, irritable bowel syndrome, immune suppression, Alzheimer's disease, gastrointestinal disease, anorexia nervosa or other eating disorders, drug or alcohol withdrawal symptoms, drug addiction, inflammatory disorders, or fertility problems in a mammal in need of such treatment comprising administering to the mammal a therapeutically effective amount of a compound of Formula I.

A sixth embodiment of this invention are pharmaceutical compositions comprising a pharmaceutically acceptable carrier and a therapeutically effective amount of a compound of Formula I.

This invention also includes intermediate compounds useful in preparation of the CRF antagonist compounds and processes for making those intermediates, as described in the following description and claims.

The CRF antagonist compounds provided by this invention (and especially labelled compounds of this invention) are also useful as standards and reagents in determining the ability of a potential pharmaceutical to bind to the CRF receptor.

DETAILED DESCRIPTION OF INVENTION

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. For example, the term "$C_1$–$C_{10}$ alkyl" denotes alkyl having 1 to 10 carbon atoms; thus, methyl, ethyl, propyl, butyl, pentyl, hexyl, heptyl, octyl, nonyl and decyl, wherein, for example, butyl can be —CH$_2$CH$_2$CH$_2$CH$_3$, —CH$_2$CH(CH$_3$)$_2$, —CH(CH$_3$)CH$_2$CH$_3$ or —CH(CH$_3$)$_3$.

The term "alkenyl" includes hydrocarbon chains of either a straight or branched configuration and one or more unsaturated carbon—Carbon bonds which may occur in any stable point along the chain. For example, the term "$C_2$–$C_{10}$ alkenyl" denotes alkenyl having 2 to 10 carbon atoms; thus, ethenyl, propenyl, butenyl, pentenyl, hexenyl, heptenyl, octenyl, nonenyl and decenyl, such as allyl, propargyl, 1-buten-4-yl, 2-buten-4-yl and the like, wherein, for example, butenyl can be, but is not limited to, —CH=CH$_2$CH$_2$CH$_3$, —CH$_2$CH=CHCH$_3$, —CH$_2$CH$_2$CH=CH$_2$, —CH=C(CH$_3$)$_2$ or —CH=CHCH=CH$_2$.

The term "alkynyl" includes hydrocarbon chains of either a straight or branched configuration and one or more triple carbon—carbon bonds which may occur in any stable point along the chain. The term "$C_2$–$C_{10}$ alkynyl" denotes alkynyl having 2 to 10 carbon atoms; thus, ethynyl, propynyl, butynyl, pentynyl, hexynyl, heptynyl, octynyl, nonynyl and decynyl.

The term "haloalkyl" is intended to include both branched and straight-chain alkyl having the specified number of carbon atoms, substituted independently with 1 or more halogen, such as, but not limited to, —$CH_2F$, —$CHF_2$, —$CF_3$, —$CF_2Br$, —$CH_2CF_3$, —$CF_2CF_3$, —$CH(CF_3)_2$ and the like.

The term "alkoxy" represents an alkyl group of indicated number of carbon atoms attached through an oxygen bridge.

The term "cycloalkyl" is intended to include saturated ring groups having the specified number of carbon atoms, including mono-, bi- or poly—Cyclic ring systems, such as cyclopropyl (c-Pr), cyclobutyl (c-Bu), cyclopentyl, cyclohexyl, cycloheptyl, cyclooctyl, [3.3.0]bicyclooctyl, [2.2.2]bicyclooctyl and so forth.

As used herein, the term "heterocyclyl" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl, oxazolidinyl, benzothienyl, 2,3-dihydrobenzofuranyl or 2,3-dihydrobenzothienyl.

The term "halo" or "halogen" includes fluoro, chloro, bromo and iodo.

The term "substituted", as used herein, means that one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "pharmaceutically acceptable salts" includes acid or base salts of the compounds of formula (I). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

The term "therapeutically effective amount" of a compound of this invention means an amount effective to antagonize abnormal level of CRF or treat the symptoms of affective disorder, anxiety or depression in a host.

Synthesis

The pyrazinones and triazinones of this invention can be prepared by one of the general schemes outlined below (Scheme 1–6).

Compounds of the Formula (I) wherein Z=CH, Y=$NR^4$, $R^1$=halogen and $R^2$=H can be prepared as shown in Scheme 1. Compounds wherein $R^2$ is a substituent other than H as defined in the broad scope of the invention can also be prepared as shown in Scheme 1 by using the corresponding $R^2$COH substituted aldehydes or Cl$CHR^2$CN substituted haloacetonitriles.

Scheme 1

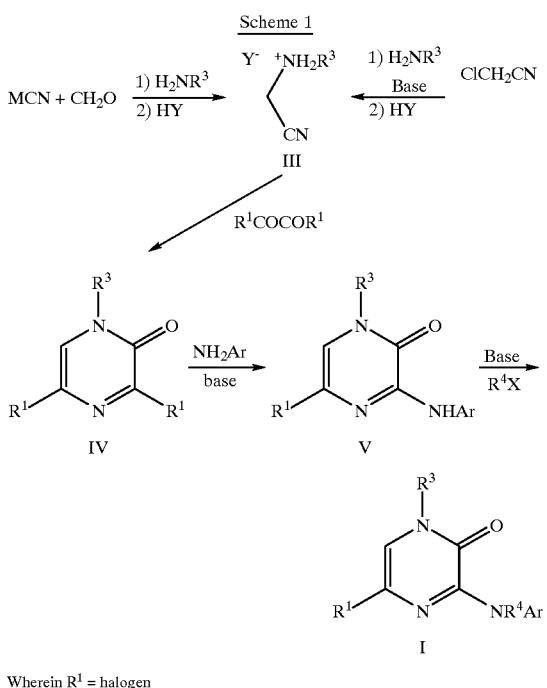

Wherein $R^1$ = halogen

Reaction of a cyanide salt with formaldehyde and the appropriate substituted amine afforded the corresponding aminoacetonitrile which was purified as the hydrochloride salt of Formula (III). Alternatively the same compounds of Formula (III) can be synthesized by reaction of the amine $H_2NR^3$ with a haloacetonitrile, such as chloroacetonitrile, in the presence of a base such as a tertiary amine or an inorganic base such as $K_2CO_3$ in an organic solvent and isolated as a salt of an inorganic acid by treatment with that acid. Amine salt of Formula (III) was treated with an oxalyl halide, $R^1COCOR^1$, such as oxalyl chloride or bromide to afford the dihalo compound Formula (IV), as described in Vekemans, J.; Pollers-Wieers, C.; Hoornaert, G. *J. Heterocyclic Chem.* 20, 919, (1982). Compound Formula (IV) can be coupled with an aryl amine $H_2NAr$ thermally, in the presence of a strong base such as NaH, $KN(SiMe_3)_2$, LiN$(SiMe_3)_2$ or $NaN(SiMe_3)_2$ in an aprotic organic solvent, or under acid catalysis to give compounds of Formula (V). Compounds of Formula (V) can be alkylated with an alkyl halide $R^4X$ to afford compounds of Formula (I).

Compounds where $R^1$=alkyl or substituted alkyl can be prepared according to Scheme 2.

Scheme 2

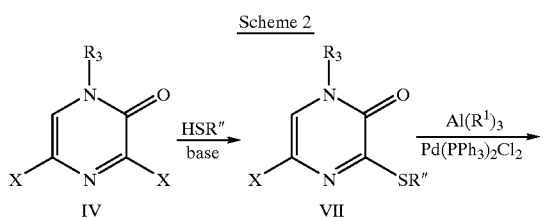

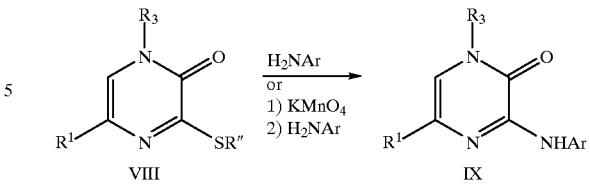

Reaction of the intermediate of Formula (IV) in Scheme 1, wherein $R^1$=X=halogen in Scheme 2, with an alkyl or aryl thiol, HSR", in the presence of base such as NaH affords the adduct of Formula (VII), which may then be treated with a trialkylaluminum as described in Hirota, K.; Kitade, Y.; Kanbe, Y.; Maki, Y.; *J. Org. Chem.* 57, 5268, (1992), in the presence of a palladium catalyst, such as $Pd(PPh_3)_2Cl_2$, to give compounds of Formula (VIII). Condensation of compounds of Formula (VIII) with an aryl amine $H_2NAr$ under thermal, base, or acid catalyzed conditions gives compounds of Formula (IX). Alternatively (VIII) may be oxidized to the corresponding sulfones with an oxidant such as $KMnO_4$ and then condensed with the arylamines of formula $H_2NAr$ to give (IX). The use of appropriately substituted aluminum alkyls, or simple transformations of those substituted alkyls can give access to compounds of Formula (I), where $R^1$ is a substituted alkyl; see Ratovelomanana, V.; Linstrumelle, G.; *Tet. Letters* 52, 6001 (1984) and references cited therein.

Compounds of the Formula (I) wherein Z=CH, Y=O or $S(O)_n$ and $R^1$=halogen can be prepared as shown in Scheme 3.

Scheme 3

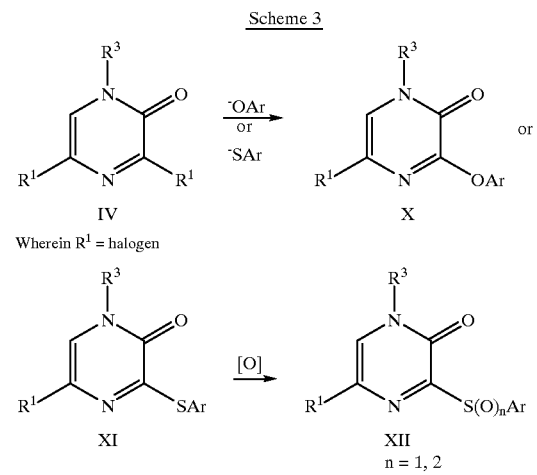

Wherein $R^1$ = halogen

Reaction of the dihalo intermediate (IV) from Scheme 1 with a phenoxide or thiophenoxide, formed by treatment of the corresponding phenol or thiophenol with an appropriate base, such as NaH in an aprotic solvent, gives the adduct of Formula (X) or (XI). Adduct (XI) may be further oxidized to the sulfoxide or sulfone of Formula (XII), by treatment with the appropriate oxidant, such as a peroxide, NaIO4 or KMnO4.

Compounds of Formula (I) where $R^1$=OR, SR and $S(O)_nR$ and Z=CH can be introduced on compounds of Formula (V) by copper or copper salt-catalyzed coupling of the corresponding anions RO⁻ and RS⁻ with the pyrazinone bromide. Keegstra, M. A.; Peters, T. H. A.; Brandsma, L.; *Tetrahedron*, 48, 3633 (1992) describes the addition of phenoxide anions by this method; alternatively, the same conditions can be used for the addition of thiophenoxide anions. Alternatively the same compounds can be synthesized by Scheme 4.

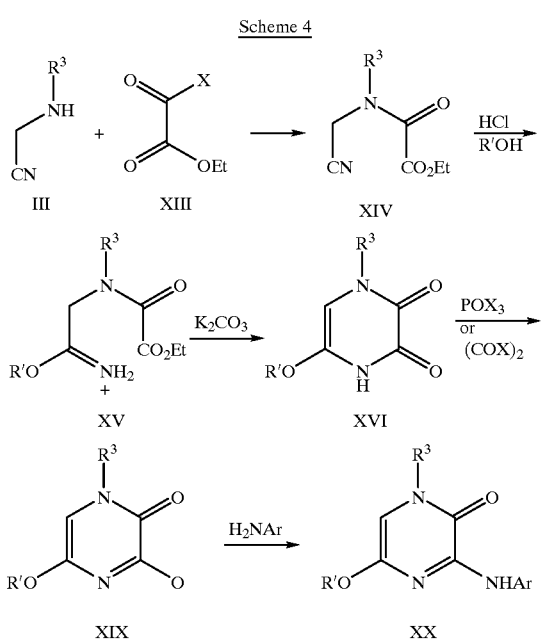

Scheme 4

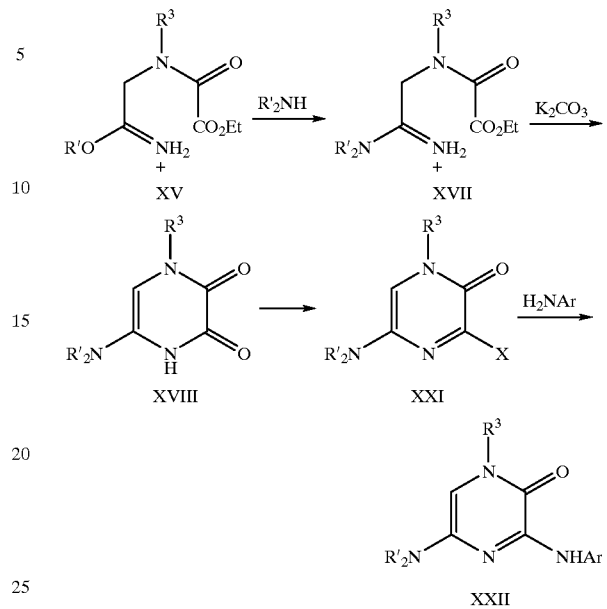

Scheme 5

In Scheme 4, reaction of an aminoacetonitrile salt (III), described in Scheme 1, with an oxalyl halide ester (XIII) gives the corresponding amide (XIV), which in turn can be converted to the corresponding imidate salt (XV). This can be cyclized under treatment with a base, such as $K_2CO_3$ or $Et_3N$ to the pyrazinedione of Formula (XVI). This can be converted to the corresponding halide (XIX), using a halogenating agent such as $POX_3$, oxalyl halide or $SOX_2$. Alternatively, (XVI) can be converted to the corresponding mesylate, tosylate or triflate, by treatment with the corresponding mesyl, tosyl, or triflic anhydride. Subsequently, (XIX) can be coupled with an aniline to the corresponding adduct of Formula (XX), under the conditions described in Scheme 1, or (XIX) can be coupled with a phenoxide or thiophenoxide as described in Scheme 3 to yield compounds of Formula (I) wherein Y=O or $S(O)_n$.

Compounds of Formula (I) wherein $R^1$=substituted N and Z=CH can be introduced on compounds of Formula (XV) by reaction with an amine to form the corresponding amidate (XVII) according to Scheme 5. Subsequently, (XVII) can be cyclized, halogenated, and substituted with the appropriate aniline, phenoxide or thiophenoxide as described in Scheme 4 above.

Compounds of Formula I wherein Z=CH and $R^1$=COR$^7$ or $CO_2R^7$ can be synthesized from compounds of Formula (VII) by coupling with the appropriate vinyl aluminum or boron reagent in the presence of a palladium catalyst, such as $Pd(PPh_3)_2Cl_2$, and further transformations of the vinyl group, using methods known to one skilled in the art.

The compounds of Formula (I) where Z=CH and $R^1$ or $R^3$ is a functional group not compatible with the procedures of Schemes 1–5 may be prepared from precursors where the interfering functionality of $R^1$ or $R^3$ is protected using methods known to one skilled in the art (see T. W. Green and P. G. M. Wuts, *Protecting Groups in Organic Synthesis*, Wiley, New York, 1991); or from precursors bearing $R^1$ or $R^3$ groups amenable to later conversion into the desired functionality using standard methods (see J. March, *Advanced Organic Chemistry*, Wiley, New York, 1992).

Triazinones of Formula (I) wherein Z=N and Y=NR$^4$, O or $S(O)_n$ can be prepared by the synthetic route shown in Scheme 6.

Condensation of a substituted hydrazine with acetamidines or imidates provides amidrazones of Formula (XXX) (Khrustalev, V. A., Zelenin, K. N. Zhurnal Organicheskoi Khimii, Vol. 15, No. 11, 1979, 2280). Cyclization of (XXX) with oxalyl derivatives such as oxalyl chloride provides diones of Formula (XXXI). Treatment of (XXXI) with chlorodehydrating agents such as thionyl chloride, oxalyl chloride or phosphorous oxychloride provides chlorotriazinones of Formula (XXXII), which may be treated with phenols, thiophenols, anilines and their heterocyclic analogs under basic, acidic or thermal conditions to provide compounds of Formula (I) where Z=N and Y=O, S or NH, respectively. In the preceding instance where Y=NH, alkylation of the nitrogen atom with e.g. alkyl iodides provides the related compounds of Formula (I) where Z=N and Y=NR$^4$. In the preceding instance where Y=S, oxidation with e.g. mCPBA provides the compounds of Formula (I) where Z=N and Y=S(O) and $S(O)_2$. The compounds of Formula (I) where Z=N and $R^1$ or $R^3$ is a functional group not compatible with the procedures of Scheme 4 may be prepared from precursors such as amidrazones of Formula (XXX) or substituted hydrazines where the

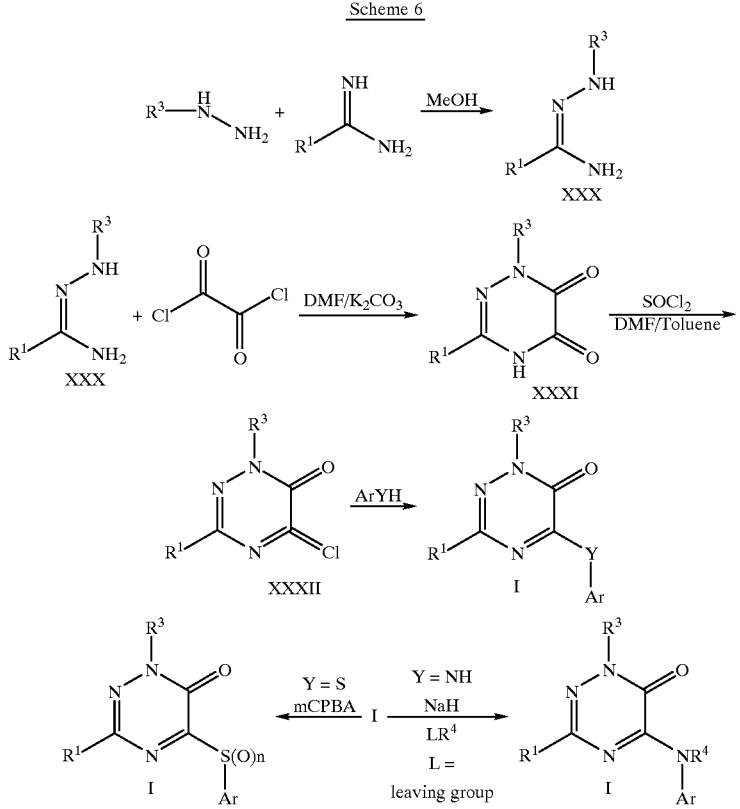

interfering functionality of $R^1$ or $R^3$ is protected using methods known to one skilled in the art (see T. W. Green and P. G. M. Wuts, *Protecting Groups in Organic Synthesis*, Wiley, New York, 1991); or from precursors bearing $R^1$ or $R^3$ groups amenable to later conversion into the desired functionality using standard methods (see J. March, *Advanced Organic Chemistry*, Wiley, New York, 1992).

Triazinones of Formula (I) wherein Z=N and Y=NR$^4$, O or S(O)$_n$ can also be prepared by the synthetic route shown in Scheme 7

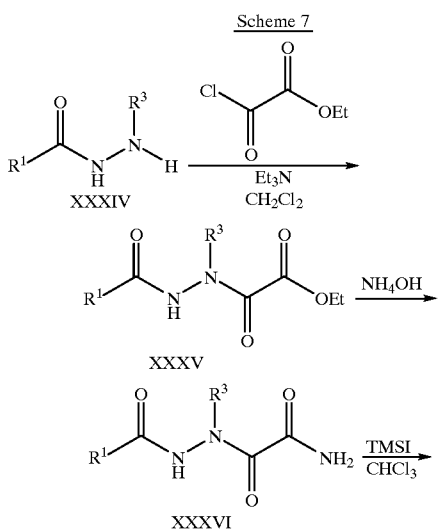

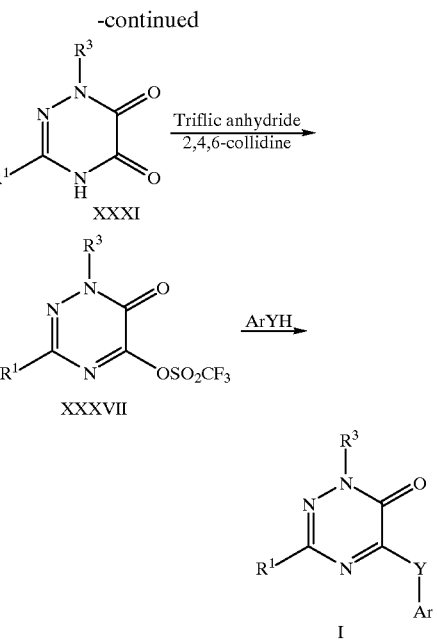

Reaction of ethyl oxalyl chloride with acylated hydrazines of Formula (XXXIV) provides the ethyl oxalyl acylhydrazine derviatives of Formula (XXXV). Compounds of Formula (XXXIV) may be arrived at via condensation of an appropriate ketone or aldehyde with an acylated hydrazide to give acylated hydrazones which may then be reduced under catalytic hydrogenation conditions or by other reducing agents to give the compounds of Formula (XXXIV). The abovementioned acylated hydrazones may also be produced by acylation of a hydrazone made from hydrazine and an appropriate ketone or aldehyde using methods known to one skilled in the art of organic synthesis. Alternatively, compounds of Formula (XXXIV) may also be produced by acylation of an appropriate hydrazine using methods known to one skilled in the art of organic synthesis.

The ethyl esters of compound (XXXV) may then be converted to the primary amide derivatives of Formula (XXXVI) by treatment with an ammonia source such as ammonium hydroxide. Cyclization of (XXXVI) to produce the diones of Formula (XXXI) may be achieved by treatment with, for example, iodotrimethylsilane (TMSI) or $POCl_3$, or by heating in the presence of a Lewis acid such as $ZnCl_2$. The oxo group in the 5 position of the 1,2,4-triazin-5,6-diones of Formula (XXXI) may then be converted to a leaving group using reagents such as trifluoromethanesulfonic anhydride under basic conditions to yield compounds of Formula (XXXVII) which may then be treated with phenols, thiophenols, anilines and their heterocyclic analogs under basic conditions to provide compounds of Formula (I)

Additional 1,2,4-triazinone syntheses are disclosed in the literature (A. R. Katritzky and C. W. Rees, *Comprehensive Heterocyclic Chemistry*, Pergamon Press, New York, Vol. 3, 1984, p. 385) and can be prepared by one skilled in the art.

Intermediates, for example ArYH, $H_2NAr$, HOAr or HSAr, in the synthesis of compounds of Formula (I) in Schemes 1–6 may be prepared using standard methods known to one skilled in the art (see, D. Barton and W. D. Ollis, *Comprehensive Organic Chemistry*, Pergamon Press, New York, Vol. 1–6, 1979; A. R. Katritzky and C. W. Rees, *Comprehensive Heterocyclic Chemistry*, Pergamon Press, New York, Vol. 1–8, 1984; B. Trost and I. Fleming, *Comprehensive Organic Synthesis*, Pergamon Press, New York, Vol. 1–9, 1991; and DuPont Merck PCT application WO95/10506).

All of the aforementioned references are hereby incorporated by reference.

EXAMPLE 1

3-[[2-Bromo-4-(1-methylethyl)phenyl]amino]-5-chloro-1-(1-ethylpropyl)-2(1H)-pyrazinone Part A Hydrogen chloride (12M, aq., 3.8 mL), methanol (33 mL), water (30 mL), potassium cyanide (3 g), 1-ethylpropylamine (4 g), and formaldehyde (37% w/v, 3.7 mL) were stirred 18 hours at room temperature. Water (200 mL) was added, and the mixture was extracted with 2×200 mL methylene chloride, which was dried over MgSO4 and concentrated to a light oil (5.57 g). The oil was dissolved in ether and 1N HCl was added. The precipitate was collected on paper and dried to give N-(1-ethylpropyl)-aminoacetonitrile hydrochloride as an off-white solid (6.70 g).

Part B: The product from part A (2 g), chloroform (20 mL), and oxalyl chloride (4.68 g) were heated at reflux for 12 hours. The reaction was concentrated to remove excess oxalyl chloride and solvent, and the crude product was chromatographed on silica gel using ethyl acetate/hexane (1:4) as eluent to afford 3,5-dichloro-1-(1-ethylpropyl)-2 (1H)-pyrazinone as a white solid (2.09 g).

Part C

The product from part B (0.68 g) and 2-bromo-4-isopropylaniline (1.24 g) were heated at 140° C. for 5 hours. After cooling, methylene chloride (20 mL) was added, filtered, and concentrated. The crude product was chromatographed on silica gel using ethyl acetate/hexane (1:9) as eluent to afford the title compound. 639 mg. mp 118.5–119.5° C. Elemental analysis: calcd. for $C_{18}H_{23}N_3OBrCl$: C, 52.38; H, 5.626; N, 10.18; Br, 19.36; Cl, 8.599. Found: C, 52.62; H, 5.43; N, 10.13; Br, 19.53; Cl, 8.97.

EXAMPLE 2

3-[[2-Bromo-4-(1-methylethyl)phenyl]ethylamino]-5-chloro-1-(1-ethylpropyl)-2(1H)-pyrazinone The product from Example 1 (198 mg), N,N-dimethylformamide (5 mL), and sodium hydride (60% in oil, 96 mg) were stirred at room temperature 20 minutes. Iodoethane (112 mg) was added and the reaction was stirred overnight at room temperature and quenched with water (10 mL) and saturated sodium chloride (aq., 10 mL). The mixture was extracted with methylene chloride which was dried and concentrated. The crude product was chromatographed on silica gel using ethyl acetate/hexane (1:19) as eluent to afford the title compound (125 mg). CI-HRMS calcd. for $C_{20}H_{28}N_3OClBr$ $(M+H)^+$: 440.110427. Found: 440.107480.

EXAMPLE 3

3-[(2,4-Dibromophenyl)amino]-5-Chloro-1-(1-ethylpropyl)-2(1H)-pyrazinone 2,4-Dibromoaniline (500 mg), toluene (8 mL), and sodium hydride (60% in oil, 398 mg) were stirred for 10 minutes at room temperature and then 3,5-dichloro-1-(1-ethylpropyl)-2(1H)-pyrazinone (468 mg, Example 1, part B) was added. The reaction was heated at reflux 3 hours, cooled, and quenched with water (50 mL). The mixture was extracted with ethyl acetate (100 mL), which was washed with brine, then dried and concentrated. The crude product was chromatographed on silica gel using ethyl acetate/hexane (1:19) affording 400 mg of material, which was crystallized from ether/hexane to give the title compound (240 mg). Elemental analysis: calcd. for $C_{15}H_{16}N_3OClBr_2$: C, 40.07; H, 3.597; N, 9.356; Cl, 7.895; Br, 35.55. Found: C, 40.41; H, 3.49; N, 9.34; Cl, 8.27; Br, 35.71.

EXAMPLE 4

3-[(2,4-Dibromophenyl)ethylamino]-5-chloro-1-(1-ethylpropyl)-2(1H)-pyrazinone

The title compound was prepared in a manner similar to the product of Example 2. Elemental analysis calcd. for $C_{17}H_{20}N_3OClBr_2$: C,42.75; H,4.22; N, 8.807. Found: C, 42.82; H, 4.14; N, 8.67.

EXAMPLE 5

3-[(2,4,6-Trimethylphenyl)amino]-5-chloro-1-(1-ethylpropyl)-2(1H)-pyrazinone

The title compound was prepared in a manner similar to the product of Example 3. Elemental analysis calcd. for $C_{18}H_{24}N_3OCl$: C, 64.76; H, 7.256; N, 12.59. Found: C, 64.69; H, 7.03; N, 12.55.

EXAMPLE 6

3-[(2,4,6-Trimethylphenyl)ethylamino]-5-chloro-1-(1-ethylpropyl)-2(1H)-pyrazinone The title compound was prepared in a manner similar to the product of Example 2. Elemental analysis calcd. for $C_{20}H_{28}N_3OCl$: C, 66.37; H, 7.808; N, 11.61. Found: C, 66.50; H, 7.69; N, 11.51.

EXAMPLE 7

(+/−)-3-[(2,4,6-Trimethylphenyl)amino]-5-chloro-1-[1-(methoxymethyl)propyl]-2(1H)-pyrazinone The title compound was prepared in a manner similar to the product of Example 3. Elemental analysis calcd. for $C_{18}H_{24}N_3O_2Cl$: C, 61.80; H, 6.91; N, 12.01; Cl, 10.13. Found: C, 61.69; H, 7.00; N, 11.93; Cl, 9.87.

EXAMPLE 8

3-[(2-Bromo-4,6-dimethoxyphenyl)amino]-5-chloro-1-(1-ethylpropyl)-2(1H)-pyrazinone The title compound was prepared in a manner similar to the product of Example 3. Elemental analysis calcd. for $C_{17}H_{21}N_3O_3BrCl$: C, 47.40; H, 4.91; N, 9.765. Found: C, 47.06; H, 4.61; N, 9.56.

EXAMPLE 9

3-[(2-Cyano-4,6-dimethylphenyl)amino]-5-chloro-1-(1-ethylpropyl)-2(1H)-pyrazinone Part A 3-[(2-Iodo-4,6-dimethylphenyl)amino]-5-chloro-1-(1-ethylpropyl)-2(1H)-pyrazinone was prepared in a manner similar to Example 3.

Part B

The product from part A (460 mg), N,N-dimethylformamide (8 mL), cuprous cyanide (97 mg), and sodium cyanide were heated at 120° C. for 18 hours and then at 130° C. for 3 hours. After cooling, ethyl acetate (100 mL) was added to the reaction which was then washed with water (50 mL) and brine (50 mL), dried, and concentrated. The crude product was chromatographed on silica gel using ethyl acetate/hexane (1:4) as eluent. The product was then crystallized from methylene chloride/hexane to afford the title compound (235 mg). Elemental analysis calcd. for $C_{18}H_{21}N_4OCl$: C, 62.69; H, 6.148; N, 16.25; Cl, 10.28. Found: C, 62.29; H, 6.27; N, 15.99; Cl, 10.20.

EXAMPLE 10

(+/−)-3-[(2-Bromo-4,6-dimethoxyphenyl)amino]-5-chloro-1-[1-(methoxymethyl)propyl]-2(1H)-pyrazinone The title compound was prepared in a manner similar to the product of Example 3. Elemental analysis calcd. for $C_{17}H_{21}N_3O_4BrCl$: C, 45.71; H, 4.748; N, 9.416. Found: C, 45.86; H, 4.43; N, 9.26.

EXAMPLE 12

(+/−)-3-[(2-Iodo-4,6-dimethylphenyl)amino]-5-chloro-1-[1-(methoxymethyl)propyl]-2(1H)-pyrazinone Part A Chloroacetonitrile (3.2 mL), 2-amino-1-methoxybutane (10.32 g), and deuterochloroform (50 mL) were stirred and heated at reflux for 48 h. Methylene chloride (100 mL) and sodium hydroxide (aq., 1N, 100 mL) were added to the reaction, the layers separated, and the organic layer concentrated to an oil (3.4 g). The oil was dissolved in ether (100 mL) and HCl/ether (1N, 100 mL) was added. The precipitate was collected on paper affording N-[(1-methoxymethyl)propyl]aminoacetonitrile hydrochloride (6.86 g).

Part B

The title compound was prepared in a manner similar to the product of Example 3. Elemental analysis calcd. for $C_{17}H_{21}N_3O_2ClI$: C, 44.22; H, 4.58; N, 9.10. Found: C, 44.26; H, 4.60; N, 9.83.

EXAMPLE 15

(+/−)-3-[(4-Bromo-2,6-dimethylphenyl)amino]-5-chloro-1-[1-(methoxymethyl)propyl]-2(1H)-pyrazinone To (+/−)-3,5-dichloro-1-[1-(methoxymethyl)propyl]-2(1H)-pyrazinone (300 mg) and 4-bromo-2,6-dimethylaniline (238 mg) in THF (anhydrous, 9.4 mL) at 0° C. was added sodium bis(trimethylsilyl)amide (1.0 M/THF, 2.6 mL). The mixture was stirred at 0° C. for 10 minutes. Ethyl acetate (100 mL) was added and washed with water (25 mL) and brine (25 mL). The organic layer was dried over $MgSO_4$ and concentrated and the crude product was chromatographed on silica gel using ethyl acetate/hexane (1:4) as eluent. The product was then crystallized from ethyl acetate/hexane to afford the title compound (419 mg). Elemental analysis calcd. for $C_{17}H_{21}N_3O_2BrCl$: C, 49.23; H, 5.10; N, 10.13. Found: C, 49.33; H, 5.05; N, 10.09.

EXAMPLE 16

(+/−)-3-[(4-Acetyl-2,6-dimethylphenyl)amino]-5-chloro-1-[1-(methoxymethyl)propyl]-2(1H)-pyrazinone To the product of Example 15 (250 mg), bis(triphenylphosphine)palladium(II) chloride (11 mg), and tetrakis(triphenylphosphine)palladium(0) (17 mg) in a dry flask under nitrogen was added toluene (1.5 mL) and 1-ethoxyvinyl tributyl tin (260 mg). The reaction was heated at reflux 18 hours, and then concentrated in vacuo. The residue was taken up in ether (15 mL) and saturated aqueous potassium fluoride (15 mL), and filtered. The layers were separated, and the ether layer was stirred with 1N HCl (aq., 15 mL). The layers were separated and the ether layer was dried over $MgSO_4$ and concentrated. The crude product was chromatographed on silica gel using ethyl acetate/hexane (3:7) as eluent to afford the title compound (90 mg). Elemental analysis calcd. for $C_{19}H_{24}N_3O_3Cl$: C, 60.39; H, 6.40; N, 11.12. Found: C, 60.51; H, 6.31; N, 11.00.

EXAMPLE 16a (+/−)-3-[(4-Acetyl-2-methoxy-6-methylphenyl)amino]-5-chloro-1-[1-(methoxymethyl)propyl]-2(1H)-pyrazinone The title compound was prepared in a manner similar to the product of Example 16. Elemental analysis calcd. for $C_{19}H_{24}N_3O_4Cl$: C, 57.94; H, 6.14; N, 10.67. Found: C, 57.70; H, 5.98; N, 10.41.

EXAMPLE 20

(+/−)-3-[(4-Chloro-2-iodo-6-methylphenyl)amino]-5-chloro-1-[1-(methoxymethyl)propyl]-2(1H)-pyrazinone The title compound was prepared in a manner similar to the product of Example 3. Elemental analysis calcd. for $C_{16}H_{18}N_3O_2Cl_2I$: C, 39.86; H, 3.76; N, 8.725. Found: C, 40.00; H, 3.69; N, 8.64.

EXAMPLE 21

3-[(2,4,6-Trimethylphenyl)amino]-5-chloro-1-[1-(methoxymethyl)-2-methoxyethyl]-2(1H)-pyrazinone Part A To serinol (9.90 g) in DMF (200 mL) was added triethyl amine (14.6 mL) and then chlorotriphenylmethane (24.3 g). The reaction mixture was stirred at room temperature for 18 hours. Toluene (800 mL) was added and washed with water (500 mL and 250 mL) and brine (250 mL), and then dried over $K_2CO_3$ and concentrated to dryness. The product was crytallized from benzene/hexane (1:1) to afford product (14.57 g).

Part B

The product from part A (14.57 g), sodium hydroxide (17.5 g), and iodomethane (8.8 mL) were stirred overnight in DMSO (220 mL) at room temperature. Water (500 mL) was added and extracted with ethyl acetate (3×250 mL). The extracts were washed with water (2×250 mL) and brine (200 mL), dried over $K_2CO_3$, and concentrated to give product (14.46 g).

Part C

The product from part B (14.46 g) and hydrogen chloride (1M/$Et_2O$, 84 mL) were stirred in methanol (300 mL) at room temperature for 6 hours. The solution was washed with hexane (3×300 mL), concentrated, and co-evaporated with ethanol affording 2-amino-1,3-methoxypropane (5.69 g).

Part D

The title compound was prepared in a manner similar the product of Example 3. Elemental analysis calcd. for $C_{18}H_{24}N_3O_3Cl$: C, 59.09; H, 6.61; N, 11.49. Found: C, 20 59.27; H, 6.53; N, 11.47.

EXAMPLE 30a (+/−)-3-[(2-Chloro-4,6-dimethylphenyl)amino]-5-methyl-1-[1-(methoxymethyl)propyl]-2(1H)-pyrazinone The title compound was prepared in a manner similar to the product of Example 84. Elemental analysis calcd. for C18H24N3O2Cl: C, 61.80; H, 6.91; N, 12.01. Found: C, 61.70; H, 6.94; N, 11.56.

EXAMPLE 36

3-[(2,4,6-Trimethylphenyl)amino]-5-chloro-1-[1-(methoxymethyl)-3-methoxypropyl]-2(1H)-pyrazinone The title compound was prepared in a manner similar to the product of Example 15. Elemental analysis calcd. for $C_{19}H_{26}N_3O_3Cl$: C, 60.07; H, 6.908; N, 11.06. Found: C, 60.22; H, 7.16; N, 10.92.

EXAMPLE 36a

3-[(4-Bromo-2-methoxy-6-methylphenyl)amino]-5-chloro-l-[1-(methoxymethyl)-3-methoxypropyl]-2(1H)-pyrazinone The title compound was prepared in a manner similar to the product of Example 15. Elemental analysis calcd. for $C_{18}H_{23}N_3O_4ClBr$: C, 46.92; H, 5.03; N, 9.129. Found: C, 47.29; H, 5.03; N, 8.98.

EXAMPLE 45a

3-[(2-Bromo-6-flouro-4-methylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{16}H_{18}N_3O_3FClBr$: C, 44.21; H, 4.17; N, 9.67. Found: C, 44.35; H, 4.25; N, 9.41.

EXAMPLE 46a

3-[(2-Chloro-4-methoxy-6-methylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{17}H_{20}N_3O_4C_{12}$: C, 50.89; H, 5.02; N, 10.47. Found: C, 50.72; H, 5.33; N, 10.37.

EXAMPLE 49

3-[(4-Bromo-2,6-dimethylphenyl)amino]-5-chloro-1-[1-(methoxymethyl)-3-methoxypropyl]-2(1H)-pyrazinone The title compound was prepared in a manner similar to the product of Example 15. Elemental analysis calcd. for $C_{18}H_{23}N_3O_3ClBr$: C, 48.61; H, 5.21; N, 9.457. Found: C, 48.59; H, 5.32; N, 9.45.

EXAMPLE 53

3-[(4-Bromo-2,6-dimethylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{17}H_{21}N_3O_3ClBr$: C, 47.40; H, 4.91; N, 9.765. Found: C, 47.52; H, 4.99; N, 9.72.

EXAMPLE 54

3-[(2-Chloro-4,6-dimethylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{17}H_{21}N_3O_3Cl_2$: C, 52.86; H, 5.489; N, 10.88. Found: C, 52.89; H, 5.44; N, 10.72.

EXAMPLE 77

(+/−)-3-[(2,6-Dimethyl-4-thiomethylphenyl)amino]-5-chloro-1-[1-(methoxymethyl)propyl]-2(1H)-pyrazinone The title compound was prepared in a manner similar to the product of Example 15. Elemental analysis calcd. for $C_{18}H_{24}N_3O_2ClS$: C, 56.62; H, 6.33; N, 11.00; S, 8.405. Found: C, 56.66; H, 6.19; N, 10.89; S, 8.45.

EXAMPLE 79

(+/−)-3-[(2-Chloro-4,6-dimethylphenyl)amino]-5-chloro-1-[1-(methoxymethyl)propyl]-2(1H)-pyrazinone The title compound was prepared in a manner similar to the product of Example 15. Elemental analysis calcd. for $C_{17}H_{21}N_3O_2Cl_2$: C, 55.14; H, 5.726; N, 11.35. Found: C, 55.27; H, 5.70; N, 11.25.

EXAMPLE 80

(+/−)-3-[(4-Bromo-6-methoxy-2-methylphenyl) amino]-chloro-1-[1-(methoxymethyl)propyl]-2(1H)-pyrazinone The title compound was prepared in a manner similar to the product of Example 15. Elemental analysis calcd. for $C_{17}H_{21}N_3O_3BrCl$: C, 47.40; H, 4.91; N, 9.765. Found: C, 47.91; H, 4.95; N, 9.74.

EXAMPLE 81

3-[(2,6-Dimethyl-4-thiomethylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{18}H_{24}N_3O_3ClS$: C, 54.33; H, 6.08; N, 10.56; S, 8.06. Found: C, 54.48; H, 6.01; N, 10.46; S, 7.86.

EXAMPLE 83

3-[(4-Bromo-2-methoxy-6-methylphenyl)amino]-5-chloro-1-[1-(methoxymethyl)-2-methoxyethyl]-2(1H)-pyrazinone The title compound was prepared in a manner similar to the product of Example 15. Elemental analysis calcd. for $C_{17}H_{21}N_3O_4ClBr$: C, 45.71; H, 4.748; N, 9.416. Found: C, 45.80; H, 4.70; N, 9.39.

EXAMPLE 84

3-[(2,4,6-Trimethylphenyl)amino]-1-(1-ethylpropyl)-5-methyl-2(1H)-pyrazinone

Part A

N-(1-ethylpropyl)aminoacetonitrile hydrochloride (1.41 g) and oxalyl bromide (2.0 M/$CH_2Cl_2$, 13 mL) were heated at reflux for 18 hours. The reaction was concentrated to remove excess oxalyl bromide and solvent, and the crude product was chromatographed on silica gel using ethyl acetate/hexane (1:4) as eluent to afford 3,5-dibromo-1-(1-ethylpropyl)-2(1H)-pyrazinone as a white solid (1.19 g).

Part B

The product from part A (133 mg) and sodium thiomethoxide (29 mg) were combined in THF (1.5 mL) and stirred at 25° C. 4 hours. More sodium thiomethoxide (29 mg) was added and the reaction was stirred for 2 hours more at room temperature. Water (20 mL) was added and extracted with $CH_2Cl_2$ (2×20 mL). The organic layers were combined, dried over $MgSO_4$, and concentrated. The crude product was chromatographed on silica gel using ethyl acetate/hexanes (1:4) as eluent to afford 5-bromo-1-(1-ethylpropyl)-3-thiomethyl-2(1H)-pyrazinone (78 mg).

Part C

The product from part B (200 mg) and Pd(PPh$_3$)$_2$Cl$_2$ (40 mg) were combined in dry THF (6 mL) under inert atmosphere (N$_2$). To that a 2M solution AlMe$_3$ in hexanes (0.5 mL) was added and the reaction was heated at reflux for one hour. The excess AlMe$_3$ was quenched with water at 0° C. and the mixture was partitioned between ethyl acetate (50 mL) and water (30 mL). The water was separated and extracted with ethyl acetate (50 mL), and the combined EtOAc extracts were washed with brine, dried (MgSO$_4$) and stripped in vacuo. The crude product was chromatographed on silica gel using ethyl acetate/hexanes as eluent (1:9) to give 1-(1-ethylpropyl)-5-methyl-3-thiomethyl-2(1H)-pyrazinone (100 mg).

Part D

The product from part B (50 mg) and 2,4,6-trimethylaniline (40 mg) were combined in dry THF (2 mL) under inert atmosphere (N$_2$), and cooled to 0° C. To that a 1M solution NaN(SiMe$_3$)$_2$ in THF (0.5 mL) was added dropwise and the reaction was stirred at 0° C. for 20 min. Then an additional NaN(SiMe$_3$)$_2$ in THF (0.3 mL) was added and the reaction was stirred at 0° C. for 30 min and at 25° C. for one hour. Then it was quenched with water (30 mL) and extracted with ethyl acetate (80 mL). The ethyl acetate was washed with brine, dried (MgSO$_4$) and stripped in vacuo. The crude product was chromatographed on silica gel using ethyl acetate/hexanes as eluent (1:9) to give 3-[(2,4,6-trimethylphenyl)amino]-1-(1-ethylpropyl)-5-methyl-2(1H)-pyrazinone (40 mg). mp. 109° C.

EXAMPLE 84a

3-[(2-Chloro-4,6-dimethylphenyl)amino]-1-(1-ethylpropyl)-5-methyl-2(1H)-pyrazinone The title compound was prepared in a manner similar to the product of Example 84. Elemental analysis calcd. for $C_{18}H_{24}N_3OCl$: C, 64.76; H, 7.256; N, 12.59. Found: C, 65.12; H, 7.28; N, 12.33.

EXAMPLE 84b

3-[(2-Chloro-4-methoxy-6-methylphenyl)amino]-1-(1-ethylpropyl)-5-methyl-2(1H)-pyrazinone The title compound was prepared in a manner similar to the product of Example 84. Elemental analysis calcd. for $C_{18}H_{24}N_3O_2Cl$: C, 61.80; H, 6.91; N, 12.01. Found: C, 61.72; H, 6.96; N, 11.83.

EXAMPLE 84c

3-[(2,4,6-Trimethylphenyl)amino]-1-(1-ethylpropyl)-5-ethyl-2(1H)-pyrazinone

Part A 5-bromo-1-(1-ethylpropyl)-3-thiomethyl-2(1H)-pyrazinone was prepared in a manner similar to Example 84, parts A and B.

Part B

To the product of part A (2.14 g) and bis (triphenylphosphine)palladium(II) chloride (258 mg) in anhydrous THF (60 mL) under inert atmosphere was added triethyl aluminum (1 M/THF, 14.7 mL). The reaction was heated at reflux 3 hours and then cooled and quenched with water. Ethyl Acetate (200 mL) was added and washed with water and saturated aqueous sodium chloride. The ethyl acetate was dried over MgSO$_4$ and concentrated in vacuo. The crude product was chromatographed on silica gel using ethyl acetate/hexane (3:17) as eluent to afford 5-ethyl-1-(1-ethylpropyl)-3-thiomethyl-2(1H)-pyrazinone (809 mg).

Part C

The title compound was prepared in a manner similar to the product of Example 84 using the procuct from part B. Elemental analysis calcd. for $C_{20}H_{29}N_3O$: C, 73.36; H, 8.936; N, 12.83. Found: C, 73.01; H, 8.55; N, 12.69.

EXAMPLE 84d

3-[(2-Chloro-4,6-dimethylphenyl)amino]-1-(1-ethylpropyl)-5-ethyl-2(1H)-pyrazinone The title compound was prepared in a manner similar to the product of Example 84c. Elemental analysis calcd. for $C_{19}H_{26}N_3OCl$: C, 65.60; H, 7.53; N, 12.08. Found: C, 65.53; H, 7.33; N, 11.92.

EXAMPLE 85

3-[(2,4,6-Trimethylphenyl)amino]-5-bromo-1-(1-ethylpropyl)-2(1H)-pyrazinone

Part A

N-(1-ethylpropyl)-aminoacetonitrile hydrochloride (1.41 g) and oxalyl bromide (2.0 M, $CH_2Cl_2$, 13 mL) were heated at reflux for 18 hours. The reaction was concentrated to remove excess oxalyl bromide and solvent, and the crude product was chromatographed on silica gel using ethyl acetate/hexane (1:4) as eluent to afford 3,5-dibromo-1-(1-ethylpropyl)-2(1H)-pyrazinone as a white solid (1.19 g).

Part B

Using the product of part A, the title compound was prepared in a manner similar to the product of Example 3. MS m/z 378, (m+H)⁺, 100%.

EXAMPLE 204

5-[(2,4,6-Trimethylphenyl)amino]-3-methyl-1-(1-ethylpropyl)-1,2,4-triazine-6(1H)-one Part A 3-Pentanone (18.56 g, 0.215 mol), acetic hydrazide (14.8 g, 0.2 mol), and 200 mL of absolute ethanol were placed in a 500 mL flask. The reaction mixture was reluxed for 18 hr and then evaporated to dryness to afford the desired hydrazone of suitable purity.

The hydrazone was then dissolved in 200 mL of glacial acetic acid containing 1.0 g of $PtO_2$ and hydrogenated at 50 psi hydrogen pressure for 14 hr. The mixture was decanted from the catalyst and evaporated to dryness to afford 23.9 g of a colorless oil (83% yield for the two steps).

Part B

The 1-acetyl-2-(1-ethylpropyl)hydrazine product from Part A (23.9 g, 0.166 mol) was dissolved in $CH_2Cl_2$ (200 mL) and to the stirring solution was added triethylamine (27.9 mL, 0.2 mol) and ethyl oxalyl chloride (19 mL, 0.17 mol). After stirring at room temperature for 3 hr, the reaction mixture was poured into water and the organic layer was separated, dried ($Na_2SO_4$), filtered and evaporated in vacuo. To the resultant oil was added ammonium hydroxide (250 mL), THF (100 mL), and ethanol (50 mL). The flask containing the mixture was sealed with a rubber septum and stirred for 18 hr at room temperature. The mixture was then concentrated in vacuo until the reduced volume of solvent remaining was approximately 100 mL, and a white precipitate had formed. The flask was then placed in the refrigerator for 1 hr. The precipitate was collected by vacuum filtration and washed with small volumes of cold water. 26.3 g of a white solid was collected (73% yield). ¹H NMR (300 MHz, $CDCl_3$): δ7.78 (s, 1H); 6.74 (br s, 1H); 5.6 (br s, 1H); 4.25 (m, 1H); 2.04 (s, 1H); 1.5 (m, 4H); 0.95 (t, 6H, J=7.3 Hz).

Part C

The 1-oxamyl-1-(3-pentyl)-2-acetylhydrazine product from Part B (2 g, 9.3 mmol) was suspended in chloroform (50 mL) and 2 mL of iodotrimethylsilane was added dropwise. The mixture was allowed to stir at room temperature for 12 hr. The reaction mixture was then partitioned between $CH_2Cl_2$ and 1N NaOH. The aqueous layer was separated and made acidic by addition of conc. HCl and then extracted with $CH_2Cl_2$. This organic layer was dried ($Na_2SO_4$), filtered and evaporated in vacuo to yield 1.2 g of an off-white solid of suitable purity (65% yield). ¹H NMR (300 MHz, $CDCl_3$): δ7.85 (br s, 1H); 4.61 (m, 1H); 2.35 (s, 3H); 1.73 (m, 4H); 0.83 (t, 6H, J=7.3 Hz).

Part D

To a solution of the triazine dione product from above (198 mg, 1 mmol) in $CH_2Cl_2$ (5 mL) was added trifluoromethanesulfonic anhydride (0.19 mL, 1.1 mmol) and 2,4,6-collidine (0.15 mL, 1.1 mmol). The resulting reaction mixture was stirred at room temperature for 30 min., then 2,4,6-trimethylaniline (162 mg, 1.2 mmol) in 5 mL of THF was added followed by addition of 2,4,6-collidine (0.15 mL, 1.1 mmol). The resulting reaction mixture was stirred at room temperature for 1 hr, at which time TLC showed complete reaction. The reaction mixture was partitioned between water and $CH_2Cl_2$. The organic layer was dried ($Na_2SO_4$), filtered and evaporated in vacuo. The residue was purified by column chromatography on silica gel using EtOAc/hexane (1:9) to afford 260 mg of the title compound (83% yield). mp=133–135° C. ¹H NMR (300 MHz, $CDCl_3$): δ7.89 (br s, 1H); 6.94 (s, 2H); 4.72 (m, 1H); 2.31 (s, 3H); 2.19 (s, 9H); 1.9–1.7 (m, 4H); 0.85 (t, 6H, J=7.32 Hz). Mass Spec. ($NH_3$—CI): Calc. (M+H)+=315, Obs. (M+H)+=315.

EXAMPLE 703

(+/−)-5-Chloro-1-[1-(methoxymethyl)propyl]-3-(2,4,6-trimethylphenoxy)-2(1H)-pyrazinone Part A (+/−)-3,5-dichloro-1-[1-(methoxymethyl)propyl]-2(1H)-pyrazinone was prepared in a manner similar to Example 12, part A, and Example 1, part B.

Part B 2,4,6-Trimethylphenol (59 mg) and potassium t-butoxide (48 mg) were added to pyridine (2 mL) at 0° C. The mixture was warmed to ambient temperature and (+/−)-3,5-dichloro-1-[1-(methoxymethyl)propyl]-2(lH)-pyrazinone (98 mg) and copper (I) iodide (19 mg) were added. The reaction mixture was stirred at ambient temperature for three hours and then heated at reflux for three hours and then cooled to 0° C. Ethyl acetate (50 mL) and saturated ammonium chloride (50 mL) were added and the mixture was stirred overnight at ambient temperature. The layers were separated, and the organic layer was washed with 1M ammonium hydroxide (2×50 mL), 1N sodium hydroxide (2×50 mL), 1N hydrochloric acid (2×50 mL), and saturated sodium chloride (50 mL). The ethyl acetate was dried over $MgSO_4$ and concentrated in vacuo. The crude product was chromatographed on silica gel using ethyl acetate/hexane (1:4) as eluent to afford the title compound (66 mg). mp=116° C. Elemental analysis calcd. for $C_{18}H_{23}N_2O_3Cl$: C, 61.62; H, 6.618; N, 7.98. Found: C, 61.45; H, 6.44; N, 7.77.

Various analogs synthesized using Schemes 1, 2 and 3 are listed in Table 1.

TABLE 1

| Ex No | $R^1$ | $R^3$ | Y | Ar | mp/° C. |
|---|---|---|---|---|---|
| 1 | Cl | $Et_2CH$ | NH | 2-Br-4-iPr-phenyl | 118.5 |
| 2 | Cl | $Et_2CH$ | NEt | 2-Br-4-iPr-phenyl | MS = 440 |
| 3 | Cl | $Et_2CH$ | NH | 2,4-$Br_2$-phenyl | 155.5 |
| 4 | Cl | $Et_2CH$ | NEt | 2,4-$Br_2$-phenyl | 88.1 |
| 5 | Cl | $Et_2CH$ | NH | 2,4,6-$Me_3$-phenyl | 180.8 |
| 6 | Cl | $Et_2CH$ | NEt | 2,4,6-$Me_3$-phenyl | 93.8 |
| 7 | Cl | $MeOCH_2(Et)CH$ | NH | 2,4,6-$Me_3$-phenyl | 153.8 |
| 8 | Cl | $Et_2CH$ | NH | 2-Br-4,6-$(MeO)_2$-phenyl | 181.3 |
| 9 | Cl | $Et_2CH$ | NH | 2-CN-4,6-$Me_2$-phenyl | 174.0 |
| 10 | Cl | $MeOCH_2(Et)CH$ | NH | 2-Br-4,6-$(MeO)_2$-phenyl | 175.8 |
| 11 | Cl | $MeOCH_2(Et)CH$ | NH | 2-Cl-4,6-$(MeO)_2$-phenyl | |
| 12 | Cl | $MeOCH_2(Et)CH$ | NH | 2-I-4,6-$Me_2$-phenyl | 109.4 |
| 13 | Cl | $MeOCH_2(Et)CH$ | NH | 2-CN-4,6-$Me_2$-phenyl | |
| 14 | Cl | $MeOCH_2(Et)CH$ | NH | 2-Br-4,6-$Me_2$-phenyl | |
| 15 | Cl | $MeOCH_2(Et)CH$ | NH | 4-Br-2,6-$Me_2$-phenyl | 152.8 |
| 16 | Cl | $MeOCH_2(Et)CH$ | NH | 4-MeCO-2,6-$Me_2$-phenyl | 127.1 |
| 16a | Cl | $MeOCH_2(Et)CH$ | NH | 4-MeCO-2-OMe-6-Me-phenyl | 179.8 |
| 17 | Cl | $MeOCH_2(Et)CH$ | NH | 2-MeCO-4,6-$Me_2$-phenyl | |
| 18 | Cl | $MeOCH_2(Et)CH$ | NH | 4,6-$Me_2$-2-SMe-phenyl | |
| 19 | Cl | $MeOCH_2(Et)CH$ | NH | 4,6-$Me_2$-2-$SO_2$Me-phenyl | |
| 20 | Cl | $MeOCH_2(Et)CH$ | NH | 4-Cl-2-I-6-Me-phenyl | 121.8 |
| 21 | Cl | $(MeOCH_2)_2CH$ | NH | 2,4,6-$Me_3$-phenyl | 127.2 |
| 22 | Cl | phenyl | NH | 2,4,6-$Me_3$-phenyl | |
| 23 | CN | $MeOCH_2(Et)CH$ | NH | 2,4,6-$Me_3$-phenyl | |
| 24 | $CONH_2$ | $MeOCH_2(Et)CH$ | NH | 2,4,6-$Me_3$-phenyl | |
| 25 | COOH | $MeOCH_2(Et)CH$ | NH | 2,4,6-$Me_3$-phenyl | |
| 26 | CHO | $MeOCH_2(Et)CH$ | NH | 2,4,6-$Me_3$-phenyl | |
| 27 | $CH_2OH$ | $MeOCH_2(Et)CH$ | NH | 2,4,6-$Me_3$-phenyl | |
| 28 | $CH_3$ | $MeOCH_2(Et)CH$ | NH | 2,4-$Br_2$-phenyl | |
| 29 | $CH_3$ | $MeOCH_2(Et)CH$ | NH | 2-Br-4-iPr-phenyl | |
| 30 | $CH_3$ | $MeOCH_2(Et)CH$ | NH | 2,4,6-$Me_3$-phenyl | |
| 30a | $CH_3$ | $MeOCH_2(Et)CH$ | NH | 2-Cl-4,6-$Me_2$-phenyl | 117.9 |
| 31 | $CH_3$ | $(MeOCH_2)_2CH$ | NH | 2,4,6-$Me_3$-phenyl | |
| 32 | $CH_3$ | $(MeOCH_2)_2CH$ | NH | 2,4-$Cl_2$-6-Me-phenyl | |
| 33 | Cl | $(MeOCH_2)_2CH$ | NH | 2,4-$Cl_2$-6-Me-phenyl | |
| 34 | Cl | $(MeOCH_2)_2CH$ | NH | 2,4-$Br_2$-6-Me-phenyl | |
| 35 | $CH_3$ | $MeOC_2H_4(MeOCH_2)CH$ | NH | 2,4,6-$Me_3$-phenyl | |
| 36 | Cl | $MeOC_2H_4(MeOCH_2)CH$ | NH | 2,4,6-$Me_3$-phenyl | 120.0 |
| 36a | Cl | $MeOC_2H_4(MeOCH_2)CH$ | NH | 4-Br-2-OMe-6-Me-phenyl | 130.9 |
| 37 | Cl | $(MeOC_2H_4)_2CH$ | NH | 2,4,6-$Me_3$-phenyl | |
| 38 | Cl | $MeOCH_2(Et)CH$ | NH | 2,4-$Me_2$-6-MeO-phenyl | |
| 39 | Cl | $MeOC_2H_4(MeOCH_2)CH$ | NH | 2,4-$Me_2$-6-MeO-phenyl | |
| 40 | $CH_3$ | $MeOC_2H_4(MeOCH_2)CH$ | NH | 2,4-$Me_2$-6-MeO-phenyl | |
| 41 | $CH_3$ | $MeOC_2H_4(MeOCH_2)CH$ | NH | 4-Br-2,6-$Me_2$-phenyl | |
| 42 | $CH_3$ | $MeOC_2H_4(MeOCH_2)CH$ | NH | 2-Cl-4,6-$Me_2$-phenyl | |
| 43 | $CH_3$ | $MeOC_2H_4(MeOCH_2)CH$ | NH | 2,4-$Me_2$-6-$MeOCH_2$-phenyl | |
| 44 | $CH_3$ | $(MeOCH_2)_2CH$ | NH | 2,4-$Me_2$-6-MeO-phenyl | |
| 45 | $CH_3$ | $(MeOCH_2)_2CH$ | NH | 4-Br-2,6-$Me_2$-phenyl | |
| 45a | $CH_3$ | $(MeOCH_2)_2CH$ | NH | 2-Br-6-F-4-Me-phenyl | 138.9 |
| 46 | $CH_3$ | $(MeOCH_2)_2CH$ | NH | 2-Cl-4,6-$Me_2$-phenyl | |
| 46a | $CH_3$ | $(MeOCH_2)_2CH$ | NH | 2-Cl-4-OMe-6-Me-phenyl | 128.3 |
| 47 | $CH_3$ | $(MeOCH_2)_2CH$ | NH | 2,4-$Me_2$-6-$MeOCH_2$-phenyl | |
| 48 | Cl | $MeOC_2H_4(MeOCH_2)CH$ | NH | 2,4-$Me_2$-6-MeO-phenyl | |
| 49 | Cl | $MeOC_2H_4(MeOCH_2)CH$ | NH | 4-Br-2,6-$Me_2$-phenyl | 138.6 |
| 50 | Cl | $MeOC_2H_4(MeOCH_2)CH$ | NH | 2-Cl-4,6-$Me_2$-phenyl | |
| 51 | Cl | $MeOC_2H_4(MeOCH_2)CH$ | NH | 2,4-$Me_2$-6-$MeOCH_2$-phenyl | |
| 52 | Cl | $(MeOCH_2)_2CH$ | NH | 2,4-$Me_2$-6-MeO-phenyl | |
| 53 | Cl | $(MeOCH_2)_2CH$ | NH | 4-Br-2,6-$Me_2$-phenyl | 152.1 |
| 54 | Cl | $(MeOCH_2)_2CH$ | NH | 2-Cl-4,6-$Me_2$-phenyl | 132.8 |
| 55 | Cl | $(MeOCH_2)_2CH$ | NH | 2,4-$Me_2$-6-$MeOCH_2$-phenyl | |
| 56 | Cl | $MeOCH_2(Me)CH$ | NH | 2,4-$Me_2$-6-MeO-phenyl | |
| 57 | Cl | $MeOCH_2(Me)CH$ | NH | 4-Br-2,6-$Me_2$-phenyl | |

TABLE 1-continued

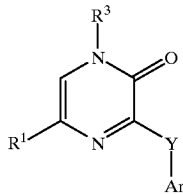

| Ex No | R¹ | R³ | Y | Ar | mp/° C. |
|---|---|---|---|---|---|
| 58 | Cl | EtOCH₂(Et)CH | NH | 4-Br-2,6-Me₂-phenyl | |
| 59 | Cl | EtOCH₂(Me)CH | NH | 4-Br-2,6-Me₂-phenyl | |
| 60 | Cl | MeOCH₂(Et)CH | NH | 4-Br-2,6-F₂-phenyl | |
| 61 | CH₃ | MeOC₂H₄(MeOCH₂)CH | NH | 2-Br-4,6-Me₂-phenyl | |
| 62 | CH₃ | MeOC₂H₄(MeOCH₂)CH | NH | 2,4-Me₂-6-SMe-phenyl | |
| 63 | CH₃ | MeOC₂H₄(MeOCH₂)CH | NH | 2,4-Me₂-6-SO₂Me-phenyl | |
| 64 | CH₃ | MeOC₂H₄(MeOCH₂)CH | NH | 4-NMe₂-2,6-Me₂-phenyl | |
| 65 | CH₃ | MeOC₂H₄(MeOCH₂)CH | NH | 2,4-Cl₂-6-Me-phenyl | |
| 66 | CH₃ | MeOC₂H₄(MeOCH₂)CH | NH | 4-Cl-2,6-Me₂-phenyl | |
| 67 | CH₃ | MeOC₂H₄(MeOCH₂)CH | NH | 2,6-Me₂-4-SMe-phenyl | |
| 68 | CH₃ | MeOC₂H₄(MeOCH₂)CH | NH | 2,6-Me₂-4-OMe-phenyl | |
| 69 | CH₃ | MeOC₂H₄(MeOCH₂)CH | NH | 2, 6-Me₂-4-SO₂Me-phenyl | |
| 70 | CH₃ | MeOC₂H₄(MeOCH₂)CH | NH | 4-MeC(O)-2,6-Me₂-phenyl | |
| 71 | CH₃ | (MeOCH₂)₂CH | NH | 4-Br-2,6-Me₂-phenyl | |
| 72 | CH₃ | (MeOCH₂)₂CH | NH | 4-MeC(O)-2,6-Me₂-phenyl | |
| 73 | CH₃ | (MeOCH₂)₂CH | NH | 2,6-Me₂-4-SMe-phenyl | |
| 74 | CH₃ | (MeOCH₂)₂CH | NH | 2,6-Me₂-4-SO₂Me-phenyl | |
| 75 | CH₃ | (MeOCH₂)₂CH | NH | 4-NMe₂-2,6-Me₂-phenyl | |
| 76 | CH₃ | (MeOCH₂)₂CH | NH | 2-NMe₂-4,6-Me₂-phenyl | |
| 77 | Cl | MeOCH₂(Et)CH | NH | 2,6-Me₂-4-SMe-phenyl | 104.9 |
| 78 | Cl | MeOCH₂(Et)CH | NH | 2,6-Me₂-4-SO₂Me-phenyl | |
| 79 | Cl | MeOCH₂(Et)CH | NH | 2-Cl-4,6-Me₂-phenyl | 116.7 |
| 80 | Cl | MeOCH₂(Et)CH | NH | 4-Br-6-OMe-2-Me-phenyl | 147.8 |
| 81 | Cl | (MeOCH₂)₂CH | NH | 2,6-Me₂-4-SMe-phenyl | 158.9 |
| 82 | Cl | (MeOCH₂)₂CH | NH | 2,6-Me₂-4-SO₂Me-phenyl | |
| 83 | Cl | (MeOCH₂)₂CH | NH | 4-Br-6-OMe-2-Me-phenyl | 175.5 |
| 84 | CH₃ | Et₂CH | NH | 2,4,6-Me₃-phenyl | 109 |
| 84a | CH₃ | Et₂CH | NH | 2-Cl-4,6-Me₂-phenyl | 133.8 |
| 84b | CH₃ | Et₂CH | NH | 2-Cl-4-OMe-6-Me-phenyl | 121.9 |
| 84c | CH₂CH₃ | Et₂CH | NH | 2,4,6-Me₃-phenyl | 79.3 |
| 84d | CH₂CH₃ | Et₂CH | NH | 2-Cl-4,6-Me₂-phenyl | 95.6 |
| 85 | Br | Et₂CH | NH | 2,4,6-Me₃-phenyl | MS = 378 |
| 86 | Br | Et₂CH | NH | 2-Br-4-iPr-phenyl | |
| 87 | Br | Et₂CH | NEt | 2-Br-4-iPr-phenyl | |
| 88 | Br | Et₂CH | NH | 2,4-Br₂-phenyl | |
| 89 | Br | Et₂CH | NEt | 2,4-Br₂-phenyl | |
| 90 | Br | Et₂CH | NEt | 2,4,6-Me₃-phenyl | |
| 91 | Br | Et₂CH | NEt | 2,4,6-Me₃-phenyl | |
| 92 | Br | MeOCH₂(Et)CH | NH | 2,4,6-Me₃-phenyl | |
| 93 | Br | Et₂CH | NH | 2-Br-4,6-(MeO)₂-phenyl | |
| 94 | Br | Et₂CH | NH | 2-CN-4,6-Me₂-phenyl | |
| 95 | Br | MeOCH₂(Et)CH | NH | 2-Br-4,6-(MeO)₂-phenyl | |
| 96 | Br | MeOCH₂(Et)CH | NH | 2-I-4,6-Me₂-phenyl | |
| 97 | Br | MeOCH₂(Et)CH | NH | 2,6-Me₂-4-Br-phenyl | |
| 98 | Br | MeOCH₂(Et)CH | NH | 2-I-4-Cl-6-Me-phenyl | |
| 99 | Br | (MeOCH₂)₂CH | NH | 2,4,6-Me₃-phenyl | |
| 100 | Br | MeOCH₂(Et)CH | NH | 2,6-Me₂-4-SMe-phenyl | |
| 101 | Br | MeOCH₂(Et)CH | NH | 2,6-Me₂-4-SO₂Me-phenyl | |
| 102 | Br | MeOCH₂(Et)CH | NH | 2-Cl-4,6-Me₂-phenyl | |
| 103 | Br | MeOCH₂(Et)CH | NH | 2-Me-4-Br-6-OMe-phenyl | |
| 104 | CH₃ | Et₂CH | NH | 2,4,6-Me₃-pyrid-3-yl | |
| 105 | CH₃ | Et₂CH | NH | 4,6-Me₂-pyrid-3-yl | |
| 106 | CH₃ | Et₂CH | NH | 2-Br-6-Me-pyrid-3-yl | |
| 107 | CH₃ | Et₂CH | NH | 2-Br-6-OMe-pyrid-3-yl | |
| 108 | CH₃ | Et₂CH | NH | 2,6-Me₂-pyrid-3-yl | |
| 109 | CH₃ | Et₂CH | NH | 2-Cl-6-Me-pyrid-3-yl | |
| 110 | CH₃ | Et₂CH | NH | 2-Cl-6-OMe-pyrid-3-yl | |
| 111 | CH₃ | MeOCH₂(Et)CH | NH | 2,4,6-Me₃-pyrid-3-yl | |
| 112 | CH₃ | MeOCH₂(Et)CH | NH | 4,6-Me₂-pyrid-3-yl | |
| 113 | CH₃ | MeOCH₂(Et)CH | NH | 2-Br-6-Me-pyrid-3-yl | |
| 114 | CH₃ | (MeOCH₂)₂CH | NH | 2-Br-6-OMe-pyrid-3-yl | |
| 115 | CH₃ | (MeOCH₂)₂CH | NH | 2,6-Me₂-pyrid-3-yl | |
| 116 | CH₃ | (MeOCH₂)₂CH | NH | 2-Cl-6-Me-pyrid-3-yl | |
| 117 | CH₃ | (MeOCH₂)₂CH | NH | 2-Cl-6-OMe-pyrid-3-yl | |
| 118 | CH₃ | MeOCH₂(Et)CH | NH | 2-Br-6-OMe-pyrid-3-yl | |

TABLE 1-continued

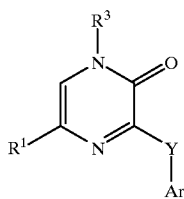

| Ex No | R¹ | R³ | Y | Ar | mp/° C. |
|---|---|---|---|---|---|
| 119 | CH₃ | MeOCH₂(Et)CH | NH | 2,6-Me₂-pyrid-3-yl | |
| 120 | CH₃ | MeOCH₂(Et)CH | NH | 2-Cl-6-Me-pyrid-3-yl | |
| 121 | CH₃ | MeOCH₂(Et)CH | NH | 2-Cl-6-OMe-pyrid-3-yl | |
| 120 | CH₃ | (MeOCH₂)₂CH | NH | 2,4,6-Me₃-pyrid-3-yl | |
| 123 | CH₃ | (MeOCH₂)₂CH | NH | 4,6-Me₂-pyrid-3-yl | |
| 124 | CH₃ | (MeOCH₂)₂CH | NH | 2-Br-6-Me-pyrid-3-yl | |
| 125 | Cl | Et₂CH | NH | 2-Br-6-OMe-pyrid-3-yl | |
| 124 | Cl | Et₂CH | NH | 2,6-Me₂-pyrid-3-yl | |
| 127 | Cl | Et₂CH | NH | 2-Cl-6-Me-pyrid-3-yl | |
| 128 | Cl | Et₂CH | NH | 2-Cl-6-OMe-pyrid-3-yl | |
| 129 | Cl | MeOCH₂(Et)CH | NH | 2,4,6-Me₃-pyrid-3-yl | |
| 130 | Cl | MeOCH₂(Et)CH | NH | 4,6-Me₂-pyrid-3-yl | |
| 131 | Cl | MeOCH₂(Et)CH | NH | 2-Br-6-Me-pyrid-3-yl | |
| 132 | Cl | Et₂CH | NH | 2,4,6-Me₃-pyrid-3-yl | |
| 133 | Cl | Et₂CH | NH | 4,6-Me₂-pyrid-3-yl | |
| 134 | Cl | Et₂CH | NH | 2-Br-6-Me-pyrid-3-yl | |
| 135 | Cl | MeOCH₂(Et)CH | NH | 2-Br-6-OMe-pyrid-3-yl | |
| 136 | Cl | MeOCH₂(Et)CH | NH | 2,6-Me₂-pyrid-3-yl | |
| 137 | Cl | MeOCH₂(Et)CH | NH | 2-Cl-6-Me-pyrid-3-yl | |
| 138 | Cl | MeOCH₂(Et)CH | NH | 2-Cl-6-OMe-pyrid-3-yl | |
| 139 | Cl | (MeOCH₂)₂CH | NH | 2-Br-6-OMe-pyrid-3-yl | |
| 140 | Cl | (MeOCH₂)₂CH | NH | 2,6-Me₂-pyrid-3-yl | |
| 141 | Cl | (MeOCH₂)₂CH | NH | 2-Cl-6-Me-pyrid-3-yl | |
| 142 | Cl | (MeOCH₂)₂CH | NH | 2-Cl-6-OMe-pyrid-3-yl | |
| 143 | Cl | (MeOCH₂)₂CH | NH | 2,4,6-Me₃-pyrid-3-yl | |
| 144 | Cl | (MeOCH₂)₂CH | NH | 4,6-Me₂-pyrid-3-yl | |
| 145 | Cl | (MeOCH₂)₂CH | NH | 2-Br-6-Me-pyrid-3-yl | |
| 146 | Et₂CH | CH₃ | NH | 2,4,6-Me₃-phenyl | |
| 147 | Et₂CH | CH₃ | NH | 2,6-Me₂-4-Br-phenyl | |
| 148 | Et₂CH | CH₃ | NH | 2-Br-4-iPr-phenyl | |
| 149 | MeOCH₂(Et)CH | CH₃ | NH | 2,4,6-Me₃-phenyl | |
| 150 | MeOCH₂(Et)CH | CH₃ | NH | 2,6-Me₂-4-Br-phenyl | |
| 151 | MeOCH₂(Et)CH | CH₃ | NH | 2-Cl-4,6-Me₂-phenyl | |
| 152 | (MeOCH₂)₂CH | CH₃ | NH | 2,4,6-Me₃-phenyl | |
| 153 | (MeOCH₂)₂CH | CH₃ | NH | 2,6-Me₂-4-Br-phenyl | |
| 154 | (MeOCH₂)₂CH | CH₃ | NH | 2-Cl-4,6-Me₂-phenyl | |
| 155 | Et₂CH | CH₃ | NH | 2-Br-4,6-(MeO)₂-phenyl | |
| 156 | Et₂CH | CH₃ | NH | 2-Cl-4,6-Me₂-phenyl | |
| 400 | CH₃ | Me(Et)CH | NH | 2,4,6-Me₃-phenyl | |
| 401 | CH₃ | Me(Et)CH | NH | 2-Cl-4,6-Me₂-phenyl | |
| 402 | CH₃ | Me(Et)CH | NH | 2,4-Cl₂-6-Me-phenyl | |
| 403 | CH₃ | Me(Et)CH | NH | 2,4,6-Cl₃-phenyl | |
| 404 | CH₃ | Me(Et)CH | NH | 2-Me-4-MeO-phenyl | |
| 405 | CH₃ | Me(Et)CH | NH | 2-Cl-4-MeO-phenyl | |
| 406 | CH₃ | Me(Et)CH | NH | 2,4,6-Me₃-5-F-phenyl | |
| 407 | CH₃ | Me(Et)CH | NH | 2,5-Me₂-4-MeO-phenyl | |
| 408 | CH₃ | Me(Et)CH | NH | 2,4-Me₂-6-MeO-phenyl | |
| 409 | CH₃ | Me(Et)CH | NH | 2,6-Cl₂-4-Me-phenyl | |
| 410 | CH₃ | Me(Et)CH | NH | 2,4-Cl₂-phenyl | |
| 411 | CH₃ | Me(Et)CH | NH | 2-Cl-4-Me-phenyl | |
| 412 | CH₃ | Me(Et)CH | NH | 2-Me-4-Cl-phenyl | |
| 413 | CH₃ | Me(Et)CH | NH | 2-NMe₂-6-Me-pyrid-5-yl | |
| 414 | CH₃ | Me(Et)CH | NH | 2-NMe₂-4-Me-pyrid-5-yl | |
| 415 | CH₃ | Me(Et)CH | NH | 2-Cl-4-MeO-6-Me-phenyl | |
| 416 | CH₃ | Me(Et)CH | NH | 2-Cl-4,6-Me₂-5-F-phenyl | |
| 417 | CH₃ | Me(Et)CH | NH | 6-Cl-2,3-dihydro-benzofuran-5-yl | |
| 418 | CH₃ | Me(Et)CH | NH | 6-Me-2,3-dihydro-benzofuran-5-yl | |
| 419 | CH₃ | Me(n-Pr)CH | NH | 2,4,6-Me₃-phenyl | |
| 420 | CH₃ | Me(n-Pr)CH | NH | 2-Cl-4,6-Me₂-phenyl | |
| 421 | CH₃ | Me(n-Pr)CH | NH | 2,4-Cl₂-6-Me-phenyl | |
| 422 | CH₃ | Me(n-Pr)CH | NH | 2,4,6-Cl₃-phenyl | |
| 423 | CH₃ | Me(n-Pr)CH | NH | 2-Me-4-MeO-phenyl | |
| 424 | CH₃ | Me(n-Pr)CH | NH | 2-Cl-4-MeO-phenyl | |
| 425 | CH₃ | Me(n-Pr)CH | NH | 2,4,6-Me₃-5-F-phenyl | |
| 426 | CH₃ | Me(n-Pr)CH | NH | 2,5-Me₂-4-MeO-phenyl | |

TABLE 1-continued

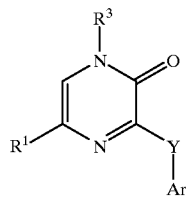

| Ex No | R¹ | R³ | Y | Ar | mp/° C. |
|---|---|---|---|---|---|
| 427 | CH₃ | Me(n-Pr)CH | NH | 2,4-Me₂-6-MeO-phenyl | |
| 428 | CH₃ | Me(n-Pr)CH | NH | 2,6-Cl₂-4-Me-phenyl | |
| 429 | CH₃ | Me(n-Pr)CH | NH | 2,4-Cl₂-phenyl | |
| 430 | CH₃ | Me(n-Pr)CH | NH | 2-Cl-4-Me-phenyl | |
| 431 | CH₃ | Me(n-Pr)CH | NH | 2-Me-4-Cl-phenyl | |
| 432 | CH₃ | Me(n-Pr)CH | NH | 2-NMe₂-6-Me-pyrid-5-yl | |
| 433 | CH₃ | Me(n-Pr)CH | NH | 2-NMe₂-4-Me-pyrid-5-yl | |
| 434 | CH₃ | Me(n-Pr)CH | NH | 2-Cl-4-MeO-6-Me-phenyl | |
| 435 | CH₃ | Me(n-Pr)CH | NH | 2-Cl-4,6-Me₂-5-F-phenyl | |
| 436 | CH₃ | Me(n-Pr)CH | NH | 6-Cl-2,3-dihydro-benzofuran-5-yl | |
| 437 | CH₃ | Me(n-Pr)CH | NH | 6-Me-2,3-dihydro-benzofuran-5-yl | |
| 438 | CH₃ | Et₂CH | NH | 2,4-Cl₂-6-Me-phenyl | |
| 439 | CH₃ | Et₂CH | NH | 2,4,6-Cl₃-phenyl | |
| 440 | CH₃ | Et₂CH | NH | 2-Me-4-MeO-phenyl | |
| 441 | CH₃ | Et₂CH | NH | 2-Cl-4-MeO-phenyl | |
| 442 | CH₃ | Et₂CH | NH | 2,4,6-Me₃-5-F-phenyl | |
| 443 | CH₃ | Et₂CH | NH | 2,5-Me₂-4-MeO-phenyl | |
| 444 | CH₃ | Et₂CH | NH | 2,4-Me₂-6-MeO-phenyl | |
| 445 | CH₃ | Et₂CH | NH | 2,6-Cl₂-4-Me-phenyl | |
| 446 | CH₃ | Et₂CH | NH | 2,4-Cl₂-phenyl | |
| 447 | CH₃ | Et₂CH | NH | 2-Cl-4-Me-phenyl | |
| 448 | CH₃ | Et₂CH | NH | 2-Me-4-Cl-phenyl | |
| 449 | CH₃ | Et₂CH | NH | 2-NMe₂-6-Me-pyrid-5-yl | |
| 450 | CH₃ | Et₂CH | NH | 2-NMe₂-4-Me-pyrid-5-yl | |
| 451 | CH₃ | Et₂CH | NH | 2-Cl-4,6-Me₂-5-F-phenyl | |
| 452 | CH₃ | Et₂CH | NH | 6-Cl-2,3-dihydro-benzofuran-5-yl | |
| 453 | CH₃ | Et₂CH | NH | 6-Me-2,3-dihydro-benzofuran-5-yl | |
| 454 | CH₃ | (c-Pr)₂CH | NH | 2,4,6-Me₃-phenyl | |
| 455 | CH₃ | (c-Pr)₂CH | NH | 2-Cl-4,6-Me₂-phenyl | |
| 456 | CH₃ | (c-Pr)₂CH | NH | 2,4-Cl₂-6-Me-phenyl | |
| 457 | CH₃ | (c-Pr)₂CH | NH | 2,4,6-Cl₃-phenyl | |
| 458 | CH₃ | (c-Pr)₂CH | NH | 2-Me-4-MeO-phenyl | |
| 459 | CH₃ | (c-Pr)₂CH | NH | 2-Cl-4-MeO-phenyl | |
| 460 | CH₃ | (c-Pr)₂CH | NH | 2,4,6-Me₃-5-F-phenyl | |
| 461 | CH₃ | (c-Pr)₂CH | NH | 2,5-Me₂-4-MeO-phenyl | |
| 462 | CH₃ | (c-Pr)₂CH | NH | 2,4-Me₂-6-MeO-phenyl | |
| 463 | CH₃ | (c-Pr)₂CH | NH | 2,6-Cl₂-4-Me-phenyl | |
| 464 | CH₃ | (c-Pr)₂CH | NH | 2,4-Cl₂-phenyl | |
| 465 | CH₃ | (c-Pr)₂CH | NH | 2-Cl-4-Me-phenyl | |
| 466 | CH₃ | (c-Pr)₂CH | NH | 2-Me-4-Cl-phenyl | |
| 467 | CH₃ | (c-Pr)₂CH | NH | 2-NMe₂-6-Me-pyrid-5-yl | |
| 468 | CH₃ | (c-Pr)₂CH | NH | 2-NMe₂-4-Me-pyrid-5-yl | |
| 469 | CH₃ | (c-Pr)₂CH | NH | 2-Cl-4-MeO-6-Me-phenyl | |
| 470 | CH₃ | (c-Pr)₂CH | NH | 2-Cl-4,6-Me₂-5-F-phenyl | |
| 471 | CH₃ | (c-Pr)₂CH | NH | 6-Cl-2,3-dihydro-benzofuran-5-yl | |
| 472 | CH₃ | (c-Pr)₂CH | NH | 6-Me-2,3-dihydro-benzofuran-5-yl | |
| 473 | CH₃ | c-Pr(Me)CH | NH | 2,4,6-Me₃-phenyl | |
| 474 | CH₃ | c-Pr(Me)CH | NH | 2-Cl-4,6-Me₂-phenyl | |
| 475 | CH₃ | c-Pr(Me)CH | NH | 2,4-Cl₂-6-Me-phenyl | |
| 476 | CH₃ | c-Pr(Me)CH | NH | 2,4,6-Cl₃-phenyl | |
| 477 | CH₃ | c-Pr(Me)CH | NH | 2-Me-4-MeO-phenyl | |
| 478 | CH₃ | c-Pr(Me)CH | NH | 2-Cl-4-MeO-phenyl | |
| 479 | CH₃ | c-Pr(Me)CH | NH | 2,4,6-Me₃-5-F-phenyl | |
| 480 | CH₃ | c-Pr(Me)CH | NH | 2,5-Me₂-4-MeO-phenyl | |
| 481 | CH₃ | c-Pr(Me)CH | NH | 2,4-Me₂-6-MeO-phenyl | |
| 482 | CH₃ | c-Pr(Me)CH | NH | 2,6-Cl₂-4-Me-phenyl | |
| 483 | CH₃ | c-Pr(Me)CH | NH | 2,4-Cl₂-phenyl | |
| 484 | CH₃ | c-Pr(Me)CH | NH | 2-Cl-4-Me-phenyl | |
| 485 | CH₃ | c-Pr(Me)CH | NH | 2-Me-4-Cl-phenyl | |
| 486 | CH₃ | c-Pr(Me)CH | NH | 2-NMe₂-6-Me-pyrid-5-yl | |
| 487 | CH₃ | c-Pr(Me)CH | NH | 2-NMe₂-4-Me-pyrid-5-yl | |
| 488 | CH₃ | c-Pr(Me)CH | NH | 2-Cl-4-MeO-6-Me-phenyl | |
| 489 | CH₃ | c-Pr(Me)CH | NH | 2-Cl-4,6-Me₂-5-F-phenyl | |
| 490 | CH₃ | c-Pr(Me)CH | NH | 6-Cl-2,3-dihydro-benzofuran-5-yl | |
| 491 | CH₃ | c-Pr(Me)CH | NH | 6-Me-2,3-dihydro-benzofuran-5-yl | |

TABLE 1-continued

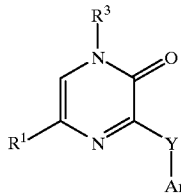

| Ex No | R$^1$ | R$^3$ | Y | Ar | mp/° C. |
|---|---|---|---|---|---|
| 492 | CH$_3$ | c-Pr(Et)CH | NH | 2,4,6-Me$_3$-phenyl | |
| 493 | CH$_3$ | c-Pr(Et)CH | NH | 2-Cl-4,6-Me$_2$-phenyl | |
| 494 | CH$_3$ | c-Pr(Et)CH | NH | 2,4-Cl$_2$-6-Me-phenyl | |
| 495 | CH$_3$ | c-Pr(Et)CH | NH | 2,4,6-Cl$_3$-phenyl | |
| 496 | CH$_3$ | c-Pr(Et)CH | NH | 2-Me-4-MeO-phenyl | |
| 497 | CH$_3$ | c-Pr(Et)CH | NH | 2-Cl-4-MeO-phenyl | |
| 498 | CH$_3$ | c-Pr(Et)CH | NH | 2,4,6-Me$_3$-5-F-phenyl | |
| 499 | CH$_3$ | c-Pr(Et)CH | NH | 2,5-Me$_2$-4-MeO-phenyl | |
| 500 | CH$_3$ | c-Pr(Et)CH | NH | 2,4-Me$_2$-6-MeO-phenyl | |
| 501 | CH$_3$ | c-Pr(Et)CH | NH | 2,6-Cl$_2$-4-Me-phenyl | |
| 502 | CH$_3$ | c-Pr(Et)CH | NH | 2,4-Cl$_2$-phenyl | |
| 503 | CH$_3$ | c-Pr(Et)CH | NH | 2-Cl-4-Me-phenyl | |
| 504 | CH$_3$ | c-Pr(Et)CH | NH | 2-Me-4-Cl-phenyl | |
| 505 | CH$_3$ | c-Pr(Et)CH | NH | 2-NMe$_2$-6-Me-pyrid-5-yl | |
| 506 | CH$_3$ | c-Pr(Et)CH | NH | 2-NMe$_2$-4-Me-pyrid-5-yl | |
| 507 | CH$_3$ | c-Pr(Et)CH | NH | 2-Cl-4-MeO-6-Me-phenyl | |
| 508 | CH$_3$ | c-Pr(Et)CH | NH | 2-Cl-4,6-Me$_2$-5-F-phenyl | |
| 509 | CH$_3$ | c-Pr(Et)CH | NH | 6-Cl-2,3-dihydro-benzofuran-5-yl | |
| 510 | CH$_3$ | c-Pr(Et)CH | NH | 6-Me-2,3-dihydro-benzofuran-5-yl | |
| 511 | CH$_3$ | c-Pr(n-Pr)CH | NH | 2,4,6-Me$_3$-phenyl | |
| 512 | CH$_3$ | c-Pr(n-Pr)CH | NH | 2-Cl-4,6-Me$_2$-phenyl | |
| 513 | CH$_3$ | c-Pr(n-Pr)CH | NH | 2,4-Cl$_2$-6-Me-phenyl | |
| 514 | CH$_3$ | c-Pr(n-Pr)CH | NH | 2,4,6-Cl$_3$-phenyl | |
| 515 | CH$_3$ | c-Pr(n-Pr)CH | NH | 2-Me-4-MeO-phenyl | |
| 516 | CH$_3$ | c-Pr(n-Pr)CH | NH | 2-Cl-4-MeO-phenyl | |
| 517 | CH$_3$ | c-Pr(n-Pr)CH | NH | 2,4,6-Me$_3$-5-F-phenyl | |
| 518 | CH$_3$ | c-Pr(n-Pr)CH | NH | 2,5-Me$_2$-4-MeO-phenyl | |
| 519 | CH$_3$ | c-Pr(n-Pr)CH | NH | 2,4-Me$_2$-6-MeO-phenyl | |
| 520 | CH$_3$ | c-Pr(n-Pr)CH | NH | 2,6-Cl$_2$-4-Me-phenyl | |
| 521 | CH$_3$ | c-Pr(n-Pr)CH | NH | 2,4-Cl$_2$-phenyl | |
| 522 | CH$_3$ | c-Pr(n-Pr)CH | NH | 2-Cl-4-Me-phenyl | |
| 523 | CH$_3$ | c-Pr(n-Pr)CH | NH | 2-Me-4-Cl-phenyl | |
| 524 | CH$_3$ | c-Pr(n-Pr)CH | NH | 2-NMe$_2$-6-Me-pyrid-5-yl | |
| 525 | CH$_3$ | c-Pr(n-Pr)CH | NH | 2-NMe$_2$-4-Me-pyrid-5-yl | |
| 526 | CH$_3$ | c-Pr(n-Pr)CH | NH | 2-Cl-4-MeO-6-Me-phenyl | |
| 527 | CH$_3$ | c-Pr(n-Pr)CH | NH | 2-Cl-4,6-Me$_2$-5-F-phenyl | |
| 528 | CH$_3$ | c-Pr(n-Pr)CH | NH | 6-Cl-2,3-dihydro-benzofuran-5-yl | |
| 529 | CH$_3$ | c-Pr(n-Pr)CH | NH | 6-Me-2,3-dihydro-benzofuran-5-yl | |
| 530 | CH$_3$ | c-Pr(n-Bu)CH | NH | 2,4,6-Me$_3$-phenyl | |
| 531 | CH$_3$ | c-Pr(n-Bu)CH | NH | 2-Cl-4,6-Me$_2$-phenyl | |
| 532 | CH$_3$ | c-Pr(n-Bu)CH | NH | 2,4-Cl$_2$-6-Me-phenyl | |
| 533 | CH$_3$ | c-Pr(n-Bu)CH | NH | 2,4,6-Cl$_3$-phenyl | |
| 534 | CH$_3$ | c-Pr(n-Bu)CH | NH | 2-Me-4-MeO-phenyl | |
| 535 | CH$_3$ | c-Pr(n-Bu)CH | NH | 2-Cl-4-MeO-phenyl | |
| 536 | CH$_3$ | c-Pr(n-Bu)CH | NH | 2,4,6-Me$_3$-5-F-phenyl | |
| 537 | CH$_3$ | c-Pr(n-Bu)CH | NH | 2,5-Me$_2$-4-MeO-phenyl | |
| 538 | CH$_3$ | c-Pr(n-Bu)CH | NH | 2,4-Me$_2$-6-MeO-phenyl | |
| 539 | CH$_3$ | c-Pr(n-Bu)CH | NH | 2,6-Cl$_2$-4-Me-phenyl | |
| 540 | CH$_3$ | c-Pr(n-Bu)CH | NH | 2,4-Cl$_2$-phenyl | |
| 541 | CH$_3$ | c-Pr(n-Bu)CH | NH | 2-Cl-4-Me-phenyl | |
| 542 | CH$_3$ | c-Pr(n-Bu)CH | NH | 2-Me-4-Cl-phenyl | |
| 543 | CH$_3$ | c-Pr(n-Bu)CH | NH | 2-NMe$_2$-6-Me-pyrid-5-yl | |
| 544 | CH$_3$ | c-Pr(n-Bu)CH | NH | 2-NMe$_2$-4-Me-pyrid-5-yl | |
| 545 | CH$_3$ | c-Pr(n-Bu)CH | NH | 2-Cl-4-MeO-6-Me-phenyl | |
| 546 | CH$_3$ | c-Pr(n-Bu)CH | NH | 2-Cl-4,6-Me$_2$-5-F-phenyl | |
| 547 | CH$_3$ | c-Pr(n-Bu)CH | NH | 6-Cl-2,3-dihydro-benzofuran-5-yl | |
| 548 | CH$_3$ | c-Pr(n-Bu)CH | NH | 6-Me-2,3-dihydro-benzofuran-5-yl | |
| 549 | CH$_3$ | c-PrCH$_2$(Et)CH | NH | 2,4,6-Me$_3$-phenyl | |
| 550 | CH$_3$ | c-PrCH$_2$(Et)CH | NH | 2-Cl-4,6-Me$_2$-phenyl | |
| 551 | CH$_3$ | c-PrCH$_2$(Et)CH | NH | 2,4-Cl$_2$-6-Me-phenyl | |
| 552 | CH$_3$ | c-PrCH$_2$(Et)CH | NH | 2,4,6-Cl$_3$-phenyl | |
| 553 | CH$_3$ | c-PrCH$_2$(Et)CH | NH | 2-Me-4-MeO-phenyl | |
| 554 | CH$_3$ | c-PrCH$_2$(Et)CH | NH | 2-Cl-4-MeO-phenyl | |
| 555 | CH$_3$ | c-PrCH$_2$(Et)CH | NH | 2,4,6-Me$_3$-5-F-phenyl | |
| 556 | CH$_3$ | c-PrCH$_2$(Et)CH | NH | 2,5-Me$_2$-4-MeO-phenyl | |

TABLE 1-continued

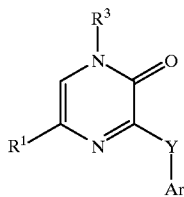

| Ex No | R¹ | R³ | Y | Ar | mp/° C. |
|---|---|---|---|---|---|
| 557 | $CH_3$ | c-$PrCH_2$(Et)CH | NH | 2,4-$Me_2$-6-MeO-phenyl | |
| 558 | $CH_3$ | c-$PrCH_2$(Et)CH | NH | 2,6-$Cl_2$-4-Me-phenyl | |
| 559 | $CH_3$ | c-$PrCH_2$(Et)CH | NH | 2,4-$Cl_2$-phenyl | |
| 560 | $CH_3$ | c-$PrCH_2$(Et)CH | NH | 2-Cl-4-Me-phenyl | |
| 561 | $CH_3$ | c-$PrCH_2$(Et)CH | NH | 2-Me-4-Cl-phenyl | |
| 562 | $CH_3$ | c-$PrCH_2$(Et)CH | NH | 2-$NMe_2$-6-Me-pyrid-5-yl | |
| 563 | $CH_3$ | c-$PrCH_2$(Et)CH | NH | 2-$NMe_2$-4-Me-pyrid-5-yl | |
| 564 | $CH_3$ | c-$PrCH_2$(Et)CH | NH | 2-Cl-4-MeO-6-Me-phenyl | |
| 565 | $CH_3$ | c-$PrCH_2$(Et)CH | NH | 2-Cl-4,6-$Me_2$-5-F-phenyl | |
| 566 | $CH_3$ | c-$PrCH_2$(Et)CH | NH | 6-Cl-2,3-dihydro-benzofuran-5-yl | |
| 567 | $CH_3$ | c-$PrCH_2$(Et)CH | NH | 6-Me-2,3-dihydro-benzofuran-5-yl | |

Compounds that can be synthesized using synthetic Scheme 6 or Scheme 7 are listed in Table 2

TABLE 2

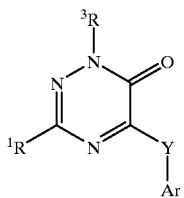

| Ex. No. | R¹ | R³ | Y | Ar | mp |
|---|---|---|---|---|---|
| 200 | $CH_3$ | $Et_2$CH | NH | 2,4-$Br_2$-phenyl | |
| 201 | $CH_3$ | $Et_2$CH | NH | 2-Br-4-iPr-phenyl | |
| 202 | $CH_3$ | $Et_2$CH | NEt | 2,4-$Br_2$-phenyl | |
| 203 | $CH_3$ | $Et_2$CH | NEt | 2-Br-4-iPr-phenyl | |
| 204 | $CH_3$ | $Et_2$CH | NH | 2,4,6-$Me_3$-phenyl | 133 |
| 205 | $CH_3$ | $Et_2$CH | NEt | 2,4,6-$Me_3$-phenyl | |
| 206 | $CH_3$ | $MeOCH_2$(Et)CH | NH | 2,4,6-$Me_3$-phenyl | |
| 207 | $CH_3$ | $Et_2$CH | NH | 2-Br-4,6-$(MeO)_2$-phenyl | |
| 208 | $CH_3$ | $MeOCH_2$(Et)CH | NH | 2-Br-4,6-$(MeO)_2$-phenyl | |
| 209 | $CH_3$ | $MeOCH_2$(Et)CH | NH | 2-Cl-4,6-$(MeO)_2$-phenyl | |
| 210 | $CH_3$ | $MeOCH_2$(Et)CH | NH | 2,4-$Me_2$-6-I-phenyl | |
| 211 | $CH_3$ | $MeOCH_2$(Et)CH | NH | 2-CN-4,6-$Me_2$-phenyl | |
| 212 | $CH_3$ | $MeOCH_2$(Et)CH | NH | 2-Br-4,6-$Me_2$-phenyl | |
| 213 | $CH_3$ | $MeOCH_2$(Et)CH | NH | 4-Br-2,6-$Me_2$-phenyl | |
| 214 | $CH_3$ | $MeOCH_2$(Et)CH | NH | 4-MeC(O)-2,6-$Me_2$-phenyl | |
| 215 | $CH_3$ | $MeOCH_2$(Et)CH | NH | 2-MeC(O)-4,6-$Me_2$-phenyl | |
| 216 | $CH_3$ | $MeOCH_2$(Et)CH | NH | 2,4-$Me_2$-6-SMe-phenyl | |
| 217 | $CH_3$ | $MeOCH_2$(Et)CH | NH | 2,4-$Me_2$-6-$SO_2$Me-phenyl | |
| 218 | $CH_3$ | $MeOCH_2$(Et)CH | NH | 4-Cl-2-I-6-Me-phenyl | |
| 219 | $CH_3$ | $(MeOCH_2)_2$CH | NH | 2,4,6-$Me_3$-phenyl | |
| 220 | $CH_3$ | $Et_2$CH | NH | 2,4,6-$Me_3$-phenyl | |
| 221 | $CH_3$ | $(MeOCH_2)_2$CH | NH | 2,4-$Cl_2$-6-Me-phenyl | |
| 222 | $CH_3$ | $(MeOCH_2)_2$CH | NH | 2,4-$Br_2$-6-Me-phenyl | |
| 223 | $CH_3$ | $MeOC_2H_4(MeOCH_2)$CH | NH | 2,4,6-$Me_3$-phenyl | |
| 224 | $CH_3$ | $(MeOC_2H_4)_2$CH | NH | 2,4,6-$Me_3$-phenyl | |
| 225 | $CH_3$ | $MeOCH_2$(Et)CH | NH | 2,4-$Me_2$-6-MeO-phenyl | |
| 226 | $CH_3$ | $MeOC_2H_4(MeOCH_2)$CH | NH | 2,4-$Me_2$-6-MeO-phenyl | |
| 227 | $CH_3$ | $MeOC_2H_4(MeOCH_2)$CH | NH | 2-Br-4,6-$Me_2$-phenyl | |
| 228 | $CH_3$ | $MeOC_2H_4(MeOCH_2)$CH | NH | 2-Cl-4,6-$Me_2$-phenyl | |
| 229 | $CH_3$ | $MeOC_2H_4(MeOCH_2)$CH | NH | 2,4-$Me_2$-6-$MeOCH_2$-phenyl | |
| 230 | $CH_3$ | $(MeOCH_2)_2$CH | NH | 2,4-$Me_2$-6-MeO-phenyl | |

TABLE 2-continued

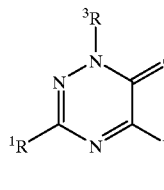

| Ex. No. | R¹ | R³ | Y | Ar | mp |
|---|---|---|---|---|---|
| 231 | $CH_3$ | $(MeOCH_2)_2CH$ | NH | 4-Br-2,6-$Me_2$-phenyl | |
| 232 | $CH_3$ | $(MeOCH_2)_2CH$ | NH | 2-Cl-4,6-$Me_2$-phenyl | |
| 233 | $CH_3$ | $(MeOCH_2)_2CH$ | NH | 2,4-$Me_2$-6-$MeOCH_2$-phenyl | |
| 234 | $CH_3$ | $MeOCH_2(Me)CH$ | NH | 2,4-$Me_2$-6-MeO-phenyl | |
| 235 | $CH_3$ | $MeOCH_2(Me)CH$ | NH | 2-Br-4,6-$Me_2$-phenyl | |
| 236 | $CH_3$ | $EtOCH_2(Et)CH$ | NH | 2-Br-4,6-$Me_2$-phenyl | |
| 237 | $CH_3$ | $EtOCH_2(Me)CH$ | NH | 2-Br-4,6-$Me_2$-phenyl | |
| 238 | $CH_3$ | $MeOCH_2(Et)CH$ | NH | 2-Br-4,6-$F_2$-phenyl | |
| 239 | $Et_2CH$ | $CH_3$ | NH | 2,4,6-$Me_3$-phenyl | |
| 240 | $Et_2CH$ | $CH_3$ | NH | 4-Br-2,6-$Me_2$-phenyl | |
| 241 | $Et_2CH$ | $CH_3$ | NH | 2-Br-4-iPr-phenyl | |
| 242 | $MeOCH_2(Et)CH$ | $CH_3$ | NH | 2,4,6-$Me_3$-phenyl | |
| 243 | $MeOCH_2(Et)CH$ | $CH_3$ | NH | 4-Br-2,6-$Me_2$-phenyl | |
| 244 | $MeOCH_2(Et)CH$ | $CH_3$ | NH | 2-Cl-4,6-$Me_2$-phenyl | |
| 245 | $(MeOCH_2)_2CH$ | $CH_3$ | NH | 2,4,6-$Me_3$-phenyl | |
| 246 | $(MeOCH_2)_2CH$ | $CH_3$ | NH | 4-Br-2,6-$Me_2$-phenyl | |
| 247 | $(MeOCH_2)_2CH$ | $CH_3$ | NH | 2-Cl-4,6-$Me_2$-phenyl | |
| 248 | $Et_2CH$ | $CH_3$ | NH | 2-Br-4,6-$(MeO)_2$-phenyl | |
| 249 | $Et_2CH$ | $CH_3$ | NH | 2-Cl-4,6-$Me_2$-phenyl | |
| 250 | $CH_3$ | $Et_2CH$ | NH | 2-Cl-4,6-$Me_2$-phenyl | |
| 251 | $CH_3$ | $Et_2CH$ | NH | 2,4-$Cl_2$-6-Me-phenyl | |
| 252 | $CH_3$ | $Et_2CH$ | NH | 2,4,6-$Cl_3$-phenyl | |
| 253 | $CH_3$ | $Et_2CH$ | NH | 2-Me-4-MeO-phenyl | |
| 254 | $CH_3$ | $Et_2CH$ | NH | 2-Cl-4-MeO-phenyl | |
| 255 | $CH_3$ | $Et_2CH$ | NH | 2,4,6-$Me_3$-5-F-phenyl | |
| 256 | $CH_3$ | $Et_2CH$ | NH | 2,5-$Me_2$-4-MeO-phenyl | |
| 257 | $CH_3$ | $Et_2CH$ | NH | 2,4-$Me_2$-6-MeO-phenyl | |
| 258 | $CH_3$ | $Et_2CH$ | NH | 2,6-$Cl_2$-4-Me-phenyl | |
| 259 | $CH_3$ | $Et_2CH$ | NH | 2,4-$Cl_2$-phenyl | |
| 260 | $CH_3$ | $Et_2CH$ | NH | 2-Cl-4-Me-phenyl | |
| 261 | $CH_3$ | $Et_2CH$ | NH | 2-Me-4-Cl-phenyl | |
| 262 | $CH_3$ | $Et_2CH$ | NH | 2-$NMe_2$-6-Me-pyrid-5-yl | |
| 263 | $CH_3$ | $Et_2CH$ | NH | 2-$NMe_2$-4-Me-pyrid-5-yl | |
| 264 | $CH_3$ | $Et_2CH$ | NH | 2-Cl-4-MeO-6-Me-phenyl | |
| 265 | $CH_3$ | $Et_2CH$ | NH | 2-Cl-4,6-$Me_2$-5-F-phenyl | |
| 266 | $CH_3$ | $Et_2CH$ | NH | 6-Cl-2,3-dihydro-benzofuran-5-yl | |
| 267 | $CH_3$ | $Et_2CH$ | NH | 6-Me-2,3-dihydro-benzofuran-5-yl | |
| 268 | $CH_3$ | $MeOCH_2(Et)CH$ | NH | 2-Cl-4,6-$Me_2$-phenyl | |
| 269 | $CH_3$ | $MeOCH_2(Et)CH$ | NH | 2,4-$Cl_2$-6-Me-phenyl | |
| 270 | $CH_3$ | $MeOCH_2(Et)CH$ | NH | 2,4,6-$Cl_3$-phenyl | |
| 271 | $CH_3$ | $MeOCH_2(Et)CH$ | NH | 2-Me-4-MeO-phenyl | |
| 272 | $CH_3$ | $MeOCH_2(Et)CH$ | NH | 2-Cl-4-MeO-phenyl | |
| 273 | $CH_3$ | $MeOCH_2(Et)CH$ | NH | 2,4,6-$Me_3$-5-F-phenyl | |
| 274 | $CH_3$ | $MeOCH_2(Et)CH$ | NH | 2,5-$Me_2$-4-MeO-phenyl | |
| 275 | $CH_3$ | $MeOCH_2(Et)CH$ | NH | 2,6-$Cl_2$-4-Me-phenyl | |
| 276 | $CH_3$ | $MeOCH_2(Et)CH$ | NH | 2,4-$Cl_2$-phenyl | |
| 277 | $CH_3$ | $MeOCH_2(Et)CH$ | NH | 2-Cl-4-Me-phenyl | |
| 278 | $CH_3$ | $MeOCH_2(Et)CH$ | NH | 2-Me-4-Cl-phenyl | |

TABLE 2-continued

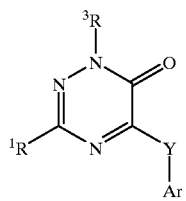

| Ex. No. | R¹ | R³ | Y | Ar | mp |
|---|---|---|---|---|---|
| 279 | CH₃ | MeOCH₂(Et)CH | NH | 2-NMe₂-6-Me-pyrid-5-yl | |
| 280 | CH₃ | MeOCH₂(Et)CH | NH | 2-NMe₂-4-Me-pyrid-5-yl | |
| 281 | CH₃ | MeOCH₂(Et)CH | NH | 2-Cl-4-MeO-6-Me-phenyl | |
| 282 | CH₃ | MeOCH₂(Et)CH | NH | 2-Cl-4,6-Me₂-5-F-phenyl | |
| 283 | CH₃ | MeOCH₂(Et)CH | NH | 6-Cl-2,3-dihydro-benzofuran-5-yl | |
| 284 | CH₃ | MeOCH₂(Et)CH | NH | 6-Me-2,3-dihydro-benzofuran-5-yl | |

Compounds wherein Y=Oxygen that can be synthesized using synthetic Scheme 3 are listed in Table 3

TABLE 3

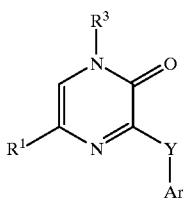

| Ex No | R¹ | R³ | Y | Ar | mp/° C. |
|---|---|---|---|---|---|
| 700 | Cl | Et₂CH | O | 2-Br-4-iPr-phenyl | |
| 701 | Cl | Et₂CH | O | 2,4-Br₂-phenyl | |
| 702 | Cl | Et₂CH | O | 2,4,6-Me₃-phenyl | |
| 703 | Cl | MeOCH₂(Et)CH | O | 2,4,6-Me₃-phenyl | 116 |
| 704 | Cl | Et₂CH | O | 2-Br-4,6-(MeO)₂-phenyl | |
| 705 | Cl | Et₂CH | O | 2-CN-4,6-Me₂-phenyl | |
| 706 | Cl | MeOCH₂(Et)CH | O | 2-Br-4,6-(MeO)₂-phenyl | |
| 707 | Cl | MeOCH₂(Et)CH | O | 2-Cl-4,6-(MeO)₂-phenyl | |
| 708 | Cl | MeOCH₂(Et)CH | O | 2-I-4,6-Me₂-phenyl | |
| 709 | Cl | MeOCH₂(Et)CH | O | 2-CN-4,6-Me₂-phenyl | |
| 710 | Cl | MeOCH₂(Et)CH | O | 2-Br-4,6-Me₂-phenyl | |
| 711 | Cl | MeOCH₂(Et)CH | O | 4-Br-2,6-Me₂-phenyl | |
| 712 | Cl | MeOCH₂(Et)CH | O | 4-MeCO-2,6-Me₂-phenyl | |
| 713 | Cl | MeOCH₂(Et)CH | O | 4-MeCO-2-OMe-6-Me-phenyl | |
| 714 | Cl | MeOCH₂(Et)CH | O | 2-MeCO-4,6-Me₂-phenyl | |
| 715 | Cl | MeOCH₂(Et)CH | O | 4,6-Me₂-2-SMe-phenyl | |
| 716 | Cl | MeOCH₂(Et)CH | O | 4,6-Me₂-2-SO₂Me-phenyl | |
| 717 | Cl | MeOCH₂(Et)CH | O | 4-Cl-2-I-6-Me-phenyl | |
| 718 | Cl | (MeOCH₂)₂CH | O | 2,4,6-Me₃-phenyl | |
| 719 | Cl | phenyl | O | 2,4,6-Me₃-phenyl | |
| 720 | CH₃ | MeOCH₂(Et)CH | O | 2,4-Br₂-phenyl | |
| 721 | CH₃ | MeOCH₂(Et)CH | O | 2-Br-4-iPr-phenyl | |
| 722 | CH₃ | MeOCH₂(Et)CH | O | 2,4,6-Me₃-phenyl | |
| 723 | CH₃ | MeOCH₂(Et)CH | O | 2-Cl-4,6-Me₂-phenyl | |
| 724 | CH₃ | (MeOCH₂)₂CH | O | 2,4,6-Me₃-phenyl | |
| 725 | CH₃ | (MeOCH₂)₂CH | O | 2,4-Cl₂-6-Me-phenyl | |
| 726 | Cl | (MeOCH₂)₂CH | O | 2,4-Cl₂-6-Me-phenyl | |
| 727 | Cl | (MeOCH₂)₂CH | O | 2,4-Br₂-6-Me-phenyl | |
| 728 | CH₃ | MeOC₂H₄(MeOCH₂)CH | O | 2,4,6-Me₃-phenyl | |
| 729 | Cl | MeOC₂H₄(MeOCH₂)CH | O | 2,4,6-Me₃-phenyl | |
| 730 | Cl | MeOC₂H₄(MeOCH₂)CH | O | 4-Br-2-OMe-6-Me-phenyl | |
| 731 | Cl | (MeOC₂H₄)₂CH | O | 2,4,6-Me₃-phenyl | |
| 732 | Cl | MeOCH₂(Et)CH | O | 2,4-Me₂-6-MeO-phenyl | |
| 733 | Cl | MeOC₂H₄(MeOCH₂)CH | O | 2,4-Me₂-6-MeO-phenyl | |
| 734 | CH₃ | MeOC₂H₄(MeOCH₂)CH | O | 2,4-Me₂-6-MeO-phenyl | |
| 735 | CH₃ | MeOC₂H₄(MeOCH₂)CH | 0 | 4-Br-2,6-Me₂-phenyl | |

TABLE 3-continued

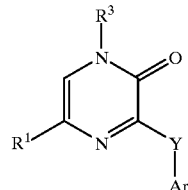

| Ex No | R¹ | R³ | Y | Ar | mp/° C. |
|---|---|---|---|---|---|
| 736 | CH₃ | MeOC₂H₄(MeOCH₂)CH | O | 2-Cl-4,6-Me₂-phenyl | |
| 737 | CH₃ | MeOC₂H₄(MeOCH₂)CH | O | 2,4-Me₂-6-MeOCH₂-phenyl | |
| 738 | CH₃ | (MeOCH₂)₂CH | O | 2,4-Me₂-6-MeO-phenyl | |
| 739 | CH₃ | (MeOCH₂)₂CH | O | 4-Br-2,6-Me₂-phenyl | |
| 740 | CH₃ | (MeOCH₂)₂CH | O | 2-Br-6-F-4-Me-phenyl | |
| 741 | CH₃ | (MeOCH₂)₂CH | O | 2-Cl-4,6-Me₂-phenyl | |
| 742 | CH₃ | (MeOCH₂)₂CH | O | 2-Cl-4-OMe-6-Me-phenyl | |
| 743 | CH₃ | (MeOCH₂)₂CH | O | 2,4-Me₂-6-MeOCH₂-phenyl | |
| 744 | Cl | MeOC₂H₄(MeOCH₂)CH | O | 2,4-Me₂-6-MeO-phenyl | |
| 745 | Cl | MeOC₂H₄(MeOCH₂)CH | O | 4-Br-2,6-Me₂-phenyl | |
| 746 | Cl | MeOC₂H₄(MeOCH₂)CH | O | 2-Cl-4,6-Me₂-phenyl | |
| 747 | Cl | MeOC₂H₄(MeOCH₂)CH | O | 2,4-Me₂-6-MeOCH₂-phenyl | |
| 748 | Cl | (MeOCH₂)₂CH | O | 2,4-Me₂-6-MeO-phenyl | |
| 749 | Cl | (MeOCH₂)₂CH | O | 4-Br-2,6-Me₂-phenyl | |
| 750 | Cl | (MeOCH₂)₂CH | O | 2-Cl-4,6-Me₂-phenyl | |
| 751 | Cl | (MeOCH₂)₂CH | O | 2,4-Me₂-6-MeOCH₂-phenyl | |
| 752 | Cl | MeOCH₂(Me)CH | O | 2,4-Me₂-6-MeO-phenyl | |
| 753 | Cl | MeOCH₂(Me)CH | O | 4-Br-2,6-Me₂-phenyl | |
| 754 | Cl | EtOCH₂(Et)CH | O | 4-Br-2,6-Me₂-phenyl | |
| 755 | Cl | EtOCH₂(Me)CH | O | 4-Br-2,6-Me₂-phenyl | |
| 756 | Cl | MeOCH₂(Et)CH | O | 4-Br-2,6-F₂-phenyl | |
| 757 | CH₃ | MeOC₂H₄(MeOCH₂)CH | O | 2-Br-4,6-Me₂-phenyl | |
| 758 | CH₃ | MeOC₂H₄(MeOCH₂)CH | O | 2,4-Me₂-6-SMe-phenyl | |
| 759 | CH₃ | MeOC₂H₄(MeOCH₂)CH | O | 2,4-Me₂-6-SO₂Me-phenyl | |
| 760 | CH₃ | MeOC₂H₄(MeOCH₂)CH | O | 4-NMe₂-2,6-Me₂-phenyl | |
| 761 | CH₃ | MeOC₂H₄(MeOCH₂)CH | O | 2,4-Cl₂-6-Me-phenyl | |
| 762 | CH₃ | MeOC₂H₄(MeOCH₂)CH | O | 4-Cl-2,6-Me₂-phenyl | |
| 763 | CH₃ | MeOC₂H₄(MeOCH₂)CH | O | 2,6-Me₂-4-SMe-phenyl | |
| 764 | CH₃ | MeOC₂H₄(MeOCH₂)CH | O | 2,6-Me₂-4-OMe-phenyl | |
| 765 | CH₃ | MeOC₂H₄(MeOCH₂)CH | O | 2,6-Me₂-4-SO₂Me-phenyl | |
| 766 | CH₃ | MeOC₂H₄(MeOCH₂)CH | O | 4-MeC(O)-2,6-Me₂-phenyl | |
| 767 | CH₃ | (MeOCH₂)₂CH | O | 4-Br-2,6-Me₂-phenyl | |
| 768 | CH₃ | (MeOCH₂)₂CH | O | 4-MeC(O)-2,6-Me₂-phenyl | |
| 769 | CH₃ | (MeOCH₂)₂CH | O | 2,6-Me₂-4-SMe-phenyl | |
| 770 | CH₃ | (MeOCH₂)₂CH | O | 2,6-Me₂-4-SO₂Me-phenyl | |
| 771 | CH₃ | (MeOCH₂)₂CH | O | 4-NMe₂-2,6-Me₂-phenyl | |
| 772 | CH₃ | (MeOCH₂)₂CH | O | 2-NMe₂-4,6-Me₂-phenyl | |
| 773 | Cl | MeOCH₂(Et)CH | O | 2,6-Me₂-4-SMe-phenyl | |
| 774 | Cl | MeOCH₂(Et)CH | O | 2,6-Me₂-4-SO₂Me-phenyl | |
| 775 | Cl | MeOCH₂(Et)CH | O | 2-Cl-4,6-Me₂-phenyl | |
| 776 | Cl | MeOCH₂(Et)CH | O | 4-Br-6-OMe-2-Me-phenyl | |
| 777 | Cl | (MeOCH₂)₂CH | O | 2,6-Me₂-4-SMe-phenyl | |
| 778 | Cl | (MeOCH₂)₂CH | O | 2,6-Me₂-4-SO₂Me-phenyl | |
| 779 | Cl | (MeOCH₂)₂CH | O | 4-Br-6-OMe-2-Me-phenyl | |
| 780 | CH₃ | Et₂CH | O | 2,4,6-Me₃-phenyl | |
| 781 | CH₃ | Et₂CH | O | 2-Cl-4,6-Me₂-phenyl | |
| 782 | CH₃ | Et₂CH | O | 2-Cl-4-OMe-6-Me-phenyl | |
| 783 | CH₃ | Et₂CH | O | 2,4,6-Me₃-pyrid-3-yl | |
| 784 | CH₃ | Et₂CH | O | 4,6-Me₂-pyrid-3-yl | |
| 785 | CH₃ | Et₂CH | O | 2-Br-6-Me-pyrid-3-yl | |
| 786 | CH₃ | Et₂CH | O | 2-Br-6-OMe-pyrid-3-yl | |
| 787 | CH₃ | Et₂CH | O | 2,6-Me₂-pyrid-3-yl | |
| 788 | CH₃ | Et₂CH | O | 2-Cl-6-Me-pyrid-3-yl | |
| 789 | CH₃ | Et₂CH | O | 2-Cl-6-OMe-pyrid-3-yl | |
| 790 | CH₃ | MeOCH₂(Et)CH | O | 2,4,6-Me₃-pyrid-3-yl | |
| 791 | CH₃ | MeOCH₂(Et)CH | O | 4,6-Me₂-pyrid-3-yl | |
| 792 | CH₃ | MeOCH₂(Et)CH | O | 2-Br-6-Me-pyrid-3-yl | |
| 793 | CH₃ | (MeOCH₂)₂CH | O | 2-Br-6-OMe-pyrid-3-yl | |
| 794 | CH₃ | (MeOCH₂)₂CH | O | 2,6-Me₂-pyrid-3-yl | |
| 795 | CH₃ | (MeOCH₂)₂CH | O | 2-Cl-6-Me-pyrid-3-yl | |
| 796 | CH₃ | (MeOCH₂)₂CH | O | 2-Cl-6-OMe-pyrid-3-yl | |
| 797 | CH₃ | MeOCH₂(Et)CH | O | 2-Br-6-OMe-pyrid-3-yl | |
| 798 | CH₃ | MeOCH₂(Et)CH | O | 2,6-Me₂-pyrid-3-yl | |
| 799 | CH₃ | MeOCH₂(Et)CH | O | 2-Cl-6-Me-pyrid-3-yl | |
| 800 | CH₃ | MeOCH₂(Et)CH | O | 2-Cl-6-OMe-pyrid-3-yl | |

TABLE 3-continued

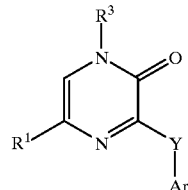

| Ex No | R$^1$ | R$^3$ | Y | Ar | mp/° C. |
|---|---|---|---|---|---|
| 801 | CH$_3$ | (MeOCH$_2$)$_2$CH | O | 2,4,6-Me$_3$-pyrid-3-yl | |
| 802 | CH$_3$ | (MeOCH$_2$)$_2$CH | O | 4,6-Me$_2$-pyrid-3-yl | |
| 803 | CH$_3$ | (MeOCH$_2$)$_2$CH | O | 2-Br-6-Me-pyrid-3-yl | |
| 804 | Cl | Et$_2$CH | O | 2-Br-6-OMe-pyrid-3-yl | |
| 805 | Cl | Et$_2$CH | O | 2,6-Me$_2$-pyrid-3-yl | |
| 806 | Cl | Et$_2$CH | O | 2-Cl-6-Me-pyrid-3-yl | |
| 807 | Cl | Et$_2$CH | O | 2-Cl-6-OMe-pyrid-3-yl | |
| 808 | Cl | MeOCH$_2$(Et)CH | O | 2,4,6-Me$_3$-pyrid-3-yl | |
| 809 | Cl | MeOCH$_2$(Et)CH | O | 4,6-Me$_2$-pyrid-3-yl | |
| 810 | Cl | MeOCH$_2$(Et)CH | O | 2-Br-6-Me-pyrid-3-yl | |
| 811 | Cl | Et$_2$CH | O | 2,4,6-Me$_3$-pyrid-3-yl | |
| 812 | Cl | Et$_2$CH | O | 4,6-Me$_2$-pyrid-3-yl | |
| 813 | Cl | Et$_2$CH | O | 2-Br-6-Me-pyrid-3-yl | |
| 814 | Cl | MeOCH$_2$(Et)CH | O | 2-Br-6-OMe-pyrid-3-yl | |
| 815 | Cl | MeOCH$_2$(Et)CH | O | 2,6-Me$_2$-pyrid-3-yl | |
| 816 | Cl | MeOCH$_2$(Et)CH | O | 2-Cl-6-Me-pyrid-3-yl | |
| 817 | Cl | MeOCH$_2$(Et)CH | O | 2-Cl-6-OMe-pyrid-3-yl | |
| 818 | Cl | (MeOCH$_2$)$_2$CH | O | 2-Br-6-OMe-pyrid-3-yl | |
| 819 | Cl | (MeOCH$_2$)$_2$CH | O | 2,6-Me$_2$-pyrid-3-yl | |
| 820 | Cl | (MeOCH$_2$)$_2$CH | O | 2-Cl-6-Me-pyrid-3-yl | |
| 821 | Cl | (MeOCH$_2$)$_2$CH | O | 2-Cl-6-OMe-pyrid-3-yl | |
| 822 | Cl | (MeOCH$_2$)$_2$CH | O | 2,4,6-Me$_3$-pyrid-3-yl | |
| 823 | Cl | (MeOCH$_2$)$_2$CH | O | 4,6-Me$_2$-pyrid-3-yl | |
| 824 | Cl | (MeOCH$_2$)$_2$CH | O | 2-Br-6-Me-pyrid-3-yl | |
| 825 | CH$_3$ | Me(Et)CH | O | 2,4,6-Me$_3$-phenyl | |
| 826 | CH$_3$ | Me(Et)CH | O | 2-Cl-4,6-Me$_2$-phenyl | |
| 827 | CH$_3$ | Me(Et)CH | O | 2,4-Cl$_2$-6-Me-phenyl | |
| 828 | CH$_3$ | Me(Et)CH | O | 2,4,6-Cl$_3$-phenyl | |
| 829 | CH$_3$ | Me(Et)CH | O | 2-Me-4-MeO-phenyl | |
| 830 | CH$_3$ | Me(Et)CH | O | 2-Cl-4-MeO-phenyl | |
| 831 | CH$_3$ | Me(Et)CH | O | 2,4,6-Me$_3$-5-F-phenyl | |
| 832 | CH$_3$ | Me(Et)CH | O | 2,5-Me$_2$-4-MeO-phenyl | |
| 833 | CH$_3$ | Me(Et)CH | O | 2,4-Me$_2$-6-MeO-phenyl | |
| 834 | CH$_3$ | Me(Et)CH | O | 2,6-Cl$_2$-4-Me-phenyl | |
| 835 | CH$_3$ | Me(Et)CH | O | 2,4-Cl$_2$-phenyl | |
| 836 | CH$_3$ | Me(Et)CH | O | 2-Cl-4-Me-phenyl | |
| 837 | CH$_3$ | Me(Et)CH | O | 2-Me-4-Cl-phenyl | |
| 838 | CH$_3$ | Me(Et)CH | O | 2-NMe$_2$-6-Me-pyrid-5-yl | |
| 839 | CH$_3$ | Me(Et)CH | O | 2-NMe$_2$-4-Me-pyrid-5-yl | |
| 840 | CH$_3$ | Me(Et)CH | O | 2-Cl-4-MeO-6-Me-phenyl | |
| 841 | CH$_3$ | Me(Et)CH | O | 2-Cl-4,6-Me$_2$-5-F-phenyl | |
| 842 | CH$_3$ | Me(Et)CH | O | 6-Cl-2,3-dihydro-benzofuran-5-yl | |
| 843 | CH$_3$ | Me(Et)CH | O | 6-Me-2,3-dihydro-benzofuran-5-yl | |
| 844 | CH$_3$ | Me(n-Pr)CH | O | 2,4,6-Me$_3$-phenyl | |
| 845 | CH$_3$ | Me(n-Pr)CH | O | 2-Cl-4,6-Me$_2$-phenyl | |
| 846 | CH$_3$ | Me(n-Pr)CH | O | 2,4-Cl$_2$-6-Me-phenyl | |
| 847 | CH$_3$ | Me(n-Pr)CH | O | 2,4,6-Cl$_3$-phenyl | |
| 848 | CH$_3$ | Me(n-Pr)CH | O | 2-Me-4-MeO-phenyl | |
| 849 | CH$_3$ | Me(n-Pr)CH | O | 2-Cl-4-MeO-phenyl | |
| 850 | CH$_3$ | Me(n-Pr)CH | O | 2,4,6-Me$_3$-5-F-phenyl | |
| 851 | CH$_3$ | Me(n-Pr)CH | O | 2,5-Me$_2$-4-MeO-phenyl | |
| 852 | CH$_3$ | Me(n-Pr)CH | O | 2,4-Me$_2$-6-MeO-phenyl | |
| 853 | CH$_3$ | Me(n-Pr)CH | O | 2,6-Cl$_2$-4-Me-phenyl | |
| 854 | CH$_3$ | Me(n-Pr)CH | O | 2,4-Cl$_2$-phenyl | |
| 855 | CH$_3$ | Me(n-Pr)CH | O | 2-Cl-4-Me-phenyl | |
| 856 | CH$_3$ | Me(n-Pr)CH | O | 2-Me-4-Cl-phenyl | |
| 857 | CH$_3$ | Me(n-Pr)CH | O | 2-NMe$_2$-6-Me-pyrid-5-yl | |
| 858 | CH$_3$ | Me(n-Pr)CH | O | 2-NMe$_2$-4-Me-pyrid-5-yl | |
| 859 | CH$_3$ | Me(n-Pr)CH | O | 2-Cl-4-MeO-6-Me-phenyl | |
| 860 | CH$_3$ | Me(n-Pr)CH | O | 2-Cl-4,6-Me$_2$-5-F-phenyl | |
| 861 | CH$_3$ | Me(n-Pr)CH | O | 6-Cl-2,3-dihydro-benzofuran-5-yl | |
| 862 | CH$_3$ | Me(n-Pr)CH | O | 6-Me-2,3-dihydro-benzofuran-5-yl | |
| 863 | CH$_3$ | c-Pr$_2$CH | O | 2,4,6-Me$_3$-phenyl | |
| 864 | CH$_3$ | c-Pr$_2$CH | O | 2-Cl-4,6-Me$_2$-phenyl | |
| 865 | CH$_3$ | c-Pr$_2$CH | O | 2,4-Cl$_2$-6-Me-phenyl | |

TABLE 3-continued

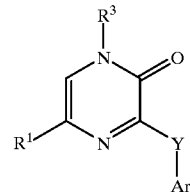

| Ex No | R¹ | R³ | Y | Ar | mp/° C. |
|---|---|---|---|---|---|
| 866 | CH₃ | c-Pr₂CH | O | 2,4,6-Cl₃-phenyl | |
| 867 | CH₃ | c-Pr₂CH | O | 2-Me-4-MeO-phenyl | |
| 868 | CH₃ | c-Pr₂CH | O | 2-Cl-4-MeO-phenyl | |
| 869 | CH₃ | c-Pr₂CH | O | 2,4,6-Me₃-5-F-phenyl | |
| 870 | CH₃ | c-Pr₂CH | O | 2,5-Me₂-4-MeO-phenyl | |
| 871 | CH₃ | c-Pr₂CH | O | 2,4-Me₂-6-MeO-phenyl | |
| 872 | CH₃ | c-Pr₂CH | O | 2,6-Cl₂-4-Me-phenyl | |
| 873 | CH₃ | c-Pr₂CH | O | 2,4-Cl₂-phenyl | |
| 874 | CH₃ | c-Pr₂CH | O | 2-Cl-4-Me-phenyl | |
| 875 | CH₃ | c-Pr₂CH | O | 2-Me-4-Cl-phenyl | |
| 876 | CH₃ | c-Pr₂CH | O | 2-NMe₂-6-Me-pyrid-5-yl | |
| 877 | CH₃ | c-Pr₂CH | O | 2-NMe₂-4-Me-pyrid-5-yl | |
| 878 | CH₃ | c-Pr₂CH | O | 2-Cl-4-MeO-6-Me-phenyl | |
| 879 | CH₃ | c-Pr₂CH | O | 2-Cl-4,6-Me₂-5-F-phenyl | |
| 880 | CH₃ | c-Pr₂CH | O | 6-Cl-2,3-dihydro-benzofuran-5-yl | |
| 881 | CH₃ | c-Pr₂CH | O | 6-Me-2,3-dihydro-benzofuran-5-yl | |
| 882 | CH₃ | c-Pr(Me)CH | O | 2,4,6-Me₃-phenyl | |
| 883 | CH₃ | c-Pr(Me)CH | O | 2-Cl-4,6-Me₂-phenyl | |
| 884 | CH₃ | c-Pr(Me)CH | O | 2,4-Cl₂-6-Me-phenyl | |
| 885 | CH₃ | c-Pr(Me)CH | O | 2,4,6-Cl₃-phenyl | |
| 886 | CH₃ | c-Pr(Me)CH | O | 2-Me-4-MeO-phenyl | |
| 887 | CH₃ | c-Pr(Me)CH | O | 2-Cl-4-MeO-phenyl | |
| 888 | CH₃ | c-Pr(Me)CH | O | 2,4,6-Me₃-5-F-phenyl | |
| 889 | CH₃ | c-Pr(Me)CH | O | 2,5-Me₂-4-MeO-phenyl | |
| 890 | CH₃ | c-Pr(Me)CH | O | 2,4-Me₂-6-MeO-phenyl | |
| 891 | CH₃ | c-Pr(Me)CH | O | 2,6-Cl₂-4-Me-phenyl | |
| 892 | CH₃ | c-Pr(Me)CH | O | 2,4-Cl₂-phenyl | |
| 893 | CH₃ | c-Pr(Me)CH | O | 2-Cl-4-Me-phenyl | |
| 894 | CH₃ | c-Pr(Me)CH | O | 2-Me-4-Cl-phenyl | |
| 895 | CH₃ | c-Pr(Me)CH | O | 2-NMe₂-6-Me-pyrid-5-yl | |
| 896 | CH₃ | c-Pr(Me)CH | O | 2-NMe₂-4-Me-pyrid-5-yl | |
| 897 | CH₃ | c-Pr(Me)CH | O | 2-Cl-4-MeO-6-Me-phenyl | |
| 898 | CH₃ | c-Pr(Me)CH | O | 2-Cl-4,6-Me₂-5-F-phenyl | |
| 899 | CH₃ | c-Pr(Me)CH | O | 6-Cl-2,3-dihydro-benzofuran-5-yl | |
| 900 | CH₃ | c-Pr(Me)CH | O | 6-Me-2,3-dihydro-benzofuran-5-yl | |
| 901 | CH₃ | c-Pr(Et)CH | O | 2,4,6-Me₃-phenyl | |
| 902 | CH₃ | c-Pr(Et)CH | O | 2-Cl-4,6-Me₂-phenyl | |
| 903 | CH₃ | c-Pr(Et)CH | O | 2,4-Cl₂-6-Me-phenyl | |
| 904 | CH₃ | c-Pr(Et)CH | O | 2,4,6-Cl₃-phenyl | |
| 905 | CH₃ | c-Pr(Et)CH | O | 2-Me-4-MeO-phenyl | |
| 906 | CH₃ | c-Pr(Et)CH | O | 2-Cl-4-MeO-phenyl | |
| 907 | CH₃ | c-Pr(Et)CH | O | 2,4,6-Me₃-5-F-phenyl | |
| 908 | CH₃ | c-Pr(Et)CH | O | 2,5-Me₂-4-MeO-phenyl | |
| 909 | CH₃ | c-Pr(Et)CH | O | 2,4-Me₂-6-MeO-phenyl | |
| 910 | CH₃ | c-Pr(Et)CH | O | 2,6-Cl₂-4-Me-phenyl | |
| 911 | CH₃ | c-Pr(Et)CH | O | 2,4-Cl₂-phenyl | |
| 912 | CH₃ | c-Pr(Et)CH | O | 2-Cl-4-Me-phenyl | |
| 913 | CH₃ | c-Pr(Et)CH | O | 2-Me-4-Cl-phenyl | |
| 914 | CH₃ | c-Pr(Et)CH | O | 2-NMe₂-6-Me-pyrid-5-yl | |
| 915 | CH₃ | c-Pr(Et)CH | O | 2-NMe₂-4-Me-pyrid-5-yl | |
| 916 | CH₃ | c-Pr(Et)CH | O | 2-Cl-4-MeO-6-Me-phenyl | |
| 917 | CH₃ | c-Pr(Et)CH | O | 2-Cl-4,6-Me₂-5-F-phenyl | |
| 918 | CH₃ | c-Pr(Et)CH | O | 6-Cl-2,3-dihydro-benzofuran-5-yl | |
| 919 | CH₃ | c-Pr(Et)CH | O | 6-Me-2,3-dihydro-benzofuran-5-yl | |
| 920 | CH₃ | c-Pr(n-Pr)CH | O | 2,4,6-Me₃-phenyl | |
| 921 | CH₃ | c-Pr(n-Pr)CH | O | 2-Cl-4,6-Me₂-phenyl | |
| 922 | CH₃ | c-Pr(n-Pr)CH | O | 2,4-Cl₂-6-Me-phenyl | |
| 923 | CH₃ | c-Pr(n-Pr)CH | O | 2,4,6-Cl₃-phenyl | |
| 924 | CH₃ | c-Pr(n-Pr)CH | O | 2-Me-4-MeO-phenyl | |
| 925 | CH₃ | c-Pr(n-Pr)CH | O | 2-Cl-4-MeO-phenyl | |
| 926 | CH₃ | c-Pr(n-Pr)CH | O | 2,4,6-Me₃-5-F-phenyl | |
| 927 | CH₃ | c-Pr(n-Pr)CH | O | 2,5-Me₂-4-MeO-phenyl | |
| 928 | CH₃ | c-Pr(n-Pr)CH | O | 2,4-Me₂-6-MeO-phenyl | |
| 929 | CH₃ | c-Pr(n-Pr)CH | O | 2,6-Cl₂-4-Me-phenyl | |
| 930 | CH₃ | c-Pr(n-Pr)CH | O | 2,4-Cl₂-phenyl | |

TABLE 3-continued

| Ex No | R¹ | R³ | Y | Ar | mp/° C. |
|---|---|---|---|---|---|
| 931 | CH₃ | c-Pr(n-Pr)CH | O | 2-Cl-4-Me-phenyl | |
| 932 | CH₃ | c-Pr(n-Pr)CH | O | 2-Me-4-Cl-phenyl | |
| 933 | CH₃ | c-Pr(n-Pr)CH | O | 2-NMe₂-6-Me-pyrid-5-yl | |
| 934 | CH₃ | c-Pr(n-Pr)CH | O | 2-NMe₂-4-Me-pyrid-5-yl | |
| 935 | CH₃ | c-Pr(n-Pr)CH | O | 2-Cl-4-MeO-6-Me-phenyl | |
| 936 | CH₃ | c-Pr(n-Pr)CH | O | 2-Cl-4,6-Me₂-5-F-phenyl | |
| 937 | CH₃ | c-Pr(n-Pr)CH | O | 6-Cl-2,3-dihydro-benzofuran-5-yl | |
| 938 | CH₃ | c-Pr(n-Pr)CH | O | 6-Me-2,3-dihydro-benzofuran-5-yl | |
| 939 | CH₃ | c-Pr(n-Bu)CH | O | 2,4,6-Me₃-phenyl | |
| 940 | CH₃ | c-Pr(n-Bu)CH | O | 2-Cl-4,6-Me₂-phenyl | |
| 941 | CH₃ | c-Pr(n-Bu)CH | O | 2,4-Cl₂-6-Me-phenyl | |
| 942 | CH₃ | c-Pr(n-Bu)CH | O | 2,4,6-Cl₃-phenyl | |
| 943 | CH₃ | c-Pr(n-Bu)CH | O | 2-Me-4-MeO-phenyl | |
| 944 | CH₃ | c-Pr(n-Bu)CH | O | 2-Cl-4-MeO-phenyl | |
| 945 | CH₃ | c-Pr(n-Bu)CH | O | 2,4,6-Me₃-5-F-phenyl | |
| 946 | CH₃ | c-Pr(n-Bu)CH | O | 2,5-Me₂-4-MeO-phenyl | |
| 947 | CH₃ | c-Pr(n-Bu)CH | O | 2,4-Me₂-6-MeO-phenyl | |
| 948 | CH₃ | c-Pr(n-Bu)CH | O | 2,6-Cl₂-4-Me-phenyl | |
| 949 | CH₃ | c-Pr(n-Bu)CH | O | 2,4-Cl₂-phenyl | |
| 950 | CH₃ | c-Pr(n-Bu)CH | O | 2-Cl-4-Me-phenyl | |
| 951 | CH₃ | c-Pr(n-Bu)CH | O | 2-Me-4-Cl-phenyl | |
| 952 | CH₃ | c-Pr(n-Bu)CH | O | 2-NMe₂-6-Me-pyrid-5-yl | |
| 953 | CH₃ | c-Pr(n-Bu)CH | O | 2-NMe₂-4-Me-pyrid-5-yl | |
| 954 | CH₃ | c-Pr(n-Bu)CH | O | 2-Cl-4-MeO-6-Me-phenyl | |
| 955 | CH₃ | c-Pr(n-Bu)CH | O | 2-Cl-4,6-Me₂-5-F-phenyl | |
| 956 | CH₃ | c-Pr(n-Bu)CH | O | 6-Cl-2,3-dihydro-benzofuran-5-yl | |
| 957 | CH₃ | c-Pr(n-Bu)CH | O | 6-Me-2,3-dihydro-benzofuran-5-yl | |
| 958 | CH₃ | c-PrCH₂(Et)CH | O | 2,4,6-Me₃-phenyl | |
| 959 | CH₃ | c-PrCH₂(Et)CH | O | 2-Cl-4,6-Me₂-phenyl | |
| 960 | CH₃ | c-PrCH₂(Et)CH | O | 2,4-Cl₂-6-Me-phenyl | |
| 961 | CH₃ | c-PrCH₂(Et)CH | O | 2,4,6-Cl₃-phenyl | |
| 962 | CH₃ | c-PrCH₂(Et)CH | O | 2-Me-4-MeO-phenyl | |
| 963 | CH₃ | c-PrCH₂(Et)CH | O | 2-Cl-4-MeO-phenyl | |
| 964 | CH₃ | c-PrCH₂(Et)CH | O | 2,4,6-Me₃-5-F-phenyl | |
| 965 | CH₃ | c-PrCH₂(Et)CH | O | 2,5-Me₂-4-MeO-phenyl | |
| 966 | CH₃ | c-PrCH₂(Et)CH | O | 2,4-Me₂-6-MeO-phenyl | |
| 967 | CH₃ | c-PrCH₂(Et)CH | O | 2,6-Cl₂-4-Me-phenyl | |
| 968 | CH₃ | c-PrCH₂(Et)CH | O | 2,4-Cl₂-phenyl | |
| 969 | CH₃ | c-PrCH₂(Et)CH | O | 2-Cl-4-Me-phenyl | |
| 970 | CH₃ | c-PrCH₂(Et)CH | O | 2-Me-4-Cl-phenyl | |
| 971 | CH₃ | c-PrCH₂(Et)CH | O | 2-NMe₂-6-Me-pyrid-5-yl | |
| 972 | CH₃ | c-PrCH₂(Et)CH | O | 2-NMe₂-4-Me-pyrid-5-yl | |
| 973 | CH₃ | c-PrCH₂(Et)CH | O | 2-Cl-4-MeO-6-Me-phenyl | |
| 974 | CH₃ | c-PrCH₂(Et)CH | O | 2-Cl-4,6-Me₂-5-F-phenyl | |
| 975 | CH₃ | c-PrCH₂(Et)CH | O | 6-Cl-2,3-dihydro-benzofuran-5-yl | |
| 976 | CH₃ | c-PrCH₂(Et)CH | O | 6-Me-2,3-dihydro-benzofuran-5-yl | |
| 977 | CH₃ | Et₂CH | O | 2,4-Cl₂-6-Me-phenyl | |
| 978 | CH₃ | Et₂CH | O | 2,4,6-Cl₃-phenyl | |
| 979 | CH₃ | Et₂CH | O | 2-Me-4-MeO-phenyl | |
| 980 | CH₃ | Et₂CH | O | 2-Cl-4-MeO-phenyl | |
| 981 | CH₃ | Et₂CH | O | 2,4,6-Me₃-5-F-phenyl | |
| 982 | CH₃ | Et₂CH | O | 2,5-Me₂-4-MeO-phenyl | |
| 983 | CH₃ | Et₂CH | O | 2,4-Me₂-6-MeO-phenyl | |
| 984 | CH₃ | Et₂CH | O | 2,6-Cl₂-4-Me-phenyl | |
| 985 | CH₃ | Et₂CH | O | 2,4-Cl₂-phenyl | |
| 986 | CH₃ | Et₂CH | O | 2-Cl-4-Me-phenyl | |
| 987 | CH₃ | Et₂CH | O | 2-Me-4-Cl-phenyl | |
| 988 | CH₃ | Et₂CH | O | 2-NMe₂-6-Me-pyrid-5-yl | |
| 989 | CH₃ | Et₂CH | O | 2-NMe₂-4-Me-pyrid-5-yl | |
| 990 | CH₃ | Et₂CH | O | 2-Cl-4,6-Me₂-5-F-phenyl | |
| 991 | CH₃ | Et₂CH | O | 6-Cl-2,3-dihydro-benzofuran-5-yl | |
| 992 | CH₃ | Et₂CH | O | 6-Me-2,3-dihydro-benzofuran-5-yl | |

Additional compounds, wherein Y=oxygen that can be synthesized using synthetic Scheme 6 or Scheme 7 are listed Table 4

TABLE 4

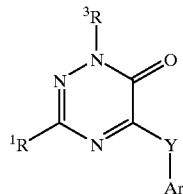

| Ex. No. | R¹ | R³ | Y | Ar | mp |
|---|---|---|---|---|---|
| 1000 | CH₃ | Et₂CH | O | 2,4,6-Me₃-phenyl | |
| 1001 | CH₃ | Et₂CH | O | 2-Cl-4,6-Me₂-phenyl | |
| 1002 | CH₃ | Et₂CH | O | 2,4-Cl₂-6-Me-phenyl | |
| 1003 | CH₃ | Et₂CH | O | 2,4,6-Cl₃-phenyl | |
| 1004 | CH₃ | Et₂CH | O | 2-Me-4-MeO-phenyl | |
| 1005 | CH₃ | Et₂CH | O | 2-Cl-4-MeO-phenyl | |
| 1006 | CH₃ | Et₂CH | O | 2,4,6-Me₃-5-F-phenyl | |
| 1007 | CH₃ | Et₂CH | O | 2,5-Me₂-4-MeO-phenyl | |
| 1008 | CH₃ | Et₂CH | O | 2,4-Me₂-6-MeO-phenyl | |
| 1009 | CH₃ | Et₂CH | O | 2,6-Cl₂-4-Me-phenyl | |
| 1010 | CH₃ | Et₂CH | O | 2,4-Cl₂-phenyl | |
| 1011 | CH₃ | Et₂CH | O | 2-Cl-4-Me-phenyl | |
| 1012 | CH₃ | Et₂CH | O | 2-Me-4-Cl-phenyl | |
| 1013 | CH₃ | Et₂CH | O | 2-NMe₂-6-Me-pyrid-5-yl | |
| 1014 | CH₃ | Et₂CH | O | 2-NMe₂-4-Me-pyrid-5-yl | |
| 1015 | CH₃ | Et₂CH | O | 2-Cl-4-MeO-6-Me-phenyl | |
| 1016 | CH₃ | Et₂CH | O | 2-Cl-4,6-Me₂-5-F-phenyl | |
| 1017 | CH₃ | Et₂CH | O | 6-Cl-2,3-dihydro-benzofuran-5-yl | |
| 1018 | CH₃ | Et₂CH | O | 6-Me-2,3-dihydro-benzofuran-5-yl | |

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of PGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 mM hygromycin. Cells surviving 4 weeks of selection in hygromycin were pooled, adapted to growth in suspension and used to generate membranes for the binding assay described below. Individual aliquots containing approximately 1×10⁸ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 mg/l aprotinin, 1 mg/ml leupeptin and 1 mg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 mg/ml to be used in the assay.

Binding assays are performed in 96 well plates; each well having a 300 ml capacity. To each well is added 50 ml of test drug dilutions (final concentration of drugs range from $10^{-10}$–$10^{-5}$ M), 100 ml of $^{125}$I-ovine-CRF ($^{125}$I-o-CRF) (final concentration 150 pM) and 150 ml of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980)], which provides Ki values for inhibition which are then used to assess biological activity.

A compound is considered to be active if it has a $K_i$ value of less than about 10000 nM for the inhibition of CRF. Compounds with a $K_i$ less than 100 nM for the inhibition of CRF are desirable. A number of compounds of the invention have been made and tested in the above assay and shown to have $K_i$ values less than 100 nM thus confirming the utility of the invention.

Inhibition of CRF-Stimulated Adenylate Cyclase Activity

Inhibition of CRF—Stimulated adenylate cyclase activity was performed as described by G. Battaglia et al. Synapse 1:572 (1987). Briefly, assays were carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6}$ m) and 0.8 mg original wet weight tissue (approximately 40–60 mg protein). Reactions were initiated by the addition of 1 mM ATP/[$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

A compound of this invention was tested in this assay and found to be active; $IC_{50}$<10000 nM.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990)

Compounds may be tested in any species of rodent or small mammal. Disclosure of the assays herein is not intended to limit the enablement of the invention.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

We claim:

1. A compound of Formula I:

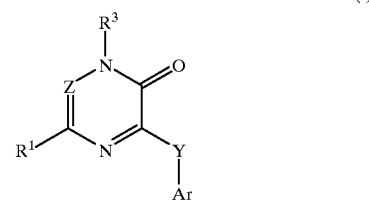

or a pharmaceutically acceptable salt form thereof, wherein:

Z is $CR^2$;

Y is $NR^4$, O, $S(O)_n$;

Ar is phenyl, naphthyl, pyridyl, pyrimidinyl, pyridazinyl, pyrazinyl, 1,3,5-triazinyl, 1,2,4-triazinyl, furanyl, quinolinyl, isoquinolinyl, thienyl, imidazolyl, thiazolyl, indolyl, indolinyl, pyrrolyl, oxazolyl, benzofuranyl, benzothienyl, 2,3-dihydrobenzofuranyl, 2,3-dihydrobenzothienyl, benzothiazolyl, indazolyl, isoxazolyl or pyrazolyl, each substituted with 0 to 4 $R^5$ groups; wherein Ar is attached to Y through an unsaturated carbon;

$R^1$ is H, halo, $C_1-C_{10}$ alkyl, $C_2-C_{10}$ alkenyl, $C_2-C_{10}$ alkynyl, $C_3-C_8$ cycloalkyl, $C_1-C_4$ haloalkyl, aryl, heterocyclyl, —CN, —$OR^7$, —SH, —$S(O)_nR^{13}$, —$COR^7$, —$CONR^6R^7$, —$CO_2R^7$, —$OC(O)R^{13}$, —$NR^8COR^7$, —$N(COR^7)_2$, —$NR^8CONR^6R^7$, —$NR^8CO_2R^7$, or —$NR^6R^7$, wherein $C_1-C_{10}$ alkyl, $C_2-C_{10}$ alkenyl, $C_2-C_{10}$ alkynyl or $C_3-C_8$ cycloalkyl is each substituted with 0 to 3 substituents independently selected at each occurrence from $C_1-C_6$ alkyl, $C_3-C_6$ cycloalkyl, halo, $C_1-C_4$ haloalkyl, —CN, —$OR^7$, —SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^7$, —$NR^6R^7$, —$CONR^6R^7$, aryl and heterocyclyl;

$R^2$ is H, $C_1-C_4$ alkyl, $C_2-C_4$ alkenyl, $C_2-C_4$ alkynyl, $C_3-C_6$ cycloalkyl, halo, —CN, $C_1-C_4$ haloalkyl, —$NR^9R^{10}$, —$NR^9COR^{10}$, —$NR^9CO_2R^{10}$, —$OR^{11}$, —SH or —$S(O)_nR^{12}$;

$R^3$ is $C_1-C_{10}$ alkyl, $C_2-C_{10}$ alkenyl, $C_2-C_{10}$ alkynyl, $C_3-C_8$ cycloalkyl, $C_1-C_4$ haloalkyl, aryl, heterocyclyl, —CN, —OR$^7$, —S(O)$_2$R$^{13}$, —COR$^7$, —CO$_2$R$^7$, —NR$^8$COR$^7$, —N(COR$^7$)$_2$, —NR$^8$CONR$^6$R$^7$, —CONR$^6$R$^7$, —NR$^8$CO$_2$R$^7$, or —NR$^6$R$^7$, wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^7$, —S(O)$_n$R$^{13}$, —COR$^7$, —CO$_2$R$^7$, —NR$^8$COR$^7$, —N(COR$^7$)$_2$, —NR$^8$CONR$^6$R$^7$, —NR$^8$CO$_2$R$^7$, —NR$^6$R$^7$, —CONR$^6$R$^7$, aryl and heterocyclyl, with the proviso that when R$^3$ is aryl, Ar is not imidazolyl;

R$^4$ is H, C$_1$–C$_6$ alkyl, C$_2$–C$_6$ alkenyl or C$_2$–C$_6$ alkynyl, wherein C$_2$–C$_6$ alkenyl or C$_2$–C$_6$ alkynyl is optionally substituted with C$_1$–C$_4$ alkyl or C$_3$–C$_6$ cycloalkyl and wherein C$_1$–C$_6$ alkyl is optionally substituted with C$_1$–C$_4$ alkyl, C$_3$–C$_6$ cycloalkyl, C$_1$–C$_4$ haloalkyl, —OR$^7$, —S(O)$_n$R$^{12}$, —CO$_2$R$^7$, —NR$^6$R$^7$ or —NR$^9$COR$^{10}$;

R$^5$ is independently selected at each occurrence from C$_1$–C$_{10}$ alkyl, C$_2$–C$_{10}$ alkenyl, C$_2$–C$_{10}$ alkynyl, C$_3$–C$_6$ cycloalkyl, C$_4$–C$_{12}$ cycloalkylalkyl, aryl, heterocyclyl, —NO$_2$, halo, —CN, C$_1$–C$_4$ haloalkyl, —NR$^6$R$^7$, —NR$^8$COR$^7$, —NR$^8$CO$_2$R$^7$, —OR$^7$, —COR$^7$, —CO$_2$R$^7$, —CONR$^6$R$^7$, —CON(OR$^9$)R$^7$, —SH, and —S(O)$_n$R$^{13}$,
wherein C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are substituted with 0 to 3 substituents independently selected at each occurrence from C$_1$–C$_4$ alkyl, —NO$_2$, halo, —CN, —OR$^7$, —COR$^7$, —CO$_2$R$^7$, —CONR$^6$R$^7$, —NR$^6$R$^7$, —NR$^8$COR$^7$, —NR$^8$CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heterocyclyl, heterocyclyl(C$_1$–C$_4$ alkyl)-, morpholinoethyl, morpholinopropyl and morpholinobutyl; or NR$^6$R$^7$ taken together as a whole is piperidine, pyrrolidine, piperazine, N-methylpiperazine, morpholine or thiomorpholine;
wherein C$_1$–C$_4$ alkyl, may be substituted with 0 to 2 substituents independently selected at each occurrence from —OH or C$_1$–C$_4$ alkoxy groups;

R$^8$ is independently at each occurrence H or C$_1$–C$_4$ alkyl;

R$^9$ and R$^{10}$ are independently at each occurrence selected from H, C$_1$–C$_4$ alkyl and C$_3$–C$_6$ cycloalkyl;

R$^{11}$ is H, C$_1$–C$_4$ alkyl, C$_1$–C$_4$ haloalkyl, or C$_3$–C$_6$ cycloalkyl;

R$^{12}$ is C$_1$–C$_4$ alkyl, C$_1$–C$_4$ haloalkyl or —NR$^6$R$^7$;

R$^{13}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^6$R$^7$, aryl, aryl(C$_1$–C$_4$ alkyl)-, heterocyclyl or heterocyclyl(C$_1$–C$_4$ alkyl)-;

R$^{14}$ is C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, —NR$^{15}$R$^{16}$;

R$^{15}$ and R$^{16}$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl and C$_4$–C$_{12}$ cycloalkylalkyl; or —NR$^{15}$R$^{16}$ taken together as a whole is piperidine, pyrrolidine, piperazine, N-methylpiperazine, morpholine or thiomorpholine;

aryl is phenyl, biphenyl or naphthyl, each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^{15}$, —SH, —S(O)$_n$R$^{14}$, —COR$^{15}$, —CO$_2$R$^{15}$, —OC(O)R$^{14}$, —NO$_2$, —NR$^8$COR$^{15}$, —N(COR$^{15}$)$_2$, —NR$^8$CONR$^{15}$R$^{16}$, —NR$^8$CO$_2$R$^{15}$, —NR$^{15}$R$^{16}$ and —CONR$^{15}$R$^{16}$;

heterocyclyl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each substituted with 0 to 3 substituents independently selected at each occurrence from C$_1$–C$_6$ alkyl, C$_3$–C$_6$ cycloalkyl, halo, C$_1$–C$_4$ haloalkyl, —CN, —OR$^{15}$, —SH, —S(O)$_n$R$^{14}$, —COR$^{15}$, —CO$_2$R$^{15}$, —OC(O)R$^{14}$, —NO$_2$, —NR$^8$COR$^{15}$, —N(COR$^{15}$)$_2$, —NR$^8$CONR$^{15}$R$^{16}$, —NR$^8$CO$_2$R$^{15}$, —NR$^{15}$R$^{16}$ and —CONR$^{15}$R$^{16}$; and n is independently at each occurrence 0, 1 or 2.

2. A compound of claim 1 wherein:

Z is CR$^2$;

Y is NR$^4$ or O;

Ar is phenyl or pyridyl, each substituted with 0 to 4 R$^5$ groups;

R$^1$ is H, halo, C$_1$–C$_4$ alkyl, cyclopropyl, C$_1$–C$_4$ haloalkyl, —CN, —NR$^6$R$^7$, —CONR$^6$R$^7$, —OR$^7$, —COR$^7$, —CO$_2$R$^7$ or —S(O)$_n$R$^{13}$,
wherein C$_1$–C$_4$ alkyl is substituted with 0 to 3 substituents independently selected at each occurrence from C$_1$–C$_4$ alkyl, C$_3$–C$_6$ cycloalkyl, halo, —CN, —OR$^7$, —S(O)$_n$R$^{13}$, —COR$^7$, —CO$_2$R$^7$, —NR$^8$COR$^7$, —NR$^8$CO$_2$R$^7$, —NR$^6$R$^7$ and aryl;

R$^2$ is H, C$_1$–C$_4$ alkyl, halo, C$_1$–C$_4$ haloalkyl;

R$^3$ is C$_1$–C$_{10}$ alkyl, C$_2$–C$_{10}$ alkenyl, C$_2$–C$_{10}$ alkynyl, C$_3$–C$_8$ cycloalkyl, C$_1$–C$_4$ haloalkyl, aryl, heterocyclyl, —CN, —OR$^7$, —S(O)$_2$R$^{13}$, —COR$^7$, —CO$_2$R$^7$, —NR$^8$COR$^7$, —N(COR$^7$)$_2$, —NR$^8$CONR$^6$R$^7$, —CONR$^6$R$^7$, —NR$^8$CO$_2$R$^7$, or —NR$^6$R$^7$,
wherein C$_1$–C$_{10}$ alkyl, C$_2$–C$_{10}$ alkenyl, C$_2$–C$_{10}$ alkynyl or C$_3$–C$_8$ cycloalkyl is each substituted with 0 to 3 substituents independently selected at each occurrence from C$_1$–C$_6$ alkyl, C$_3$–C$_6$ cycloalkyl, C$_1$–C$_4$ haloalkyl, halo, —CN, —OR$^7$, —S(O)$_n$R$^{13}$, —CO$_2$R$^7$, —NR$^8$COR$^7$, —NR$^8$CONR$^6$R$^7$, —NR$^8$CO$_2$R$^7$, —NR$^6$R$^7$, aryl and heterocyclyl;

R$^4$ is H, C$_1$–C$_6$ alkyl or C$_2$–C$_6$ alkenyl, wherein C$_1$–C$_6$ alkyl is optionally substituted with C$_1$–C$_4$ alkyl, C$_1$–C$_4$ haloalkyl, —OR$^7$, —S(O)$_n$R$^{12}$, —CO$_2$R$^7$, —NR$^6$R$^7$ or —NR$^9$COR$^{10}$;

R$^5$ is independently selected at each occurrence from C$_1$–C$_6$ alkyl, C$_2$–C$_6$ alkenyl, C$_2$–C$_6$ alkynyl, C$_3$–C$_6$ cycloalkyl, C$_4$–C$_8$ cycloalkylalkyl, aryl, heterocyclyl, C$_1$–C$_4$ haloalkyl, halo, —CN, —NO$_2$, —NR$^6$R$^7$, —COR$^7$, —OR$^7$, —CONR$^6$R$^7$, —CON (OR$^9$) R$^7$, CO$_2$R$^7$ and —S(O)$_n$R$^{13}$,
wherein C$_1$–C$_6$ alkyl, C$_2$–C$_6$ alkenyl, C$_2$–C$_6$ alkynyl, C$_3$–C$_6$ cycloalkyl and C$_4$–C$_8$ cycloalkylalkyl are substituted with 0 to 3 substituents independently selected at each occurrence from C$_1$–C$_4$ alkyl, —NO$_2$, halo, —CN, —NR$^6$R$^7$, COR$^7$, —OR$^7$, —CONR$^6$R$^7$, CO$_2$R$^7$ and —S(O)$_n$R$^{13}$;

R$^6$ and R$^7$ are independently selected at each occurrence from H, C$_1$–C$_4$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, aryl, aryl(C$_1$–C$_4$ alkyl)-, heterocyclyl, heterocyclyl(C$_1$–C$_4$ alkyl)-, morpholinoethyl, morpholinopropyl and morpholinobutyl; or —NR$^6$R$^7$ taken together as a whole is piperidine, pyrrolidine, piperazine, N-methylpiperazine, morpholine or thiomorpholine;

wherein $C_1$–$C_4$ alkyl, may be substituted with 0 to 2 substituents independently selected at each occurrence from —OH or $C_1$–$C_4$ alkoxy groups;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl, $C_1$–$C_4$ haloalkyl or —$NR^6R^7$;

$R^{13}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^6R^7$, aryl, aryl($C_1$–$C_4$ alkyl)-, heterocyclyl or heterocyclyl ($C_1$–$C_4$ alkyl)-;

$R^{14}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^{15}R^{16}$;

$R^{15}$ and $R^{16}$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl and $C_4$–$C_{12}$ cycloalkylalkyl; or —$NR^{15}R^{16}$ taken together as a whole is piperidine, pyrrolidine, piperazine, N-methylpiperazine, morpholine or thiomorpholine;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$, —$NR^8COR^{15}$, —$NR^8CONR^{15}R^{16}$, —$NR^8CO_2R^{15}$ and —$NR^{15}R^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from $C_1$–$C_4$ alkyl, halo, —CN, —$OR^{15}$, —$S(O)_nR^{14}$, —$CO_2R^{15}$, —$NO_2$, —$NR^8COR^{15}$, —$NR^8CONR^{15}R^{16}$, —$NR^8CO_2R^{15}$, and —$NR^{15}R^{16}$; and n is independently at each occurrence 0, 1 or 2.

3. A compound of claim 2 wherein:

Z is $CR^2$;

Y is $NR^4$;

Ar is phenyl or pyridyl, each substituted with 0 to 4 $R^5$ groups;

$R^1$ is H, halo, $C_1$–$C_4$ alkyl, cyclopropyl, $C_1$–$C_3$ haloalkyl, —CN, —$NR^6R^7$, —$CONR^6R^7$, —$COR^7$, —$CO_2R^7$, —$OR^7$ or —$S(O)_nR^{13}$ wherein $C_1$–$C_4$ alkyl is substituted with 0 to 3 substituents independently selected at each occurrence from $C_3$–$C_4$ cycloalkyl, halo, —CN, —$OR^7$, —$S(O)_nR^{13}$, —$COR^7$, —$CO_2R^7$, —$NR^6R^7$;

$R^2$ is H;

$R^3$ is $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl or aryl, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_6$ alkyl, $C_3$–$C_6$ cycloalkyl, $C_1$–$C_4$ haloalkyl, halo, —CN, —$OR^7$, —$S(O)_nR^{13}$, —$CO_2R^7$, —$NR^8COR^7$, —$NR^8CONR^6R^7$, —$NR^8CO_2R^7$, —$NR^6R^7$ and aryl;

$R^4$ is H, allyl, or $C_1$–$C_4$ alkyl, wherein $C_1$–$C_4$ alkyl is optionally substituted with $C_1$–$C_4$ alkyl, —$OR^7$, —$S(O)_2R^{12}$, —$CO_2R^7$, —$NR^6R^7$ or —$NR^9COR^{10}$;

$R^5$ is independently selected at each occurrence from $C_1$–$C_6$ alkyl, aryl, heterocyclyl, $C_1$–$C_4$ haloalkyl, halo, —CN, —$NO_2$, —$NR^6R^7$, —$COR^7$, —$OR^7$, —$CONR^6R^7$, —$CON(OR^9)R^7$, —$CO_2R^7$ and —$S(O)_nR^{13}$, wherein $C_1$–$C_6$ alkyl is substituted with 0 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$ and —$S(O)_nR^{13}$;

$R^6$ and $R^7$ are independently selected at each occurrence from H, $C_1$–$C_4$ alkyl, $C_1$–$C_4$ haloalkyl and $C_2$–$C_8$ alkoxyalkyl;

wherein $C_1$–$C_4$ alkyl, may be substituted with 0 to 2 substituents independently selected at each occurrence from —OH or $C_1$–$C_4$ alkoxy groups;

$R^8$, $R^9$ and $R^{10}$ are independently at each occurrence H or $C_1$–$C_4$ alkyl;

$R^{12}$ and $R^{13}$ are independently at each occurrence $C_1$–$C_4$ alkyl or —$NR^6R^7$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, $S(O)_nR^{14}$, —$COR^{15}$ —$CO_2R^{15}$, —$NO_2$ and —$NR^{15}R^{16}$; and n is independently at each occurrence 0, 1 or 2.

4. A compound of claim 3 wherein:

Z is $CR^2$;

Y is $NR^4$;

Ar is phenyl or pyridyl, each substituted with 2 to 4 $R^5$ groups;

$R^1$ is H, Cl, Br, methyl, ethyl, cyclopropyl, or —CN, $R^2$ is H;

$R^3$ is $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl or aryl, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_4$ alkyl, $C_3$–$C_6$ cycloalkyl, —$CF_3$, halo, —CN, —$OR^7$, and aryl;

$R^4$ is H, methyl, ethyl, i-propyl, n-propyl, n-butyl, i-butyl, s-butyl, n-butyl, or allyl;

$R^5$ is independently selected at each occurrence from methyl, ethyl, i-propyl, n-propyl, aryl, —$CF_3$, halo, —CN, —$N(CH_3)2$, —$C(=O)CH_3$, —$OCH_3$, —$OCH_2CH_3$, —$OCF_3$, and —$S(O)_2CH_3$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R_5$, —$NO_2$ and —$NR^{15}R^{16}$; and n is independently at each occurrence 0, 1 or 2.

5. A compound of claim 4 selected from:

3-[(2,4-Dibromophenyl)amino]-5-chloro-1-(1-ethylpropyl)-2(1H)-pyrazinone;

3-[[2-Bromo-4-(1-methylethyl)phenyl]amino]-5-chloro-1-(1-ethylpropyl)-2(1H)-pyrazinone;

3-[(2,4-Dibromophenyl)ethylamino]-5-chloro-1-(1-ethylpropyl)-2(1H)-pyrazinone;

3-[[2-Bromo-4-(1-methylethyl)phenyl]ethylamino]-5-chloro-1-(1-ethylpropyl)-2(1H)-pyrazinone;

3-[(2,4,6-Trimethylphenyl)amino]-5-chloro-1-(1-ethylpropyl)-2(1H)-pyrazinone;

3-[(2,4,6-Trimethylphenyl)ethylamino]-5-chloro-1-(1-ethylpropyl)-2(1H)-pyrazinone;

(+/−)-3-[(2,4,6-Trimethylphenyl)amino]-5-chloro-1-[1-(methoxymethyl)propyl]-2 (1H)-pyrazinone;

3-[(2-Bromo-4,6-dimethoxyphenyl)amino]-5-chloro-1-(1-ethylpropyl)-2(1H)-pyrazinone;

3-[(2-Cyano-4,6-dimethylphenyl)amino]-5-chloro-1-[1-(methoxymethyl)propyl]-2 (1H)-pyrazinone;

(+/−)-3-[(2-Bromo-4,6-dimethoxyphenyl)amino]-5-chloro-1-[1-(methoxymethyl)propyl]-2 (1H)-pyrazinone;

(+/−)-3-[(2-chloro-4,6-dimethoxyphenyl)amino]-5-chloro-1-[1-(methoxymethyl)propyl]-2 (1H)-pyrazinone;

(+/−)-3-[(4,6-Dimethyl-2-iodophenyl)amino]-5-chloro-1-[1-(methoxymethyl)propyl]-2 (1H)-pyrazinone;

[(2-cyano-4,6-dimethylphenyl)amino]-5-chloro-1-[1-(methoxymethyl)propyl]-2(1H)-pyrazinone;

(+/−)-3-[(2-Bromo-4,6-dimethylphenyl)amino]-5-chloro-1-[1-(methoxymethyl)propyl]-2 (1H)-pyrazinone;

(+/−)-3-[(4-Bromo-2,6-dimethylphenyl)amino]-5-chloro-1-[1-(methoxymethyl)propyl]-2(1H)-pyrazinone;

(+/−)-3-[(4-Acetyl-2,6-dimethylphenyl)amino]-5-chloro-1-[1-(methoxymethyl)propyl]-2 (1H)-pyrazinone;

(+/−)-3-[(2-Acetyl-4,6-dimethylphenyl)amino]-5-chloro-1-[1-(methoxymethyl)propyl]-2(1H)-pyrazinone;

(+/−)-3-[(4,6-Dimethyl-2-thiomethylphenyl)amino]-5-chloro-1-[1-(methoxymethyl)propyl]-2(1H)-pyrazinone;

(+/−)-3-[(4,6-Dimethyl-2-methylsulfonylphenyl)amino]-5-chloro-1-[1-(methoxymethyl)propyl]-2(1H)-pyrazinone;

(+/−)-3-[(4-chloro-2-iodo-6-methylphenyl)amino]-5-chloro-1-[1-(methoxymethyl)propyl]-2(1H)-pyrazinone;

3-[(2,4,6-Trimethylphenyl)amino]-5-chloro-1-[1-(methoxymethyl)-2-methoxyethyl]-2(1H)-pyrazinone;

3-[(2,4,6-Trimethylphenyl)amino]-5-chloro-1-phenyl-2 (1H)-pyrazinone;

(+/−)-3-[(2,4-Dibromophenyl)amino]-5-methyl-1-[1-(methoxymethyl)propyl]-2(1H)-pyrazinone;

(+/−)-3-[[2-Bromo-4-(1-methylethyl)phenyl]amino]-5-methyl-1-[1-(methoxymethyl)propyl]-2(1H)-pyrazinone;

(+/−)-3-[(2,4,6-Trimethylphenyl)amino]-5-methyl-1-[1-(methoxymethyl)propyl]-2(1H)-pyrazinone;

3-[(2,4,6-Trimethylphenyl)amino]-5-methyl-1-[1-(methoxymethyl)-2-methoxyethyl]-2(1H)-pyrazinone;

3-[(2,4-Dichloro-6-methylphenyl)amino]-5-methyl-1-[1-(methoxymethyl)-2-methoxyethyl]-2(1H)-pyrazinone;

3-[(2,4-Dichloro-6-methylphenyl)amino]-5-chloro-1-[1-(methoxymethyl)-2-methoxyethyl]-2(1H)-pyrazinone;

3-[(2,4-Dibromo-6-methylphenyl)amino]-5-chloro-1-[1-(methoxymethyl)-2-methoxyethyl]-2(1H)-pyrazinone;

(+/−)-3-[(2,4,6-Trimethylphenyl)amino]-5-methyl-1-[1-(methoxymethyl)-3-methoxypropyl]-2(1H)-pyrazinone;

(+/−)-3-[(2,4,6-Trimethylphenyl)amino]-5-chloro-1-[1-(methoxymethyl)-3-methoxypropyl]-2(1H)-pyrazinone;

3-[(2,4,6-Trimethylphenyl)amino]-5-chloro-1-[1-(2-methoxyethyl)-3-methoxypropyl]-2(1H)-pyrazinone;

(+/−)-3-[(2,4-Dimethyl-6-methoxyphenyl)amino]-5-chloro-1-[1-(methoxymethyl)propyl]-2(1H)-pyrazinone;

(+/−)-3-[(2,4-Dimethyl-6-methoxyphenyl)amino]-5-chloro-1-[1-(methoxymethyl)-3-methoxypropyl]-2(1H)-pyrazinone;

(+/−)-3-[(2,4-Dimethyl-6-methoxyphenyl)amino]-5-methyl-1-[1-(methoxymethyl)-3-methoxypropyl]-2(1H)-pyrazinone;

(+/−)-3-[(4-Bromo-2,6-dimethylphenyl)amino]-5-methyl-1-[1-(methoxymethyl)-3-methoxypropyl]-2(1H)-pyrazinone;

(+/−)-3-[(2-chloro-4,6-dimethylphenyl)amino]-5-methyl-1-[1-(methoxymethyl)-3-methoxypropyl]-2(1H)-pyrazinone;

(+/−)-3-[[2,4-Dimethyl-6-(methoxymethyl)phenyl]amino]-5-methyl-1-[1-(methoxymethyl)-3-methoxypropyl]-2 (1H)-pyrazinone;

3-[(2,4-Dimethyl-6-methoxyphenyl)amino]-5-methyl-1-[1-(methoxymethyl)-2-methoxyethyl]-2(1H)-pyrazinone;

3-[(4-Bromo-2,6-dimethylphenyl)amino]-5-methyl-1-[1-(methoxymethyl)-2-methoxyethyl]-2(1H)-pyrazinone;

3-[(2-chloro-4,6-dimethylphenyl)amino]-5-methyl-1-[1-(methoxymethyl)-2-methoxyethyl]-2(1H)-pyrazinone;

3-[[2,4-Dimethyl-6-(methoxymethyl)phenyl]amino]-5-methyl-1-[1-(methoxymethyl)-2-methoxyethyl]-2(1H)-pyrazinone;

(+/−)-3-[(2,4-Dimethyl-6-methoxyphenyl)amino]-5-chloro-1-[1-(methoxymethyl)-3-methoxypropyl]-2(1H)-pyrazinone;

(+/−)-3-[(4-Bromo-2,6-dimethylphenyl)amino]-5-chloro-1-[1-(methoxymethyl)-3-methoxypropyl]-2(1H)-pyrazinone;

(+/−)-3-[(2-chloro-4,6-dimethylphenyl)amino]-5-chloro-1-[1-(methoxymethyl)-3-methoxypropyl]-2(1H)-pyrazinone;

(+/−)-3-[[2,4-Dimethyl-6-(methoxymethyl)phenyl]amino]-5-chloro-1-[1-(methoxymethyl)-3-methoxypropyl]-2 (1H)-pyrazinone;

3-[(2,4-Dimethyl-6-methoxyphenyl)amino]-5-chloro-1-[1-(methoxymethyl)-2-methoxyethyl]-2(1H)-pyrazinone;

3-[(4-Bromo-2,6-dimethylphenyl)amino]-5-chloro-1-[1-(methoxymethyl)-2-methoxyethyl]-2(1H)-pyrazinone;

3-[(2-chloro-4,6-dimethylphenyl)amino]-5-chloro-1-[1-(methoxymethyl)-2-methoxyethyl]-2(1H)-pyrazinone;

3-[[2,4-Dimethyl-6-(methoxymethyl)phenyl]amino]-5-chloro-1-[1-(methoxymethyl)-2-methoxyethyl]-2(1H)-pyrazinone;

(+/−)3-[(2,4-Dimethyl-6-methoxyphenyl)amino]-5-chloro-1-(2-methoxy-1-methylethyl)-2(1H)-pyrazinone;

(+/−)3-[(4-Bromo-2,6-dimethylphenyl)amino]-5-chloro-1-(2-methoxy-1-methylethyl)-2(1H)-pyrazinone;

(+/−)3-[(4-Bromo-2,6-dimethylphenyl)amino]-5-chloro-1-[1-(ethoxymethyl)propyl]-2(1H)-pyrazinone;

(+/−)3-[(4-Bromo-2,6-dimethylphenyl)amino]-5-chloro-1-(2-ethoxy-1-methylethyl)-2(1H)-pyrazinone; and (+/−)3-[(4-Bromo-2,6-difluorophenyl)amino]-5-chloro-1-[1-(methoxymethyl)propyl]-2(1H)-pyrazinone;

(+/−)-3-[(2-Bromo-4,6-dimethylphenyl)amino]-5-methyl-1-[1-(methoxymethyl)-3-methoxypropyl]-2(1H) pyrazinone;

(+/−)-3-[(2,4-Dimethyl-6-thiomethylphenyl)amino]-5-methyl-1-[1-(methoxymethyl)-3-methoxypropyl]-2(1H)-pyrazinone;

(+/−)-3-[(2,4-Dimethyl-6-methylsulfonylphenyl)amino]-5-methyl-1-[1-(methoxymethyl)-3-methoxypropyl]-2(1H)-pyrazinone;

(+/−)-3-[(2,6-Dimethyl-4-(N,N-dimethylamino)phenyl)-amino]-5-methyl-1-[1-(methoxymethyl)-3-methoxypropyl]-2(1H)-pyrazinone;

(+/−)-3-[(2,4-Dichloro-6-methylphenyl)amino]-5-methyl-1-[1-(methoxymethyl)-3-methoxypropyl]-2(1H)-pyrazinone;

(+/−)-3-[(4-chloro-2,6-dimethylphenyl)amino]-5-methyl-1-[1-(methoxymethyl)-3-methoxypropyl]-2(1H)-pyrazinone;

(+/−)-3-[(2,6-Dimethyl-4-thiomethylphenyl)amino]-5-methyl-1-[1-(methoxymethyl)-3-methoxypropyl]-2(1H)-pyrazinone;

(+/−)-3-[(2,6-Dimethyl-4-methoxyphenyl)amino]-5-methyl-1-[1-(methoxymethyl)-3-methoxypropyl]-2(1H)-pyrazinone;

(+/−)-3-[(2,6-Dimethyl-4-methylsulfonylphenyl)amino]-5-methyl-1-[1-(methoxymethyl)-3-methoxypropyl]-2(1H)-pyrazinone;

(+/−)-3-[(4-Acetyl-2,6-dimethylphenyl)amino]-5-methyl-1-[1-(methoxymethyl)-3-methoxypropyl]-2(1H)-pyrazinone;
3-[(4-Bromo-2,6-dimethylphenyl)amino]-5-methyl-1-[1-(methoxymethyl)-2-methoxyethyl]-2(1H)-pyrazinone;
3-[(4-Acetyl-2,6-dimethylphenyl)amino]-5-methyl-1-[1-(methoxymethyl)-2-methoxyethyl]-2(1H)-pyrazinone;
3-[(2,6-Dimethyl-4-thiomethylphenyl)amino]-5-methyl-1-[1-(methoxymethyl)-2-methoxyethyl]-2(1H)-pyrazinone;
3-[(2,6-Dimethyl-4-methylsulfonylphenyl)amino]-5-methyl-1-[1-(methoxymethyl)-2-methoxyethyl]-2(1H)-pyrazinone;
3-[(2,6-Dimethyl-4-(N,N-dimethylamino)phenyl)amino]-5-methyl-1-[1-(methoxymethyl)-2-methoxyethyl]-2(1H)-pyrazinone;
3-[(4,6-Dimethyl-2-(N,N-dimethylamino)phenyl)amino]-5-methyl-1-[1-(methoxymethyl)-2-methoxyethyl]-2(1H)-pyrazinone;
(+/−)3-[(2,6-Dimethyl-4-thiomethylphenyl)amino]-5-chloro-1-[1-(methoxymethyl)propyl]-2(1H)-pyrazinone;
(+/−)3-[(2,6-Dimethyl-4-methylsulfonylphenyl)amino]-5-chloro-1-[1-(methoxymethyl)propyl]-2(1H)-pyrazinone;
(+/−)3-[(2-chloro-4,6-dimethylphenyl)amino]-5-chloro-1-[1-(methoxymethyl)propyl]-2(1H)-pyrazinone;
(+/−)3-[(4-Bromo-6-methoxy-2-methylphenyl)amino]-5-chloro-1-[1-(methoxymethyl)propyl]-2(1H)-pyrazinone;
3-[(2,6-Dimethyl-4-thiomethylphenyl)amino]-5-chloro-1-[1-(methoxymethyl)-2-methoxyethyl]-2(1H)-pyrazinone;
3-[(2,6-Dimethyl-4-methylsulfonylphenyl)amino]-5-chloro-1-[1-(methoxymethyl)-2-methoxyethyl]-2(1H)-pyrazinone;
3-[(4-Bromo-6-methoxy-2-methylphenyl)amino]-5-chloro-1-[1-(methoxymethyl)-2-methoxyethyl]-2(1H)-pyrazinone; and
3-[(2,4,6-Trimethylphenyl)amino]-5-methyl-1-(1-ethylpropyl)-2(1H)-pyrazinone.

6. A compound of claim 1 wherein:

Z is $CR^2$;

Y is $NR^4$ or O;

Ar is phenyl or pyridyl, each substituted with 0 to 4 $R^5$ groups;

$R^1$ is H, halo, $C_1$–$C_{10}$ alkyl, $C_2$–$C_{10}$ alkenyl, $C_2$–$C_{10}$ alkynyl, $C_3$–$C_8$ cycloalkyl, $C_1$–$C_4$ haloalkyl, aryl, heterocyclyl, —CN, —$OR^7$, —SH, —$S(O)_nR^{13}$, —$COR^7$, —$CONR^6R^7$, —$CO_2R^7$, —$OC(O)R^{13}$, —$NR^8COR^7$, —$N(COR^7)_2$, —$NR^8CONR^6R^7$, —$NR^8CO_2R^7$, or —$NR^6R^7$, wherein $C_1$–$C_{10}$ alkyl, $C_2$–$C_{10}$ alkenyl, $C_2$–$C_{10}$ alkynyl or $C_3$–$C_8$ cycloalkyl is each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^7$, —SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^7$, —$NR^6R^7$, —$CONR^6R^7$, aryl and heterocyclyl;

$R^2$ is H, $C_1$–$C_4$ alkyl, halo, $C_1$–$C_4$ haloalkyl;

$R^3$ is $C_1$–$C_4$ alkyl, $C_3$–$C_6$ cycloalkyl, $C_1$–$C_4$ haloalkyl and —$NR^6R^7$, wherein $C_1$–$C_4$ alkyl is substituted with 0 to 3 substituents independently selected at each occurrence from $C_1$–$C_4$ alkyl, $C_3$–$C_6$ cycloalkyl, $C_1$–$C_4$ haloalkyl, halo, —CN, —$OR^7$, —$S(O)_nR^{13}$, —$COR^7$, —$CO_2R^7$, —$NR^8COR^7$, —$N(COR^7)_2$, —$NR^8CONR^6R^7$, —$NR^8CO_2R^7$, —$NR^6R^7$ and —$CONR^6R^7$;

$R^4$ is H, $C_1$–$C_6$ alkyl or $C_2$–$C_6$ alkenyl, wherein $C_1$–$C_6$ alkyl is optionally substituted with $C_1$–$C_4$ alkyl, $C_1$–$C_4$ haloalkyl, —$OR^7$, —$S(O)_nR^{12}$, —$CO_2R^7$, —$NR^6R^7$ or —$NR^9COR^{10}$;

$R^5$ is independently selected at each occurrence from $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, aryl, heterocyclyl, —$NO_2$, halo, —CN, $C_1$–$C_4$ haloalkyl, —$NR^6R^7$, —$NR^8COR^7$, —$NR^8CO_2R^7$, —$OR^7$, —$COR^7$, —$CO_2R^7$, —$CONR^6R^7$, —$CON(OR^9)R^7$ and —$S(O)_nR^{13}$, wherein $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are substituted with 0 to 3 substituents independently selected at each occurrence from $C_1$–$C_4$ alkyl, —$NO_2$, halo, —CN, —$OR^7$, —$COR^7$, —$CO_2R^7$, —$CONR^6R^7$, —$NR^6R^7$, —$NR^8COR^7$, —$NR^8CO_2R^7$ and —$S(O)_nR^{13}$;

$R^6$ and $R^7$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heterocyclyl, heterocyclyl ($C_1$–$C_4$ alkyl)-, morpholinoethyl, morpholinopropyl and morpholinobutyl; or —$NR^6R^7$ taken together as a whole is piperidine, pyrrolidine, piperazine, N-methyl-piperazine, morpholine or thiomorpholine;

wherein $C_1$–$C_4$ alkyl, may be substituted with 0 to 2 substituents independently selected at each occurrence from —OH or $C_1$–$C_4$ alkoxy groups;

$R^8$ is independently at each occurrence H or $C_1$–$C_4$ alkyl;

$R^9$ and $R^{10}$ are independently at each occurrence selected from H, $C_1$–$C_4$ alkyl and $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl, $C_1$–$C_4$ haloalkyl or —$NR^6R^7$;

$R^{13}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^6R^7$, aryl, aryl($C_1$–$C_4$ alkyl)-, heterocyclyl or heterocyclyl ($C_1$–$C_4$ alkyl)-;

$R^{14}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, —$NR^{15}R^{16}$;

$R^{15}$ and $R^{16}$ are independently selected at each occurrence from H, $C_1$–$C_4$ alkyl, $C_1$–$C_4$ haloalkyl, $C_2$–$C_8$ alkoxyalkyl, $C_3$–$C_6$ cycloalkyl and $C_4$–$C_{12}$ cycloalkylalkyl; or —$NR^{15}R^{16}$ taken together as a whole is piperidine, pyrrolidine, piperazine, N-methyl-piperazine, morpholine or thiomorpholine;

aryl is phenyl or naphthyl, each substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$, —$NR^8COR^{15}$, —$NR^8CONR^{15}R^{16}$, —$NR^8CO_2R^{15}$ and —$NR^{15}R^{16}$;

heterocyclyl is pyridyl, pyrimidinyl, triazinyl, furanyl, thienyl, imidazolyl, thiazolyl, pyrrolyl, oxazolyl, isoxazolyl or pyrazolyl, each substituted with 0 to 3 substituents independently selected at each occurrence from $C_1$–$C_4$ alkyl, halo, —CN, —$OR^{15}$, —$S(O)_nR^{14}$, —$CO_2R^{15}$, —$NO_2$, —$NR^8COR^{15}$, —$NR^8CONR^{15}R^{16}$, —$NR^8CO_2R^{15}$, and —$NR^{15}R^{16}$; and n is independently at each occurrence 0, 1 or 2.

7. A compound of claim 6 wherein:

Z is $CR^2$;

Y is $NR^4$;

Ar is phenyl or pyridyl, each substituted with 0 to 4 $R^5$ groups;

$R^1$ is H, halo, $C_1$–$C_6$ alkyl, $C_2$–$C_6$ alkenyl, $C_2$–$C_6$ alkynyl, $C_3$–$C_6$ cycloalkyl, $C_1$–$C_4$ haloalkyl, aryl, heterocyclyl, —CN, —$OR^7$, —$S(O)_nR^{13}$, —$COR^7$, —$CONR^6R^7$, —$CO_2R^7$ or —$NR^6R^7$, wherein $C_1$–$C_6$ alkyl, $C_2$–$C_6$ alkenyl, $C_2$–$C_6$ alkynyl or $C_3$–$C_6$ cycloalkyl is each substituted with 0 to 3 substituents independently selected at each occurrence from $C_1$–$C_6$ alkyl, $C_3$–$C_6$ cycloalkyl, halo, $C_1$–$C_4$ haloalkyl, —CN, —$OR^7$, —SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^7$, —$NR^6R^7$, —$CONR^6R^7$, aryl and heterocyclyl;

$R^2$ is H;

$R^3$ is $C_1$–$C_4$ alkyl, $C_3$–$C_6$ cycloalkyl, $C_1$–$C_4$ haloalkyl and —$NR^6R^7$, wherein $C_1$–$C_4$ alkyl is substituted with 0 to 3 substituents independently selected at each occurrence from $C_3$–$C_6$ cycloalkyl, $C_1$–$C_4$ haloalkyl, halo, —CN, —$OR^7$, —$S(O)_nR^{13}$, —$COR^7$, —$CO_2R^7$, —$NR^8COR^7$, —$N(COR^7)_2$, —$NR^8CONR^6R^7$, —$NR^8CO_2R^7$ —$NR^6R^7$ and —$CONR^6R^7$;

$R^4$ is H, allyl, or $C_1$–$C_4$ alkyl, wherein $C_1$–$C_4$ alkyl is optionally substituted with $C_1$–$C_4$ alkyl, —$OR^7$, —$S(O)_2R^{12}$, —$CO_2R^7$, —$NR^6R^7$ or —$NR^9COR^{10}$;

$R^5$ is independently selected at each occurrence from $C_1$–$C_6$ alkyl, aryl, heterocyclyl, $C_1$–$C_4$ haloalkyl, halo, —CN, —$NO_2$, —$NR^6R^7$, —$COR^7$, —$OR^7$, —$CONR^6R^7$, —$CON(OR^9)R^7$, —$CO_2R^7$ and —$S(O)_nR^{13}$, wherein $C_1$–$C_6$ alkyl is substituted with 0 to 3 substituents independently selected at each occurrence from $C_1$–$C_4$ alkyl, —$NO_2$, halo, —CN, —$NR^6R^7$, $COR^7$, —$OR^7$, —$CONR^6R^7$, $CO_2R^7$ and —$S(O)_nR^{13}$;

$R^6$ and $R^7$ are independently selected at each occurrence from H, $C_1$–$C_4$ alkyl, $C_1$–$C_4$ haloalkyl and $C_2$–$C_8$ alkoxyalkyl;

wherein $C_1$–$C_4$ alkyl, may be substituted with 0 to 2 substituents independently selected at each occurrence from —OH or $C_1$–$C_4$ alkoxy groups;

$R^8$, $R^9$ and $R^{10}$ are independently at each occurrence H or $C_1$–$C_4$ alkyl;

$R^{12}$ and $R^{13}$ are independently at each occurrence $C_1$–$C_4$ alkyl or —$NR^6R^7$;

$R^{14}$ is $C_1$–$C_4$ alkyl or —$NR^{15}R^{16}$;

$R^{15}$ and $R^{16}$ are independently at each occurrence H, $C_1$–$C_4$ alkyl or $C_2$–$C_8$ alkoxyalkyl;

aryl is phenyl substituted with 0 to 3 substituents independently selected at each occurrence from $C_1$–$C_4$ alkyl, halo, —CN, —$OR^{15}$, —$S(O)_nR^{14}$, —$COR^{15}$, —$CO_2R^{15}$, —$NO_2$ and —$NR^{15}R^{16}$; and n is independently at each occurrence 0, 1 or 2.

8. A method for treating anxiety in a mammal in need of such treatment comprising administering to the mammal a therapeutically effective amount of a compound having a composition of claim 1.

9. A method for treating anxiety in a mammal in need of such treatment comprising administering to the mammal a therapeutically effective amount of a compound having a composition of claim 2.

10. A method for treating anxiety in a mammal in need of such treatment comprising administering to the mammal a therapeutically effective amount of a compound having a composition of claim 3.

11. A method for treating anxiety in a mammal in need of such treatment comprising administering to the mammal a therapeutically effective amount of a compound having a composition of claim 4.

12. A method for treating anxiety in a mammal in need of such treatment comprising administering to the mammal a therapeutically effective amount of a compound having a composition of claim 5.

13. A method for treating anxiety in a mammal in need of such treatment comprising administering to the mammal a therapeutically effective amount of a compound having a composition of claim 6.

14. A method for treating anxiety in a mammal in need of such treatment comprising administering to the mammal a therapeutically effective amount of a compound having a composition of claim 7.

15. A pharmaceutical composition comprising a pharmaceutically acceptable carrier and a therapeutically effective amount of a compound having a composition of claim 1.

16. A pharmaceutical composition comprising a pharmaceutically acceptable carrier and a therapeutically effective amount of a compound having a composition of claim 2.

17. A pharmaceutical composition comprising a pharmaceutically acceptable carrier and a therapeutically effective amount of a compound having a composition of claim 3.

18. A pharmaceutical composition comprising a pharmaceutically acceptable carrier and a therapeutically effective amount of a compound having a composition of claim 4.

19. A pharmaceutical composition comprising a pharmaceutically acceptable carrier and a therapeutically effective amount of a compound having a composition of claim 5.

20. A pharmaceutical composition comprising a pharmaceutically acceptable carrier and a therapeutically effective amount of a compound having a composition of claim 6.

21. A pharmaceutical composition comprising a pharmaceutically acceptable carrier and a therapeutically effective amount of a compound having a composition of claim 7.

22. A method for treating depression in a mammal in need of such treatment comprising administering to the mammal a therapeutically effective amount of a compound having a composition of claim 1.

23. A method for treating depression in a mammal in need of such treatment comprising administering to the mammal a therapeutically effective amount of a compound having a composition of claim 2.

24. A method for treating depression in a mammal in need of such treatment comprising administering to the mammal a therapeutically effective amount of a compound having a composition of claim 3.

25. A method for treating depression in a mammal in need of such treatment comprising administering to the mammal a therapeutically effective amount of a compound having a composition of claim 4.

26. A method for treating depression in a mammal in need of such treatment comprising administering to the mammal a therapeutically effective amount of a compound having a composition of claim 5.

27. A method for treating depression in a mammal in need of such treatment comprising administering to the mammal a therapeutically effective amount of a compound having a composition of claim 6.

28. A method for treating depression in a mammal in need of such treatment comprising administering to the mammal a therapeutically effective amount of a compound having a composition of claim 7.

* * * * *